US008710038B2

(12) United States Patent
Baik et al.

(10) Patent No.: US 8,710,038 B2
(45) Date of Patent: Apr. 29, 2014

(54) PYRAZOLE KINASE MODULATORS AND METHODS OF USE

(75) Inventors: Tae-Gon Baik, Foster City, CA (US);
Chris A. Buhr, Redwood City, CA (US);
Sunghoon Ma, Foster City, CA (US);
John M. Nuss, Danville, CA (US);
Zerom Tesfai, Castro Valley, CA (US);
Longcheng Wang, Palo Alto, CA (US);
Bryan K. S. Yeung, Chromos (SG)

(73) Assignee: Exelixis, Inc., South San Francisco, CA (US)

( * ) Notice: Subject to any disclaimer, the term of this patent is extended or adjusted under 35 U.S.C. 154(b) by 576 days.

(21) Appl. No.: 11/575,411

(22) PCT Filed: Sep. 15, 2005

(86) PCT No.: PCT/US2005/032839
§ 371 (c)(1),
(2), (4) Date: Mar. 16, 2007

(87) PCT Pub. No.: WO2006/033943
PCT Pub. Date: Mar. 30, 2006

(65) Prior Publication Data
US 2007/0293507 A1  Dec. 20, 2007

Related U.S. Application Data

(60) Provisional application No. 60/610,689, filed on Sep. 17, 2004.

(51) Int. Cl.
*C07D 403/00*    (2006.01)
*A01N 43/00*    (2006.01)
*A61K 31/33*    (2006.01)

(52) U.S. Cl.
USPC ............................................ 514/183; 544/370

(58) Field of Classification Search
USPC ............................................ 514/183; 544/370
See application file for complete search history.

(56) References Cited

U.S. PATENT DOCUMENTS

| 3,948,937 | A |  | 4/1976 | Johnson et al. |
| 4,014,896 | A |  | 3/1977 | Garber et al. |
| 4,075,342 | A |  | 2/1978 | Sale et al. |
| 4,877,881 | A |  | 10/1989 | Belliotti et al. |
| 5,208,251 | A |  | 5/1993 | Belliotti et al. |
| 5,468,871 | A |  | 11/1995 | Ebel et al. |
| 5,475,017 | A |  | 12/1995 | Wuest et al. |
| 5,744,614 | A |  | 4/1998 | Merkle et al. |
| 2004/0006057 | A1 |  | 1/2004 | Reiter et al. |
| 2005/0113423 | A1 | * | 5/2005 | VanGoor et al. ............ 514/341 |
| 2007/0213364 | A1 |  | 9/2007 | Yasuma et al. |
| 2008/0125418 | A1 |  | 5/2008 | Babin et al. |

FOREIGN PATENT DOCUMENTS

| CA | 2361636 A1 | 8/2000 |
| DE | 923 028 C | 1/1955 |
| EP | 0 245 825 B1 | 3/1991 |
| JP | 04-124178 A | 4/1992 |
| WO | 00/07996 A2 | 2/2000 |
| WO | 00/19994 A1 | 4/2000 |
| WO | 01/45703 A1 | 6/2001 |
| WO | 01/87287 A2 | 11/2001 |
| WO | 02/085897 A1 | 10/2002 |
| WO | 02/100826 A2 | 12/2002 |
| WO | 03/035065 | 5/2003 |
| WO | WO 03/059886 | * 7/2003 |
| WO | WO03/088927 A2 | 10/2003 |
| WO | WO03/105751 A2 | 12/2003 |
| WO | WO2004/080972 A1 | 9/2004 |
| WO | WO2004/099164 A1 | 11/2004 |
| WO | 2005/047273 A1 | 5/2005 |
| WO | 2005/094823 A1 | 10/2005 |
| WO | 96/34851 A1 | 11/2006 |

OTHER PUBLICATIONS

Wright et. al. (J. Med. Chem. (1964) 7:102-105).*
El- Emary et. al. (Phosphorus, Sulfur and Silicon (2002) 177:195-210).*
J. G. Cannon, Chapter Nineteen in Burger's Medicinal Chemistry and Drug Discovery, Fifth Edition, vol. I: Principles and Practice, Wiley-Interscience 1995, pp. 783-802).*
Tanitame et al., "Synthesis and Antibacterial Activity of a Novel Series of Potent DNA Gyrase Inhibitors, Pyrazole Derivatives", Journal of Medicinal Chemistry, 2004, 3693-3696, 47(14).
International Search Report for associated application PCT/US2005/032839 prepared by the ISA/US and mailed Mar. 13, 2006.
Tanitame, A. et al., "Synthesis and Antibacterial Activity of a Novel Series of Potent DNA Gyrase Inhibitors, Pyrazole Derivatives", J. Med. Chem., vol. 47, pp. 3693-3696, 2004.
Supplementary Partial European Search Report issued Aug. 7, 2009 for parallel European Patent Application 05796701.0.
Al-Omran F. et al., "Synthesis of Polyfunctionally Substituted Heteroaromatic Compounds via Benzotriazolyl Chalcones With Antimicrobial and Antifungal Activities", Journal of Heterocyclic Chem., vol. 41, pp. 327-333, 2004.
Dornow, A. et al., "Uber Die Alkalispaltung N-Substituierter Benzolsulfon-Hydrazide", Liebigs Ann. Chem., vol. 602, pp. 23-36, 1957.
Flynn, D.L. et al., "Styrylpyrazoles, Styrylisoxazoles and Styrylisothiazoles. Novel 5-Lipoxygenase and Cyclooxygenase Inhibitors", J. Med. Chem, vol. 34, No. 2, pp. 518-525, 1991.
Grimshaw, J. et al., "Electrochemical Reactions. Part VII. Selective Dehalogenation of Styrylpyrazoline and Styrylpyrazole Derivatives", J. Chem. Soc., Perkin Trans. 1, pp. 1383-1388, 1974.
Hauser, C.R. et al., "N- and C-Benzoylation of p-Aminoacetophenone with Methyl Benzoate by Sodium Amide. Synthesis of .beta.-Diketones Having p-Acylamino and p-Hydroxy Groups", J. Org. Chem., vol. 22, pp. 909-912, 1957.

(Continued)

*Primary Examiner* — Marcos Sznaidman
(74) *Attorney, Agent, or Firm* — McDonnell Boehnen Hulbert & Berghoff LLP

(57) ABSTRACT

The present invention provides compounds for modulating protein kinase enzymatic activity for modulating cellular activities such as proliferation, differentiation, programmed cell death, migration and chemoinvasion. Compounds of the invention inhibit, regulate and/or modulate kinases. Methods of using the compounds and pharmaceutical compositions thereof to treat kinase-dependent diseases and conditions are also an aspect of the invention.

8 Claims, No Drawings

(56) References Cited

OTHER PUBLICATIONS

Ishida J. et al., "Antitumor Agents. Part 214: Synthesis and Evaluation of Curcumin Analogues as Cytotoxic Agents", Bioorg. Med. Chem., vol. 10, pp. 3481-3487, 2002.

Jorlander, H., "Uber das Anisoyl-phenyl-oxidoathan", Chem. Ber., vol. 49, pp. 2782-2795, 1916.

Light, R.J. et al., "Condensations of Dialkali .beta.-Diketones with Ketones or Aldehydes to Form Hydroxy .beta.-Diketones. Dehydration Products. Equilibrium Factors", J. Org. Chem., vol. 26, pp. 1716-1724, 1961.

Ohtsu, H. et al., "Antitumor Agents. 217. Curcumin Analogues as Novel Androgen Receptor Antagonists with Potential as Anti-Prostate Cancer Agents", J. Med. Chem., vol. 45, No. 23, pp. 5037-5042, 2002.

Pinto, D.C.G.A., et al., "Synthesis and Molecular Structure of 3-(2-Benzyloxy-6-hydroxyphenyl)-5-styrylpyrazoles. Reaction of 2-Styrylchromones and Hydrazine Hydrate", Tetrahedron, vol. 55, No. 33, pp. 10187-10200, 1999.

Robertson, I. R., et al., "A Study of Periselectivity in the Thermal Cyclisation Reactions of Diene-Conjugated Diazo Compounds: 1,7-Cyclisation as a Route to 3H-1, 2-Diazepines and 1,5-Cyclisation Leading to New Rearrangement Reactions of 3H-Pyrazoles", Tetrahedron, vol. 40, No. 16, pp. 3095-3112, 1984.

Sammour, A. et al., "Some Reactions with 3-Methyl-1H-Naphtho[2,1-b]pyran-1-One", J. Prakt. Chem., vol. 314, No. 2, pp. 271-280, 1972.

Shim, J. S., et al., "Hydrazinocurcumin, a Novel Synthetic Curcumin Derivative, is a Potent Inhibitor of Endothelial Cell Proliferation", Bioorg. Med. Chem., vol. 10, No. 8, pp. 2439-2444, 2002.

Silva, V.L.M. et al., "3(5)-(2-Hydroxyphenyl)-5(3)-Styrylpyrazoles: Synthesis and Diels—Alder Transformations", Eur. J. Org. Chem., No. 21, pp. 4348-4356, 2004.

Wieland, H., "Zur Kenntnis des p-Nitrodibenzoylmethans", Chem. Ber. vol. 37, pp. 1148-1152, 1904.

Kumar, A. et al., "Synthesis of novel heterocyclic compounds: Routes to pyrazolyl 1,2,3-triazoles and their biological activity evaluation", Indian Journal of Chemistry, 2003, vol. 42B, 1950-1957.

Palkar, R. B. et al., "Synthesis of some new 3,5-diarylpyrazoles and their antibacterial activity", Indian Journal of Heterocyclic Chemistry, 1999, vol. 8, 315-318.

Musante, C. et al., "Su alcuni nuovi derivati della "Khellina" e del suo prodotto di demetilazione", Annali di Chimica, 1955, vol. 45, 918-942, Italy.

Pryor, A. et al., "Purification of maize alcohol dehydrogenase and competitive inhibition by pyrazoles", Biochemistry International, 1982, 4(4), 431-438.

Colotta, V. et al., "Synthesis and binding activity of some pyrazolo[1,5-c]quinazolines as tools to verify an optional binding site of a benzodiazepine receptor ligand", J. Med. Chem., 1996, vol. 39, 2915-2921.

Essassi, E. M. et al., "Synthese et hererocyclisation des (pyrazolyl-3(5))-2 benzimidazoles en catalyse par transfert de phase", Bulletin des Societes Chimiques Belges, 1987, 96(1), 63-67.

Elkaschef, M. A. F. et al., "4-pyrones: Part VI—Reactions of chromones & thiochromones with amines", Indian Journal of Chemistry, 1973, 11(9), 860-862.

Mahmound et al., "Synthesis and some reactions of pyrimidine-2-thione derivatives", Indian Journal of Chemistry, 1992, 39(9), 830-835.

Otto et al., "Tripanocide Diamidine mit dreo isolierten Ringsystemen", Justus Liebigs Annalen Der Chemie, 1975, vol. 1975, 160-194, Compound 44 and definition of "Am" in the chemical graphic on second page of document.

EPO Communication under Article 94(3) issued on May 7, 2013 in European Patent Application No. 05 796 701.0, 6 pages.

* cited by examiner

PYRAZOLE KINASE MODULATORS AND METHODS OF USE

REFERENCE TO RELATED APPLICATIONS

This application is a US national phase of international application PCT/US2005/032839 filed on Sep. 15, 2005, which claims priority to U.S. Provisional Patent Application Ser. No. 60/610,689 filed on Sep. 17, 2004, the disclosure of which is incorporated herein by reference.

BACKGROUND OF THE INVENTION

1. Field of the Invention

This invention relates to compounds for modulating protein kinase enzymatic activity for modulating cellular activities such as proliferation, differentiation, programmed cell death, migration and chemoinvasion. Even more specifically, the invention relates to compounds that inhibit, regulate and/or modulate kinases, particularly Kit and flt-3. Kinase receptor signal transduction pathways related to the changes in cellular activities as mentioned above are modulated using compounds of the invention. Methods of using the compounds to treat kinase-dependent diseases and conditions are also an aspect of the invention.

2. Summary of Related Art

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Protein kinases are enzymes that catalyze the phosphorylation of proteins, in particular, hydroxy groups on tyrosine, serine and threonine residues of proteins. The consequences of this seemingly simple activity are staggering; cell differentiation and proliferation; i.e., virtually all aspects of cell life in one-way or another depend on protein kinase activity. Furthermore, abnormal protein kinase activity has been related to a host of disorders, ranging from relatively non-life threatening diseases such as psoriasis to extremely virulent diseases such as glioblastoma (brain cancer).

Protein kinases can be categorized as receptor type or non-receptor type. Receptor-type tyrosine kinases have an extracellular, a transmembrane, and an intracellular portion, while non-receptor type tyrosine kinases are wholly intracellular.

Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and beta receptors, CSFIR, c-kit and FLK-II. Then there is the FLK family, which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., DN&P 7(6): 334-339, 1994, which is hereby incorporated by reference.

The non-receptor type of tyrosine kinases is also comprised of numerous subfamilies, including Src, Frk, Btk, Csk, Ab1, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, Oncogene, 8:2025-2031 (1993), which is hereby incorporated by reference.

Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases. These include, but are not limited to: immunological disorders, cardiovascular diseases, inflammatory diseases, and degenerative diseases. Therefore, both receptor and non-receptor protein kinases are attractive targets for small molecule drug discovery.

One attractive goal for therapeutic use of kinase modulation relates to oncological indications. For example, modulation of protein kinase activity for the treatment of cancer has been demonstrated successfully with the FDA approval of Gleevec® (imatinib mesylate, produced by Novartis Pharmaceutical Corporation of East Hanover, N.J.) for the treatment of Chronic Myeloid Leukemia (CML) and gastrointestinal stroma cancers (GIST). Gleevec is a c-Kit and Ab1 kinase inhibitor.

Modulation (particularly inhibition) of cell proliferation and angiogenesis, two key cellular processes needed for tumor growth and survival (Matter A. Drug Disc Technol 2001 6, 1005-1024), is an alluring goal for development of small-molecule drugs. Anti-angiogenic therapy represents a potentially important approach for the treatment of solid tumors and other diseases associated with dysregulated vascularization, including ischemic coronary artery disease, diabetic retinopathy, psoriasis and rheumatoid arthritis. As well, cell antiproliferative agents are desirable to slow or stop the growth of tumors.

One particularly attractive target for small-molecule modulation is c-Kit. The proto-oncogene c-Kit was first identified as the oncogenic component of the acutely transforming Hardy-Zuckerman 4-feline sarcoma virus (Besmer et al Nature 1986 320:415-421). c-Kit (also called stem cell factor receptor or steel factor receptor) is a type 3 receptor tyrosine kinase (RTK) belonging to the platelet-derived growth factor receptor subfamily. c-Kit binds the ligand stem cell factor (SCF), and triggers its multiple signal transduction pathways including Src family kinases, phosphatidyl-inositol 3 kinase, the Ras-Raf-Map kinase cascade, and phospholipase C (Broudy et al Blood 1999 94: 1979-1986; Lennartsson et al Oncogene 1999 18: 5546-5553; Timokhina et al EMBO J 1998 17; 6250-6262; Chian et al Blood 2001 98(5)1365-1373; Blume-Jensen et al Curr Biol 1998 8:779-782; Kissel et al EMBO J 2000 19:1312-1326; Lennartsson et al. Oncogene 1999 18: 5546-5553; Sue et al Blood, 199892:1242-1149; Lev etal EMBO J 1991 10:647-654). c-Kit is required for normal hematopoiesis, melanonogenesis, and gametogenesis. c-Kit is expressed in mast cells, immature myeloid cells, melanocytes, epithelial breast cells and the interstitial cells of Cajal (ICC). In mast cells, it is required not only for the differentiation, maturation, chemotaxis, and haptotaxis but also for the promotion of survival and proliferation.

Mutations in c-Kit have been implicated in human disease. Mutations in the juxtamembrane domain are found in many human gastrointestinal stromal tumors, and mutations in the kinase domain are found in mastocytosis, germ cell tumors, acute myeloid leukemia (AML), NK lymphoma, and other hematologic disorders (Hirota et al Science 1998 279:577-580; Singer et al J Clin Oncol 2002 203898-3905; Longley et al Proc Natl Aca Sci USA 1999: 1609-1614; Tian et al Am J Pathol 1999 154: 1643-1647; Beghini et al Blood 2000 95:726-727; Hongyo et al Cancer Res 2000 60:2345-2347). These mutations result in ligand-independent tyrosine kinase activity, autophosphorylation of c-Kit, uncontrolled cell proliferation, and stimulation of downstream signaling pathways. Overexpression of c-Kit and c-Kit ligand have also been described in other tumors including small-cell lung cancer, neuroblastomas, gynecological tumors, and colon carcinoma, which might result in autocrine or paracrine c-Kit activation.

The overexpression of c-Kit has also been implicated in the development of neoplasia associated with neurofibromatosis type 1 (NF1). Mutations in the tumor suppressor gene NF1 lead to a deficiency in neurofibromin, a GTPase-activating protein for Ras. This deficiency results in abnormal proliferation of Schwann cells in the peripheral nervous system, and predisposes affected individuals to peripheral nerve sheath tumors (neurofibromas), astrocytomas (optic pathway gliomas), learning disabilities, seizures, strokes, macrocephaly, vascular abnormalities, and juvenile myelomonocytic leukemia (Lynch & Gutmann Neurol Clin 2002 20:841-865). Genetic experiments in mice demonstrate that haploinsufficiency at NF1 partially rescues some of the phenotypes associated with mutations in the gene for c-Kit, indicating that these genes function along a common developmental pathway (Ingram, et al. J. Exp Med 2000 191:181-187). Also, c-Kit is expressed in schwannoma cells from NF1 patients, but not in normal schwann cells (Ryan et al. J Neurosci Res 1994 37:415-432). These data indicate that elevated c-Kit expression and sensitivity to stem cell factor may play important roles in the development of proliferative disorders associated with NF-1. Therefore, c-Kit inhibitors may be effective chemotherapeutic agents for treating patients with NF-1.

GISTs are the most common mesenchymal tumors of the gastrointestinal tract, and they are generally resistant to chemotherapy and radiation therapy. However, recent results with the c-Kit/BCR-Ab1 inhibitor STI571 indicate that targeting c-Kit may be an effective therapeutic strategy for this disease (Eisenberg & Mehren Expert Opin Pharmacother 2003 4:869-874). Malignant mast cell disease often suggests an extremely poor prognosis, and no reliable effective chemotherapeutic agents have been identified (Marone et al Leuk Res 2001 25:583-594). Systemic mast cell disorders have been treated with interferon-alpha, although the effectiveness of this therapy has been variable (Lehmann & Lammle Ann Hematol 1999 78:483-484; Butterfield Br J Dermatol 1998 138: 489-495). Therefore, activated c-Kit might serve as a therapeutic target in GISTs and mast cell disease, as well as other disorders associated with activated c-Kit.

Flt-3 is normally expressed on hematopoietic progenitor cells and a subset of mature myeloid and lymphoid cells, where it modulates cell survival and proliferation. Flt-3 is constitutively activated via mutation, either in the juxtamembrane region or in the activation loop of the kinase domain, in a large proportion of patients with AML (Reilly Leuk Lymphoma 2003 44: 1-7). Also, mutations in flt-3 are significantly correlated with poor prognosis in AML patients (Sawyers Cancer Cell 2002 1: 413-415).

Accordingly, the identification of small-molecule compounds that specifically inhibit, regulate, and/or modulate the signal transduction of kinases, particularly c-Kit and flt-3, is desirable as a means to treat or prevent disease states associated with abnormal cell proliferation, and is an object of this invention.

SUMMARY OF THE INVENTION

In one aspect, the present invention provides compounds for modulating c-Kit and flt-3 kinase activity and methods of treating diseases mediated by c-Kit and flt-3 activity utilizing the compounds and pharmaceutical compositions described herein. Diseases mediated by c-Kit and flt-3 activity include, but are not limited to, diseases characterized in part by migration, invasion, proliferation and other biological activities associated with invasive cell growth.

In another aspect, the invention provides methods of screening for modulators of c-Kit and flt-3 activity. The methods comprise combining a composition of the invention, c-Kit or flt-3, and at least one candidate agent and determining the effect of the candidate agent on the c-Kit or flt-3 activity.

In yet another aspect, the invention also provides pharmaceutical c-Kits comprising one or more containers filled with one or more of the ingredients of pharmaceutical compounds and/or compositions of the present invention, including, one or more c-Kit or flt-3 enzyme activity modulators as described herein. Such c-Kits can also include, for example, other compounds and/or compositions (e.g., diluents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflect approval by the agency of manufacture, use or sale for human administration.

In still yet another aspect, the invention also provides a diagnostic agent comprising a compound of the invention and, optionally, pharmaceutically acceptable adjuvants and excipients.

These and other features and advantages of the present invention will be described in more detail below with reference to the associated drawings.

DETAILED DESCRIPTION OF THE INVENTION

The compositions of the invention are used to treat diseases associated with abnormal and or unregulated cellular activities. Disease states which can be treated by the methods and compositions provided herein include, but are not limited to, cancer (further discussed below), immunological disorders such as rheumatoid arthritis, graft-host diseases, multiple sclerosis, psoriasis; cardiovascular diseases such as artheroscrosis, myocardioinfarction, ischemia, stroke and restenosis; other inflammatory and degenerative diseases such as interbowel diseases, osteoarthritus, macular degeneration, diabetic retinopathy.

It is appreciated that in some cases the cells may not be in a hyper- or hypo-proliferative and/or migratory state (abnormal state) and still require treatment. For example, during wound healing, the cells may be proliferating "normally", but proliferation and migration enhancement may be desired. Alternatively, reduction in "normal" cell proliferation and/or migration rate may be desired.

The present invention comprises a compound for modulating kinase activity, particularly c-Kit and/or flt-3, according to Formula I,

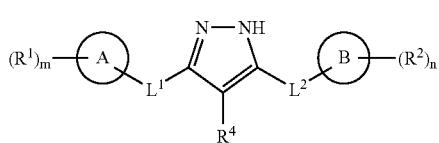

or a pharmaceutically acceptable salt, hydrate, or prodrug thereof, wherein, each of $R^1$ and $R^2$ is independently selected from —H, halogen, haloalkyl, haloalkoxy, —CN, —NO$_2$, —OR$^3$, —N(R$^3$)R$^3$, —S(O)$_{0-2}$R$^3$, —N(R$^3$)C(=O)N(R$^3$)R$^3$, —N(R$^3$)C(=O)C(=O)N(R$^3$)R$^3$, —SO$_2$N(R$^3$)R$^3$, —CO$_2$R$^3$, —C(=O)N(R$^3$)R$^3$, —C(=NR$^5$)N(R$^3$)R$^3$, —C(=NR$^5$)R$^3$, —N(R$^3$)SO$_2$R$^3$, —N(R$^3$)C(O)R$^3$, —NCO$_2$R$^3$, —N(R$^3$)C(O)$_2$R$^3$, —C(=O)R$^3$, optionally substituted alkoxy, optionally substituted lower alkyl, optionally substituted aryl, optionally substituted lower arylalkyl, optionally substituted cycloalkyl, optionally substituted cycloalkylalkyl, optionally substituted heteroaryl, optionally substituted heteroarylalkyl, optionally substituted heterocyclyl, or optionally substituted lower heterocyclylalkyl;

each of m and n is independently one to five;

each of A and B is independently selected from a five- to ten-membered aryl or heteroaryl;

$R^3$ is selected from —H, optionally substituted lower alkyl, optionally substituted aryl, optionally substituted lower arylalkyl, optionally substituted heterocyclyl, or optionally substituted lower heterocyclylalkyl;

two of $R^3$, together with the nitrogen to which they are attached, can combine to form an optionally substituted heterocyclyl containing between one and three additional heteroatoms;

$R^4$ is selected from —H, halogen or optionally substituted lower alkyl;

each $R^5$ is independently selected from —H, —CN, —NO$_2$, —OR$^3$, —S(O)$_{0-2}$R$^3$, —CO$_2$R$^3$, optionally substituted lower alkyl, optionally substituted lower alkenyl, and optionally substituted lower alkynyl; and each of $L^1$ and $L^2$ is independently selected from absent or —C(R$^3$)=C(R$^3$)—;

provided the compound is not either N'-[3-[5-(3-chlorophenyl)-1H-pyrazol-3-yl]phenyl]-N,N-dimethyl-urea (registry number 143704-64-7) or N'-[3-[5-(2-chlorophenyl)-1H-pyrazol-3-yl]phenyl]-N,N-dimethyl-urea (registry number 143704-63-6), and provided the compound is not according to formula i,

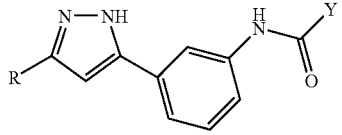

wherein R is lower alkyl or optionally substituted phenyl; and Y is lower alkyl, lower alkenyl, lower alkoxy, lower alkenyloxy, N,N-dialkylamino, and N-lower alkyl-N-lower alkoxyamino.

In one example, the compound according to [0023], wherein substitutents such as alkoxy, alkyl, alkenyl, alkynyl, aryl, arylalkyl, cycloalkyl, cycloalkylalkyl, heteroaryl, heteroarylalkyl, heterocyclyl or heterocyclylalkyl is optionally substituted with one or more substituents independently selected from the group consisting of alkyl, alkoxy, halo, haloalkyl, haloalkoxy, —CN, —NO$_2$, —OR$^3$, —N(R$^3$)R$^3$, —S(O)$_{0-2}$R$^3$, —N(R$^3$)C(=O)N(R$^3$)R$^3$, —N(R$^3$)C(=O)C(=O)N(R$^3$)R$^3$, —SO$_2$N(R$^3$)R$^3$, —CO$_2$R$^3$, —C(=O)N(R$^3$)R$^3$, —C(=NR$^5$)N(R$^3$)R$^3$, —C(=NR$^5$)R$^3$, —N(R$^3$)SO$_2$R$^3$, —N(R$^3$)C(O)R$^3$, —NCO$_2$R$^3$, —N(R$^3$)C(O)$_2$R$^3$, —C(=O)R$^3$, optionally substituted aryl, optionally substituted arylalkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl.

In one example, the compound is according to paragraph [0023], wherein $R^4$ is —H.

In another example, the compound is according to paragraph [0036], wherein $L^1$ and L are both —C(R$^3$)=C(R$^3$)—.

In another example, the compound is according to paragraph [0037], wherein $L^1$ and L are both E— —C(R$^3$)=C(R$^3$)—.

In another example, the compound is according to paragraph [0038], of formula II,

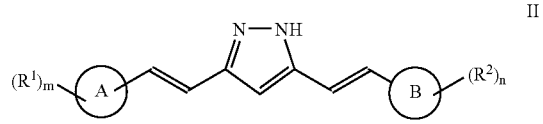

wherein each of $R^1$ and $R^2$ is independently selected from —H, halogen, haloalkyl, haloalkoxy, —CN, —NO$_2$, —OR$^3$, —N(R$^3$)R$^3$, —S(O)$_{0-2}$R$^3$, —N(R$^3$)C(=O)N(R$^3$)R$^3$, —N(R$^3$)C(=O)C(=O)N(R$^3$)R$^3$, —SO$_2$N(R$^3$)R$^3$, —CO$_2$R$^3$, —C(=O)N(R$^3$)R$^3$, —C(=NR$^5$)N(R$^3$)R$^3$, —C(=NR$^5$)R$^3$, —N(R$^3$)SO$_2$R$^3$, —N(R$^3$)C(O)R$^3$, —N(R$^3$)C(O)$_2$R$^3$, —NCO$_2$R$^3$, —C(=O)R$^3$, optionally substituted alkoxy, optionally substituted lower alkyl, optionally substituted heteroaryl, optionally substituted cycloalkyl, optionally substituted heterocyclyl or optionally substituted aryl;

each of A and B is a radical independently selected from the group consisting of phenyl, benzothiophenyl, pyridyl, pyrazinyl, benzofuranyl, benzpyrazolyl, benzoxazolyl, naphthyl, benzimidazolyl, indolyl, and biphenyl.

In another example, the compound is according to paragraph [0039], of formula IIa,

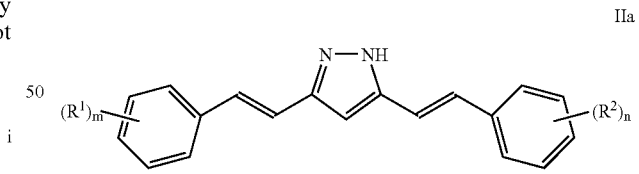

wherein each of $R^1$ and $R^2$ is independently selected from —H, halogen, haloalkyl, haloalkoxy, —CN, —NO$_2$, —OR$^3$, —N(R$^3$)R$^3$, —S(O)$_{0-2}$R$^3$, —N(R$^3$)C(=O)N(R$^3$)R$^3$, —N(R$^3$)C(=O)C(=O)N(R$^3$)R$^3$, —SO$_2$N(R$^3$)R$^3$, —CO$_2$R$^3$, —C(=O)N(R$^3$)R$^3$, —C(=NR$^5$)N(R$^3$)R$^3$, —C(=NR$^5$)R$^3$, —N(R$^3$)SO$_2$R$^3$, —N(R$^3$)C(O)R$^3$, —N(R$^3$)C(O)$_2$R$^3$, —NCO$_2$R$^3$, —C(=O)R$^3$, optionally substituted aryl, optionally substituted alkoxy, optionally substituted lower alkyl, optionally substituted heteroaryl, optionally substituted cycloalkyl, optionally substituted heterocyclyl or optionally substituted aryl.

In another example, the compound is according to paragraph [0042], wherein each of $R^1$ and $R^2$ is independently selected from —H, halogen, haloalkyl, haloalkoxy, —CN, —NO$_2$, —OR$^3$, —N(R$^3$)R$^3$, —C(=O)R$^3$, or optionally substituted lower alkyl.

In another example, the compound is according to paragraph [0043], wherein R$^1$ is selected from —H, halogen, haloalkyl, haloalkoxy, —CN, —NO$_2$, and optionally substituted lower alkyl; and R$^2$ is selected from —H, —OR$^3$, —N(R$^3$)R$^3$, or optionally substituted lower alkyl.

In another example, the compound is according to paragraph [0044], wherein R$^1$ is selected from —H, halogen, haloalkyl or haloalkoxy; and R$^2$ is selected from —H, —OR$^3$, —N(R$^3$)R$^3$, or optionally substituted lower alkyl.

In another example, the compound is according to paragraph [0045], of formula III,

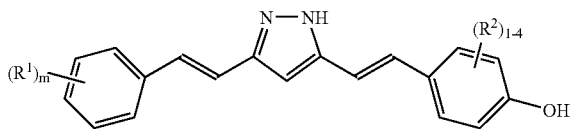

III wherein R$^1$ is selected from —H, halogen, haloalkyl or haloalkoxy; and R$^2$ is selected from —H, —OR$^3$, —N(R$^3$)R$^3$, or optionally substituted lower alkyl.

In another example, the compound is according to paragraph [0036], wherein L$^1$ is absent and L$^2$ is —C(R$^3$)=C(R$^3$)—.

In another example, the compound is according to paragraph [0047], wherein L$^1$ is absent and L$^2$ is —C(H)=C(H)—.

In another example, the compound is according to paragraph [0048], of formula IV,

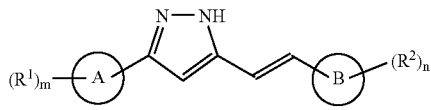

IV wherein each of R$^1$ and R$^2$ is independently selected from —H, halogen, haloalkyl, haloalkoxy, —CN, —NO$_2$, —OR$^3$, —N(R$^3$)R$^3$, —S(O)$_{0-2}$R$^3$, —N(R$^3$)C(=O)N(R$^3$)R$^3$, —N(R$^3$)C(=O)C(=O)N(R$^3$)R$^3$, —SO$_2$N(R$^3$)R$^3$, —CO$_2$R$^3$, —C(=O)N(R$^3$)R$^3$, —C(=NR$^5$)N(R$^3$)R$^3$, —C(=NR$^5$)R$^3$, —N(R$^3$SO$_2$R$^3$, —N(R$^3$)C(O)R$^3$, —N(R$^3$)C(O)$_2$R$^3$, —NCO$_2$R$^3$, —C(=O)R$^3$, optionally substituted alkoky, optionally substituted heterocyclyl, optionally substituted lower alkyl, optionally substituted aryl, optionally substituted heteroaryl, or optionally substituted cycloalkyl; and each A and B is a radical independently selected from phenyl, benzothiophenyl, pyridyl, pyrazinyl, benzofuranyl, naphthyl, benzimidazolyl, indolyl, or biphenyl.

In another example, the compound is according to paragraph [0049], of formula IVa,

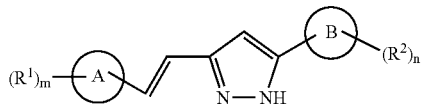

IVa wherein each of R$^1$ and R$^2$ is independently selected from —H, halogen, haloalkyl, haloalkoxy, —CN, —NO$_2$, —OR$^3$, —N(R$^3$)R$^3$, —S(O)$_{0-2}$R$^3$, —N(R$^3$)C(=O)N(R$^3$)R$^3$, —N(R$^3$)C(=O)C(=O)N(R$^3$)R$^3$, —SO$_2$N(R$^3$)R$^3$, —CO$_2$R$^3$, —C(=O)N(R$^3$)R$^3$, —C(=NR$^5$)N(R$^3$)R$^3$, —C(=NR$^5$)R$^3$, —N(R$^3$SO$_2$R$^3$, —N(R$^3$)C(O)R$^3$, —N(R$^3$)C(O)$_2$R$^3$, —NCO$_2$R$^3$, —C(=O)R$^3$, optionally substituted alkoxy, optionally substituted heterocyclyl, optionally substituted lower alkyl, optionally substituted aryl, optionally substituted heteroaryl, or optionally substituted cycloalkyl; and each A and B is a radical independently selected from the group consisting of phenyl, benzothiophenyl, pyridyl, pyrazinyl, benzofuranyl, benzpyrazolyl, benzoxazolyl, naphthyl, benzimidazolyl, indolyl, and biphenyl.

In another example, the compound is according to paragraph [0050], of formula V,

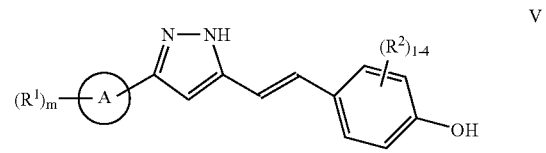

V wherein each of R$^1$ and R$^2$ is independently selected from —H, halogen, haloalkyl, haloalkoxy, —CN, —NO$_2$, —OR$^3$, —N(R$^3$)R$^3$, —S(O)$_{0-2}$R$^3$, —CO$_2$R$^3$, —C(=O)N(R$^3$)R$^3$, —N(R$^3$)SO$_2$R$^3$, —N(R$^3$)C(O)R$^3$, —N(R$^3$)C(O)$_2$R$^3$, —NCO$_2$R$^3$, —C(=O)R$^3$, optionally substituted alkoxy, optionally substituted heterocyclyl, optionally substituted lower alkyl, optionally substituted aryl, optionally substituted heteroaryl, or optionally substituted cycloalkyl; and A is a radical selected from phenyl, benzothiophenyl, pyridyl, benzofuranyl, benzimidazolyl, or indolyl.

In another example, the compound is according to paragraph [0051], wherein A is either phenyl or 2-benzimidazolyl.

In another example, the compound is according to paragraph [0052], wherein A is substituted with at least one of —N(R$^3$)R$^3$, an optionally substituted heteroalicyclyl, or a lower alkyl substituted with at least one of —N(R$^3$)R$^3$.

In another example, the compound is according to paragraph [0036], wherein L$^1$ and L$^2$ are both absent.

In another example, the compound is according to paragraph [0054], wherein A is a six- or nine-membered aryl or heteroaryl and B is a six-membered aryl or heteroaryl.

In another example, the compound is according to paragraph [0055], of formula VI,

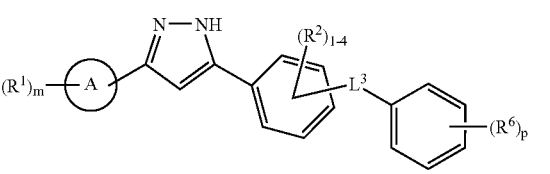

VI wherein each of R$^1$, R$^2$ and R$^6$ is independently selected from —H, halogen, haloalkyl, haloalkoxy, —CN, —NO$_2$, —OR$^3$, —N(R$^3$)R$^3$, —S(O)$_{0-2}$R$^3$, —N(R$^3$)C(=O)N(R$^3$)R$^3$, —N(R$^3$)C(=O)C(=O)N(R$^3$)R$^3$, —N(R$^3$)C(=S)N(R$^3$)R$^3$, —SO$_2$N(R$^3$)R$^3$, —CO$_2$R$^3$, —C(=O)N(R$^3$)R$^3$, —C(=NR$^5$)N(R$^3$)R$^3$, —C(=NR$^5$)R$^3$, —N(R$^3$)SO$_2$R$^3$, —N(R$^3$)C(O)R$^3$, —N(R$^3$)C(O)$_2$R$^3$, —NCO$_2$R$^3$, —C(=O)R$^3$, optionally substituted alkoxy, optionally substituted heterocyclyl, optionally substituted lower alkyl, optionally substituted aryl, optionally substituted heteroaryl, or optionally substituted cycloalkyl; p is one to five; A is a radical selected from phenyl, benzothiophenyl, pyridyl, pyrazinyl, benzofuranyl, benzimidazolyl, or indolyl; L$^3$ is selected from absent, —(CH$_2$)$_{0-1}$N(R$^3$)C(=O)N(R$^3$)—, —N(R$^3$)C(=O)N(R$^3$)(CH$_2$)$_{0-1}$—, —(CH$_2$)$_{0-1}$N(R$^3$)C(=O)—, —N(R$^3$)C(=O)(CH$_2$)$_{0-1}$—, —(CH$_2$)$_{0-1}$SO$_2$N(R$^3$)—, —SO$_2$N(R$^3$)(CH$_2$)$_{0-1}$—, —C(=NR$^5$)N(R$^3$)—, —C(=NR$^5$)—, —(CH$_2$)$_{0-1}$N(R$^3$)CO$_2$—, —N(R$^3$)CO$_2$(CH$_2$)$_{0-1}$—, —C(=O)—, —CO$_2$—, —(CH$_2$)$_{0-1}$N(R$^3$)C(=NR$^5$)N(R$^3$)—, or —(CH$_2$)$_{0-1}$N(R$^3$)—.

In another example, the compound is according to paragraph [0056], wherein when A is phenyl, L$^3$ is —N(R$^3$)C(=O)N(R$^3$)—.

In another example, the compound is according to paragraph [0057], wherein A is either phenyl or benzimidazolyl.

In another example, the compound is according to paragraph [0058], of either formula VIIa or VIIb,

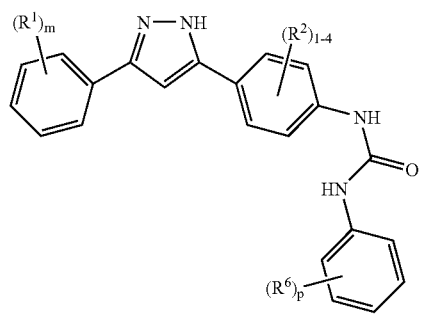

VIIa

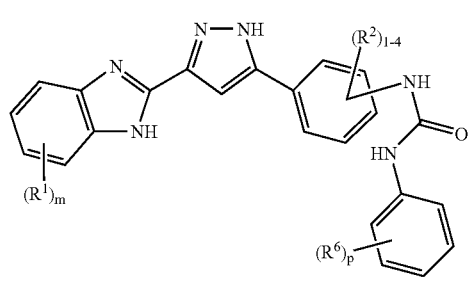

VIIb wherein R$^1$ is selected from —H, halogen, haloalkyl, haloalkoxy, —CN, —NO$_2$, —OR$^3$, —N(R$^3$)R$^3$, —S(O)$_{0-2}$R$^3$, —CO$_2$R$^3$, —C(=O)N(R$^3$)R$^3$, —N(R$^3$)SO$_2$R$^3$, —N(R$^3$)C(O)R$^3$, —NCO$_2$R$^3$, —C(=O)R$^3$, optionally substituted alkoxy, optionally substituted heterocyclyl, optionally substituted lower alkyl, optionally substituted aryl, optionally substituted heteroaryl, or optionally substituted cycloalkyl; m is one to five; R$^2$ is selected from —H, halogen, haloalkyl, —CN, —NO$_2$, —OR$^3$, —N(R$^3$)R$^3$, or optionally substituted lower alkyl; R$^6$ is selected from —H, halogen, haloalkyl, —CN, —NO$_2$, —OR$^3$, —N(R$^3$)R$^3$, —S(O)$_{0-2}$R$^3$, —N(R$^3$)C(=O)C(=O)N(R$^3$)R$^3$, —CO$_2$R$^3$, —C(=O)N(R$^3$)R$^3$, —N(R$^3$)SO$_2$R$^3$, —N(R$^3$)C(O)R$^3$, —NCO$_2$R$^3$, —C(=O)R$^3$, optionally substituted alkoxy, optionally substituted heterocyclyl, or optionally substituted lower alkyl; p is one to five.

In another example, the compound is according to paragraph [0059] wherein the phenyl urea in VIIb is either meta- or para- to the pyrazole moiety.

In another example, the compound is according to paragraph [0060], of either formula VIIc or VIId,

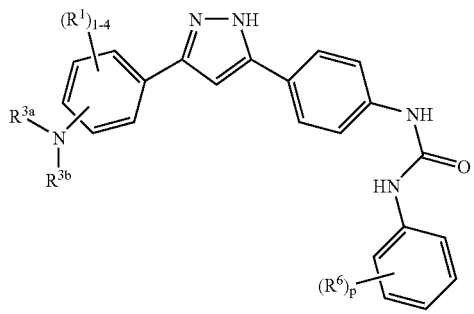

VIIc

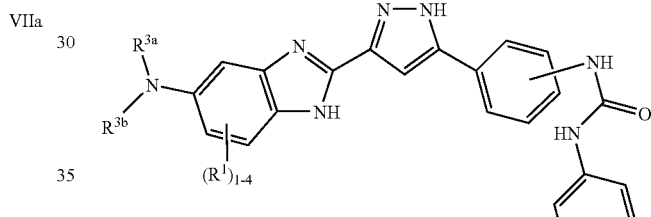

VIId wherein R$^1$ is selected from —H, halogen, haloalkyl, haloalkoxy, —CN, —NO$_2$, —OR$^3$, —N(R$^3$)R$^3$, —S(O)$_{0-2}$R$^3$, —CO$_2$R$^3$, —C(=O)N(R$^3$)R$^3$, —N(R$^3$)SO$_2$R$^3$, —N(R$^3$)C(O)R$^3$, —NCO$_2$R$^3$, —C(=O)R$^3$, optionally substituted alkoxy, optionally substituted heterocyclyl, or optionally substituted lower alkyl, optionally substituted aryl, optionally substituted heteroaryl, or optionally substituted cycloalkyl; R$^{3a}$ and R$^{3b}$ are each independently selected from —H or optionally substituted lower alkyl; optionally R$^{3a}$ and R$^{3b}$, together with the nitrogen to which they are attached, combine to form an optionally substituted heteroalicyclyl containing between one and two additional heteroatoms; R$^6$ is selected from —H, halogen, haloalkyl, —CN, —NO$_2$, —OR$^3$, —N(R$^3$)R$^3$, —S(O)$_{0-2}$R$^3$, —N(R$^3$)C(=O)C(=O)N(R$^3$)R$^3$, —CO$_2$R$^3$, —C(=O)N(R$^3$)R$^3$, —N(R$^3$)SO$_2$R$^3$, —N(R$^3$)C(O)R$^3$, —NCO$_2$R$^3$, —C(=O)R$^3$, optionally substituted alkoxy, optionally substituted heterocyclyl, or optionally substituted lower alkyl; p is one to five;

In another example, the compound is according to paragraph [0061], wherein for formula VIIc, —N(R$^{3a}$)R$^{3b}$ is either meta- or para- to the pyrazole moiety; and the phenyl urea in VIId is either meta- or para- to the pyrazole moiety.

In another example, the compound is according to paragraph [9023], selected from Table 1.

TABLE 1

| Entry | Name | Structure |
|---|---|---|
| 1 | 4-((E)-2-{3-[6-(4-methylpiperazin-1-yl)-1H-benzimidazol-2-yl]-1H-pyrazol-5-yl}ethenyl)phenol | 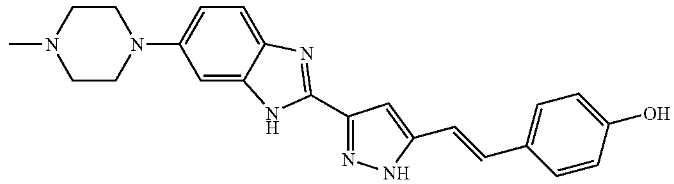 [SMILES: CN1CCN(c2ccc3nc(-c4cc(/C=C/c5ccc(O)cc5)[nH]n4)[nH]c3c2)CC1] |
| 2 | N-[4-chloro-3-(trifluoromethyl)phenyl]-N'-(4-{3-[5-(4-ethylpiperazin-1-yl)-1H-benzimidazol-2-yl]-1H-pyrazol-5-yl}phenyl)urea | 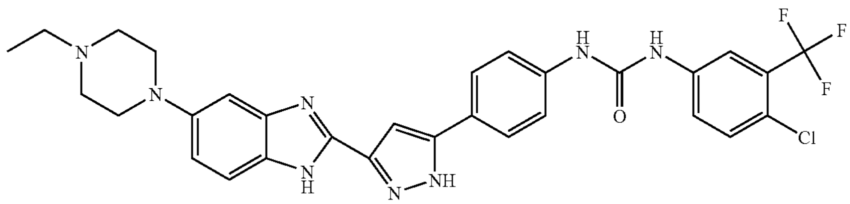 [SMILES: CCN1CCN(c2ccc3[nH]c(-c4cc(-c5ccc(NC(=O)Nc6ccc(Cl)c(C(F)(F)F)c6)cc5)[nH]n4)nc3c2)CC1] |
| 3 | N-(3-ethylphenyl)-N'-(4-{3-[5-(4-ethylpiperazin-1-yl)-1H-benzimidazol-2-yl]-1H-pyrazol-5-yl}phenyl)urea | 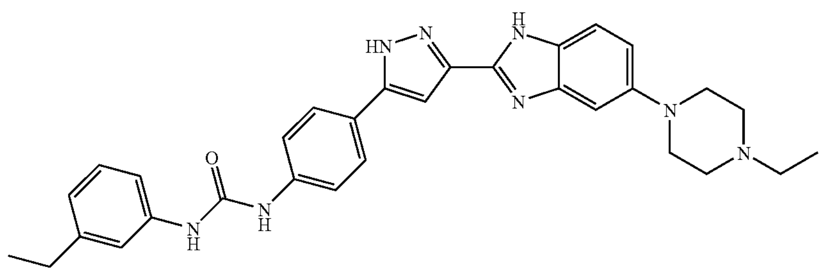 [SMILES: CCc1cccc(NC(=O)Nc2ccc(-c3cc(-c4nc5cc(N6CCN(CC)CC6)ccc5[nH]4)n[nH]3)cc2)c1] |
| 4 | N-(4-{3-[5-(4-ethylpiperazin-1-yl)-1H-benzimidazol-2-yl]-1H-pyrazol-5-yl}phenyl)-N'-[3-(trifluoromethyl)phenyl]urea | 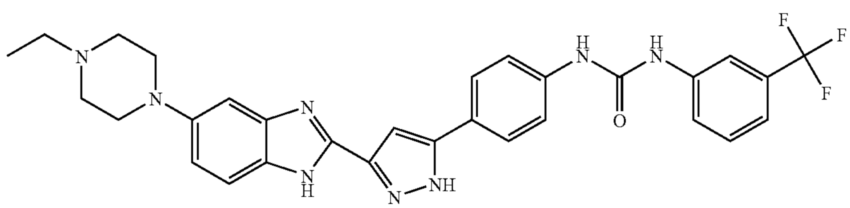 [SMILES: CCN1CCN(c2ccc3[nH]c(-c4cc(-c5ccc(NC(=O)Nc6cccc(C(F)(F)F)c6)cc5)[nH]n4)nc3c2)CC1] |
| 5 | N-(3-acetylphenyl)-N'-(4-{3-[5-(4-methylpiperazin-1-yl)-1H-benzimidazol-2-yl]-1H-pyrazol-5-yl}phenyl)urea | 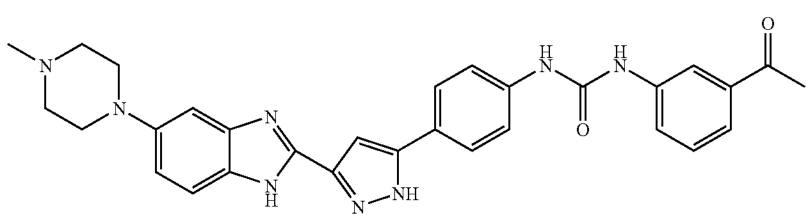 [SMILES: CC(=O)c1cccc(NC(=O)Nc2ccc(-c3cc(-c4nc5cc(N6CCN(C)CC6)ccc5[nH]4)n[nH]3)cc2)c1] |
| 6 | N-(3,4-dichlorophenyl)-N'-(4-{3-[5-(4-methylpiperazin-1-yl)-1H-benzimidazol-2-l]-1H-pyrazol-5-yl}phenyl)urea | 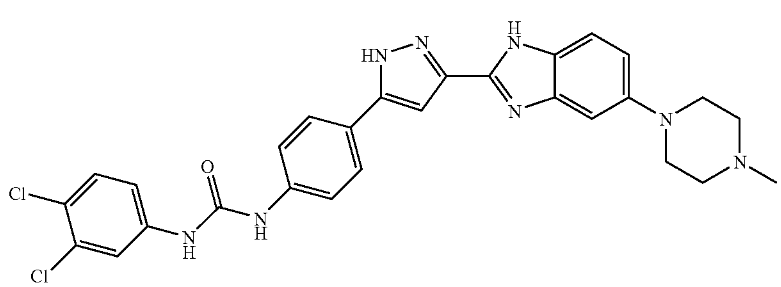 [SMILES: CN1CCN(c2ccc3[nH]c(-c4cc(-c5ccc(NC(=O)Nc6ccc(Cl)c(Cl)c6)cc5)[nH]n4)nc3c2)CC1] |

TABLE 1-continued

| Entry | Name | Structure |
|---|---|---|
| 7 | N-(3-bromophenyl)-N'-(4-{3-[6-(4-methylpiperazin-1-yl)-1H-benzimidazol-2-yl]-1H-pyrazol-5-yl}phenyl)urea | 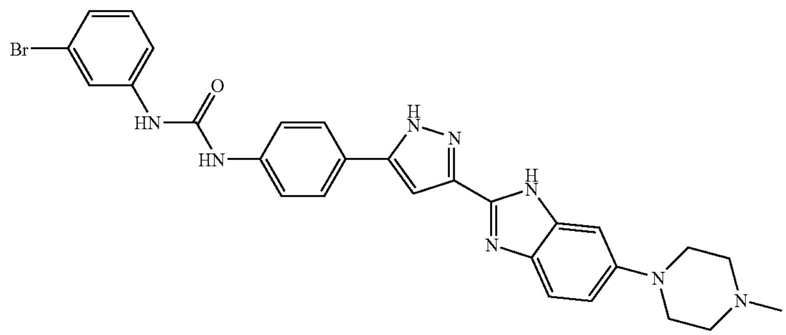 [SMILES: CN1CCN(c2ccc3nc(-c4cc(-c5ccc(NC(=O)Nc6cccc(Br)c6)cc5)[nH]n4)[nH]c3c2)CC1] |
| 8 | N-[4-fluoro-3-(trifluoromethyl)phenyl]-N'-(4-{3-[5-(4-methylpiperazin-1-yl)-1H-benzimidazol-2-yl]-1H-pyrazol-5-yl}phenyl)urea | 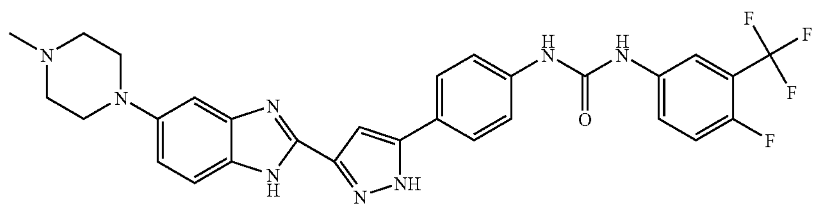 [SMILES: CN1CCN(c2ccc3[nH]c(-c4cc(-c5ccc(NC(=O)Nc6ccc(F)c(C(F)(F)F)c6)cc5)[nH]n4)nc3c2)CC1] |
| 9 | N-(4-{3-[5-(4-methylpiperazin-1-yl)-1H-benzimidazol-2-yl]-1H-pyrazol-5-yl}phenyl)-N'-[4-(phenyloxy)phenyl]urea | 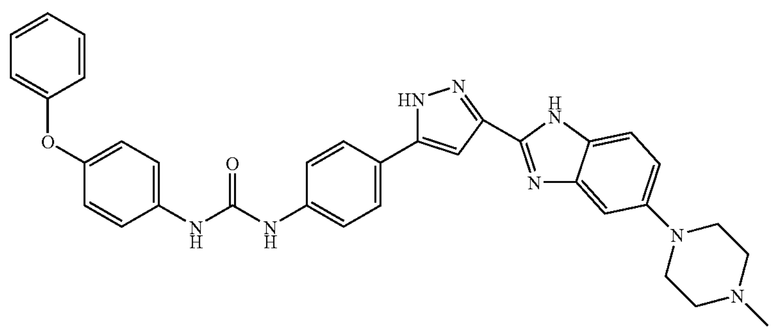 [SMILES: CN1CCN(c2ccc3[nH]c(-c4cc(-c5ccc(NC(=O)Nc6ccc(Oc7ccccc7)cc6)cc5)[nH]n4)nc3c2)CC1] |
| 10 | N-(3-chlorophenyl)-N'-(4-{3-[5-(4-methylpiperazin-1-yl)-1H-benzimidazol-2-yl]-1H-pyrazol-yl}phenyl)urea | 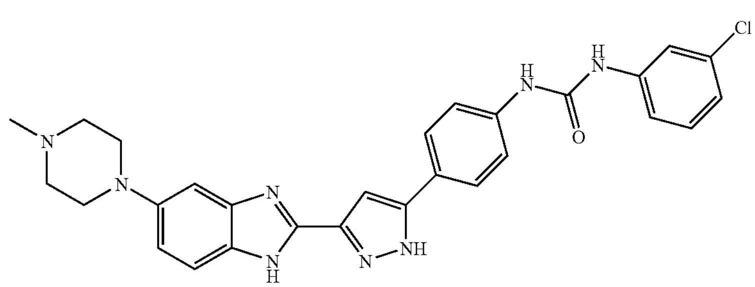 [SMILES: CN1CCN(c2ccc3[nH]c(-c4cc(-c5ccc(NC(=O)Nc6cccc(Cl)c6)cc5)[nH]n4)nc3c2)CC1] |
| 11 | N-[3,5-bis(methyloxy)phenyl]-N'-(4-{3-[6-(4-methylpiperazin-1-yl)-1H-benzimidazol-2-yl]-1H-pyrazol-5-yl}phenyl)urea | 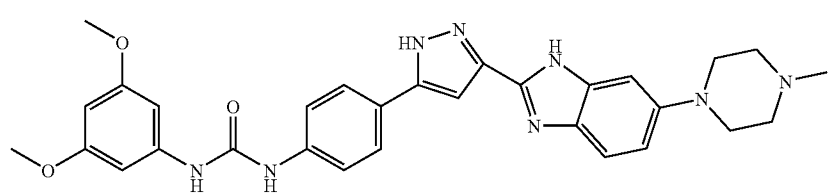 |

TABLE 1-continued

| Entry | Name | Structure |
|---|---|---|
| 12 | N-(4-{3-[5-(4-methylpiperazin-1-yl)-1H-benzimidazol-2-yl]-1H-pyrazol-5-yl}phenyl)-N'-{4-[(trifluoromethyl)oxy]phenyl}urea | 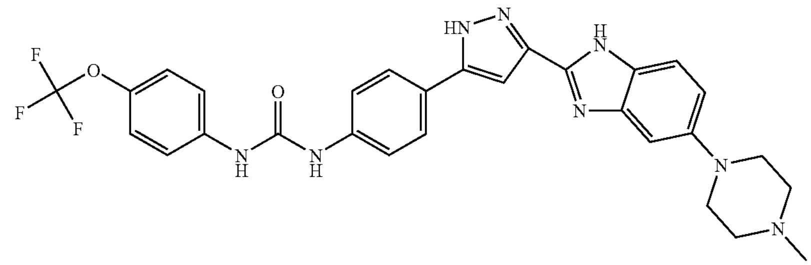 [SMILES: CN1CCN(c2ccc3[nH]c(-c4cc(-c5ccc(NC(=O)Nc6ccc(OC(F)(F)F)cc6)cc5)[nH]n4)nc3c2)CC1] |
| 13 | N-(4-{3-[6-(4-methylpiperazin-1-yl)-1H-benzimidazol-2-yl]-1H-pyrazol-5-yl}phenyl)-N'-[4-(trifluoromethyl)phenyl]urea | 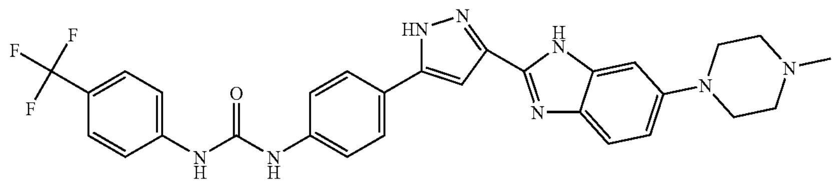 [SMILES: CN1CCN(c2ccc3nc(-c4cc(-c5ccc(NC(=O)Nc6ccc(C(F)(F)F)cc6)cc5)[nH]n4)[nH]c3c2)CC1] |
| 14 | N-[4-chloro-3-(trifluoromethyl)phenyl]-N'-(4-{3-[5-(4-methylpiperazin-1-yl)-1H-benzimidazol-2-yl]-1H-pyrazol-5-yl}phenyl)urea | 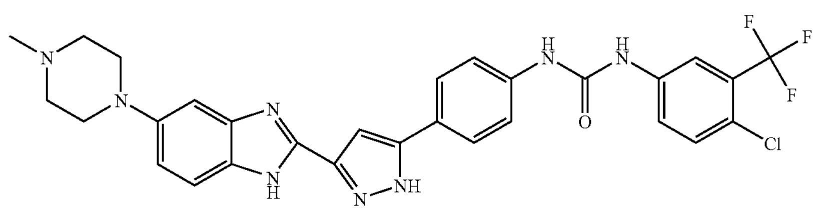 |
| 15 | N-(4-{3-[5-(4-methylpiperazin-1-yl)-1H-benzimidazol-2-yl]-1H-pyrazol-5-yl}phenyl)-N'-[3-(trifluoromethyl)phenyl]urea | 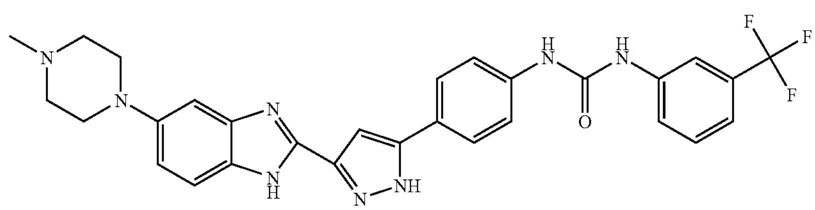 [SMILES: CN1CCN(c2ccc3[nH]c(-c4cc(-c5ccc(NC(=O)Nc6cccc(C(F)(F)F)c6)cc5)[nH]n4)nc3c2)CC1] |
| 16 | N-[4-chloro-3-(trifluoromethyl)phenyl]-N'-(4-{3-[4-(4-methylpiperazin-1-yl)phenyl]-1H-pyrazol-5-yl}phenyl)urea | 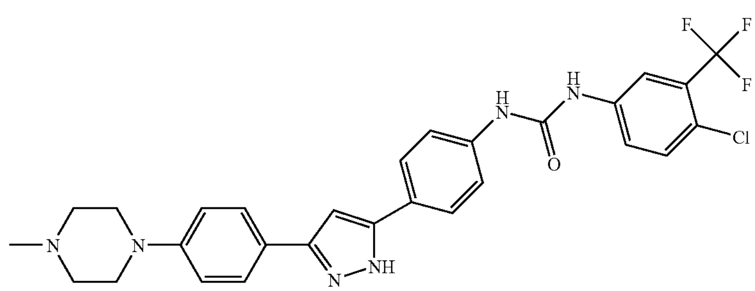 [SMILES: CN1CCN(c2ccc(-c3cc(-c4ccc(NC(=O)Nc5ccc(Cl)c(C(F)(F)F)c5)cc4)[nH]n3)cc2)CC1] |
| 17 | N-(3,4-dimethylphenyl)-N'-(4-{5-[4-(4-methylpiperazin-1-yl)phenyl]-1H-pyrazol-3-yl}phenyl)urea | 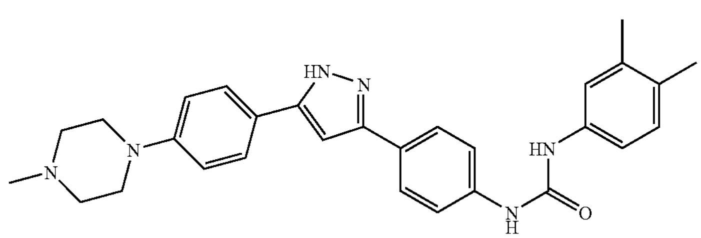 |

TABLE 1-continued

| Entry | Name | Structure |
|---|---|---|
| 18 | N-(4-chlorophenyl)-N'-(4-{3-[5-(4-methylpiperazin-1-yl)-1H-benzimidazol-2-yl]-1H-pyrazol-5-yl}phenyl)urea | 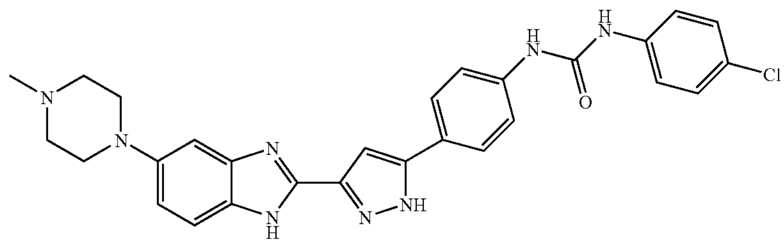 [SMILES: CN1CCN(c2ccc3[nH]c(-c4cc(-c5ccc(NC(=O)Nc6ccc(Cl)cc6)cc5)[nH]n4)nc3c2)CC1] |
| 19 | N-(3,5-difluorophenyl)-N'-(4-{3-[5-(4-methylpiperazin-1-yl)-1H-benzimidazol-2-yl]-1H-pyrazol-5-yl}phenyl)urea | 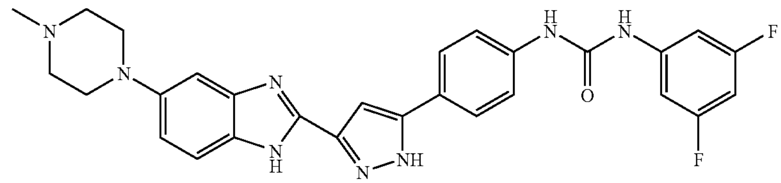 [SMILES: CN1CCN(c2ccc3[nH]c(-c4cc(-c5ccc(NC(=O)Nc6cc(F)cc(F)c6)cc5)[nH]n4)nc3c2)CC1] |
| 20 | N-[3-(methyloxy)phenyl]-N'-(4-{3-[5-(4-methylpiperazin-1-yl)-1H-benzimidazol-2-yl]-1H-pyrazol-5-yl}phenyl)urea | 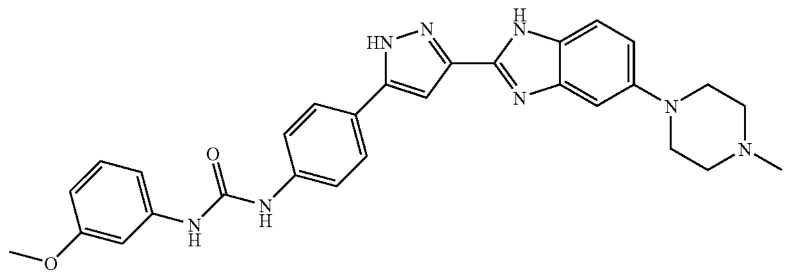 |
| 21 | N-[4-chloro-3-(trifluoromethyl)phenyl]-N'-(4-{3-[4-(4-ethylpiperazin-1-yl)phenyl]-1H-pyrazol-5-yl}phenyl)urea | 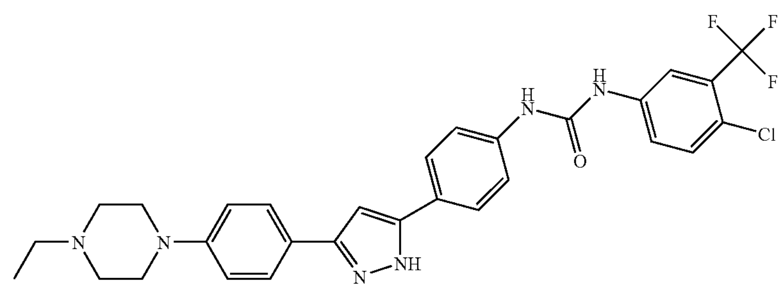 [SMILES: CCN1CCN(c2ccc(-c3cc(-c4ccc(NC(=O)Nc5ccc(Cl)c(C(F)(F)F)c5)cc4)[nH]n3)cc2)CC1] |
| 22 | N-(3-fluorophenyl)-N'-(4-{3-[5-(4-methylpiperazin-1-yl)-1H-benzimidazol-2-yl]-1H-pyrazol-5-yl}phenyl)urea | 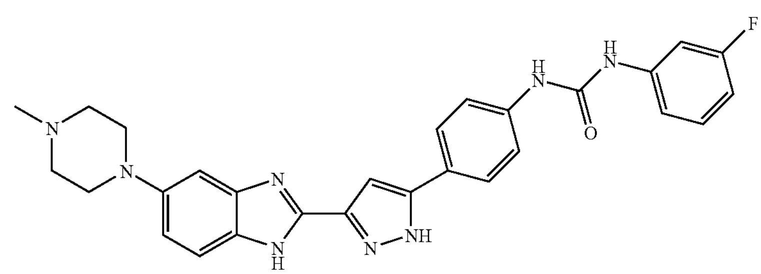 [SMILES: CN1CCN(c2ccc3[nH]c(-c4cc(-c5ccc(NC(=O)Nc6cccc(F)c6)cc5)[nH]n4)nc3c2)CC1] |
| 23 | N-(4-fluorophenyl)-N'-(4-{3-[5-(4-methylpiperazin-1-yl)-1H-benzimidazol-2-yl]-1H-pyrazol-5-yl}phenyl)urea | 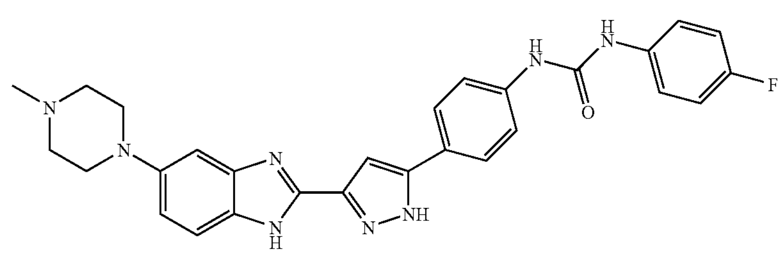 [SMILES: CN1CCN(c2ccc3[nH]c(-c4cc(-c5ccc(NC(=O)Nc6ccc(F)cc6)cc5)[nH]n4)nc3c2)CC1] |

TABLE 1-continued

| Entry | Name | Structure |
|---|---|---|
| 24 | N-(3-cyanophenyl)-N'-(4-{3-[6-(4-methylpiperazin-1-yl)-1H-benzimidazol-2-yl]-1H-pyrazol-5-yl}phenyl)urea | 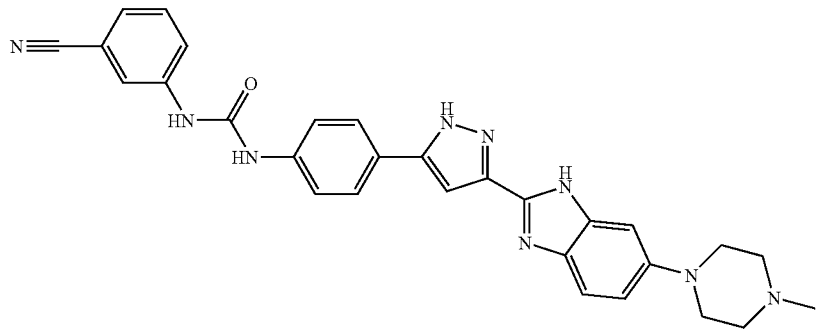 [SMILES: CN1CCN(c2ccc3nc(-c4cc(-c5ccc(NC(=O)Nc6cccc(C#N)c6)cc5)[nH]n4)[nH]c3c2)CC1] |
| 25 | N-(3,4-difluorophenyl)-N'-(4-{3-[5-(4-methylpiperazin-1-yl)-1H-benzimidazol-2-yl]-1H-pyrazol-5-yl}phenyl)urea | 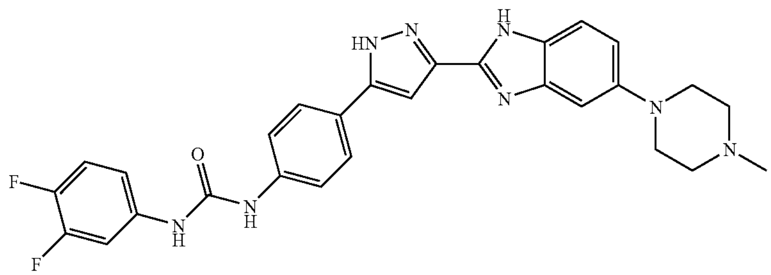 [SMILES: CN1CCN(c2ccc3[nH]c(-c4cc(-c5ccc(NC(=O)Nc6ccc(F)c(F)c6)cc5)[nH]n4)nc3c2)CC1] |
| 26 | N-[3,4-bis(methyloxy)phenyl]-N'-(4-{3-[5-(4-methylpiperazin-1-yl)-1H-benzimidazol-2-yl]-1H-pyrazol-5-yl}phenyl)urea | 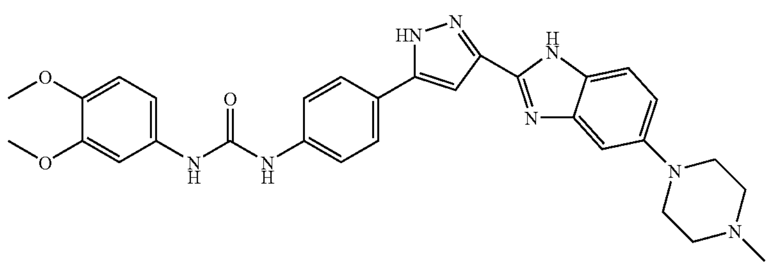 |
| 27 | N-[5-chloro-2-(methyloxy)phenyl]-N'-(4-{5-[4-(4-methylpiperazin-1-yl)phenyl]-1H-pyrazol-3-yl}phenyl)urea | 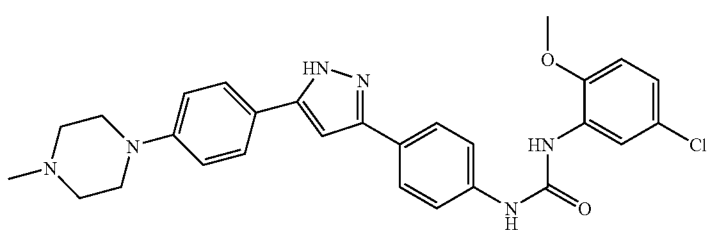 [SMILES: COc1ccc(Cl)cc1NC(=O)Nc1ccc(-c2cc(-c3ccc(N4CCN(C)CC4)cc3)[nH]n2)cc1] |
| 28 | N-(4-{5-[4-(4-methylpiperazin-1-yl)phenyl]-1H-pyrazol-3-yl}phenyl)-N'-[4-(phenyloxy)phenyl]urea | 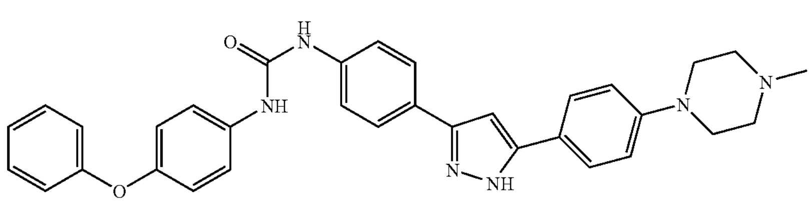 [SMILES: CN1CCN(c2ccc(-c3cc(-c4ccc(NC(=O)Nc5ccc(Oc6ccccc6)cc5)cc4)n[nH]3)cc2)CC1] |

TABLE 1-continued

| Entry | Name | Structure |
|---|---|---|
| 29 | N-(2,4-difluorophenyl)-N'-(4-{3-[6-(4-ethylpiperazin-1-yl)-1H-benzimidazol-2-yl]-1H-pyrazol-5-yl}phenyl)urea | 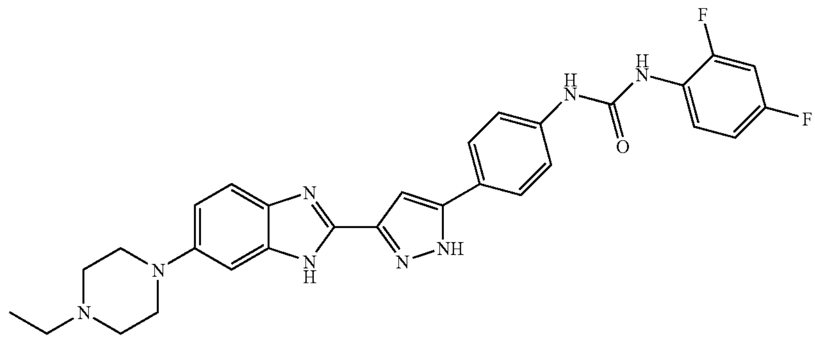 [SMILES: CCN1CCN(c2ccc3nc(-c4cc(-c5ccc(NC(=O)Nc6ccc(F)cc6F)cc5)[nH]n4)[nH]c3c2)CC1] |
| 30 | N-{4-[3-(1H-benzimidazol-2-yl)-1H-pyrazol-5-yl]phenyl}-N'-[4-chloro-3-(trifluoromethyl)phenyl]urea | 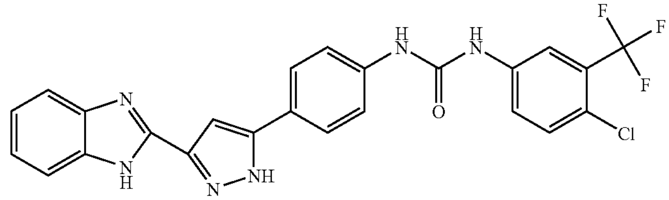 [SMILES: O=C(Nc1ccc(-c2cc(-c3nc4ccccc4[nH]3)n[nH]2)cc1)Nc1ccc(Cl)c(C(F)(F)F)c1] |
| 31 | N-{4-[3-(1H-benzimidazol-2-yl)-1H-pyrazol-5-yl]phenyl}-N'-[2-fluoro-5-(trifluoromethyl)phenyl]urea | 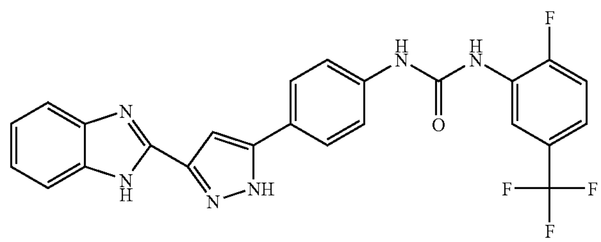 [SMILES: O=C(Nc1ccc(-c2cc(-c3nc4ccccc4[nH]3)n[nH]2)cc1)Nc1cc(C(F)(F)F)ccc1F] |
| 32 | N-(2,4-difluorophenyl)-N'-(4-{3-[5-(4-methylpiperazin-1-yl)-1H-benzimidazol-2-yl]-1H-pyrazol-5-yl}phenyl)urea | 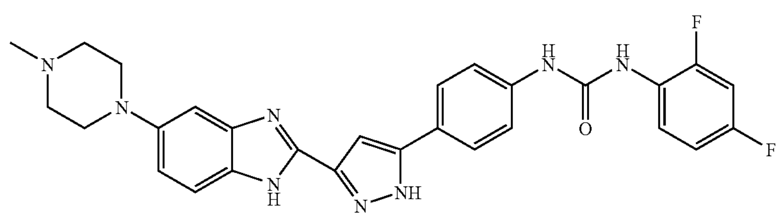 [SMILES: CN1CCN(c2ccc3[nH]c(-c4cc(-c5ccc(NC(=O)Nc6ccc(F)cc6F)cc5)[nH]n4)nc3c2)CC1] |
| 33 | N-{4-[3-(1H-benzimidazol-2-yl)-1H-pyrazol-5-yl]phenyl}-N'-phenylurea | 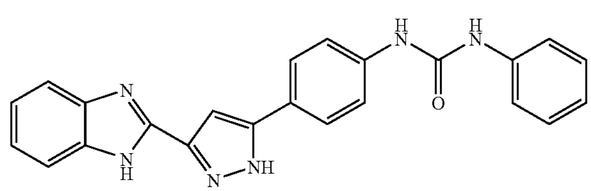 [SMILES: O=C(Nc1ccccc1)Nc1ccc(-c2cc(-c3nc4ccccc4[nH]3)n[nH]2)cc1] |
| 34 | N-[3,5-bis(trifluoromethyl)phenyl]-N'-(4-{3-[5-(4-methylpiperazin-1-yl)-1H-benzimidazol-2-yl]-1H-pyrazol-5-yl}phenyl)urea | 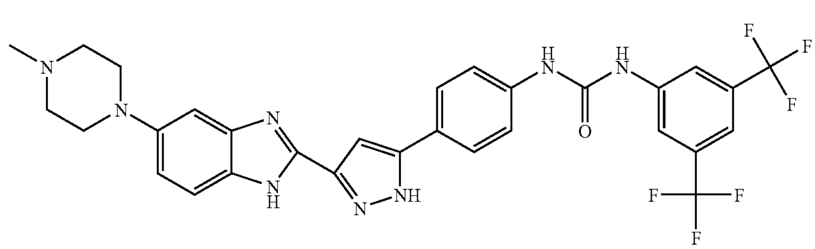 [SMILES: CN1CCN(c2ccc3[nH]c(-c4cc(-c5ccc(NC(=O)Nc6cc(C(F)(F)F)cc(C(F)(F)F)c6)cc5)[nH]n4)nc3c2)CC1] |

TABLE 1-continued

| Entry | Name | Structure |
|---|---|---|
| 35 | N-(2-fluorophenyl)-N'-(4-{3-[5-(4-methylpiperazin-1-yl)-1H-benzimidazol-2-yl]-1H-pyrazol-5-yl}phenyl)urea | 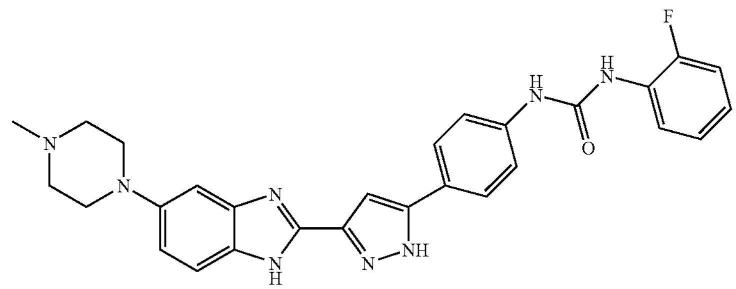 [SMILES: CN1CCN(c2ccc3[nH]c(-c4cc(-c5ccc(NC(=O)Nc6ccccc6F)cc5)[nH]n4)nc3c2)CC1] |
| 36 | 4-((E)-2-{5-[(E)-2-phenylethenyl]-1H-pyrazol-3-yl}ethenyl)phenol | 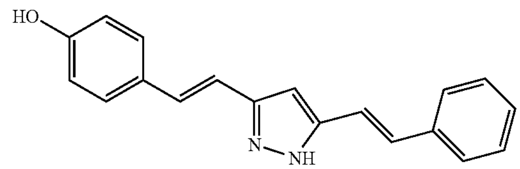 [SMILES: Oc1ccc(/C=C/c2cc(/C=C/c3ccccc3)[nH]n2)cc1] |
| 37 | 2-(methyloxy)-4-((E)-2-{5-[(E)-2-phenylethenyl]-1H-pyrazol-3-yl}ethenyl)phenol | 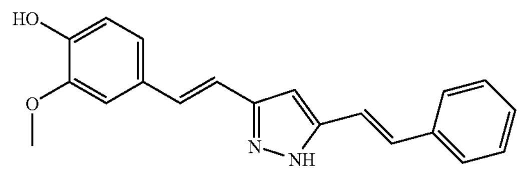 [SMILES: COc1cc(/C=C/c2cc(/C=C/c3ccccc3)[nH]n2)ccc1O] |
| 38 | N-(5-fluoro-2-methylphenyl)-N'-(4-{3-[6-(4-methylpiperazin-1-yl)-1H-benzimidazol-2-yl]-1H-pyrazol-5-yl}phenyl)urea | 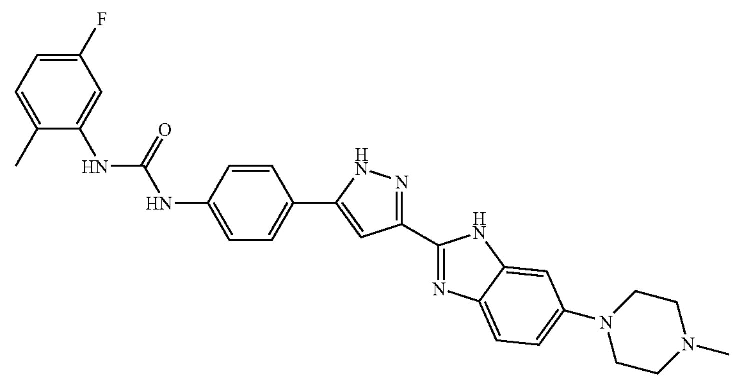 [SMILES: Cc1ccc(F)cc1NC(=O)Nc1ccc(-c2cc(-c3nc4ccc(N5CCN(C)CC5)cc4[nH]3)n[nH]2)cc1] |
| 39 | N-(4-{3-[5-(4-methylpiperazin-1-yl)-1H-benzimidazol-2-yl]-1H-pyrazol-5-yl}phenyl)-N'-phenylurea | 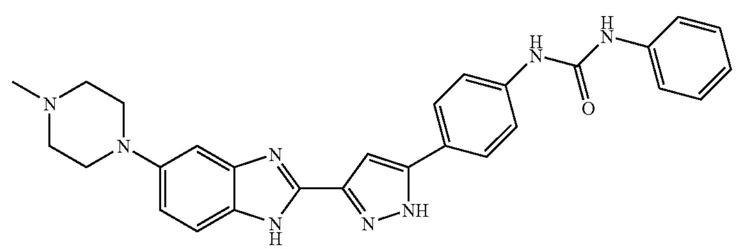 [SMILES: CN1CCN(c2ccc3[nH]c(-c4cc(-c5ccc(NC(=O)Nc6ccccc6)cc5)[nH]n4)nc3c2)CC1] |
| 40 | N-[4-chloro-3-(trifluoromethyl)phenyl]-N'-(4-{3-[3-(4-methylpiperazin-1-yl)phenyl]-1H-pyrazol-5-yl}phenyl)urea | 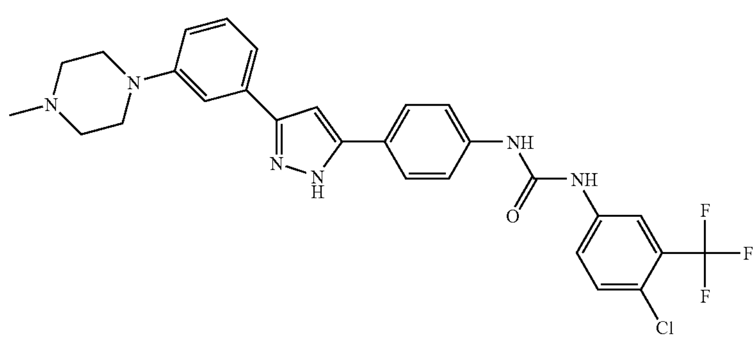 [SMILES: CN1CCN(c2cccc(-c3cc(-c4ccc(NC(=O)Nc5ccc(Cl)c(C(F)(F)F)c5)cc4)[nH]n3)c2)CC1] |

TABLE 1-continued

| Entry | Name | Structure |
|---|---|---|
| 41 | N-(2,4-difluorophenyl)-N'-(4-{3-[4-(4-methylpiperazin-1-yl)phenyl]-1H-pyrazol-5-yl}phenyl)urea | 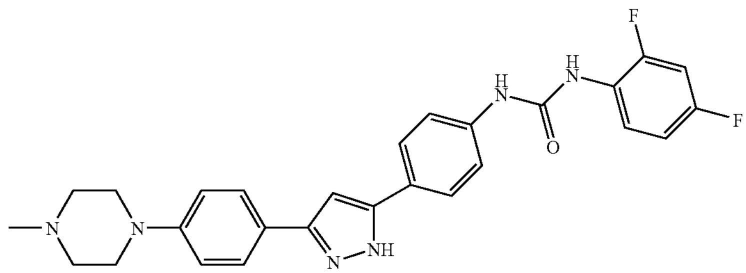 [SMILES: CN1CCN(c2ccc(-c3cc(-c4ccc(NC(=O)Nc5ccc(F)cc5F)cc4)[nH]n3)cc2)CC1] |
| 42 | N-(2,3-dihydro-1,4-benzodioxin-6-yl)-N'-(4-{5-[4-(4-methylpiperazin-1-yl)phenyl]-1H-pyrazol-3-yl}phenyl)urea | 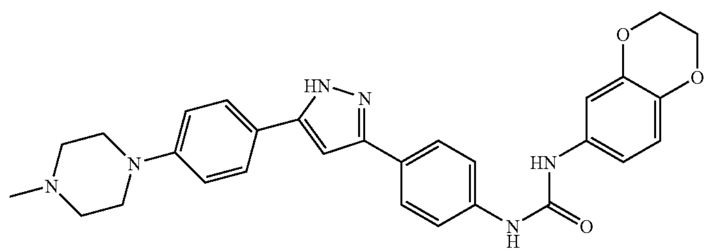 [SMILES: CN1CCN(c2ccc(-c3cc(-c4ccc(NC(=O)Nc5ccc6c(c5)OCCO6)cc4)n[nH]3)cc2)CC1] |
| 43 | N-[2,4-bis(methyloxy)phenyl]-N'-(4-{5-[4-(4-methylpiperazin-1-yl)phenyl]-1H-pyrazol-3-yl}phenyl)urea | 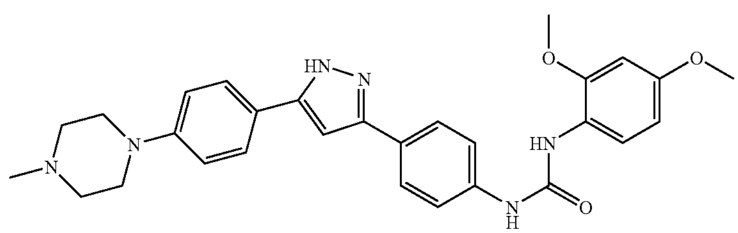 |
| 44 | 4-((E)-2-{3-[(E)-2-(4-fluorophenyl)ethenyl]-1H-pyrazol-5-yl}ethenyl)-2-(methyloxy)phenol | 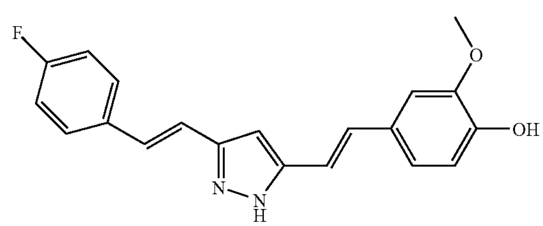 [SMILES: COc1cc(/C=C/c2cc(/C=C/c3ccc(F)cc3)n[nH]2)ccc1O] |
| 45 | 4-{(E)-2-[3-(1-benzofuran-2-yl)-1H-pyrazol-5-yl]ethenyl}phenol | 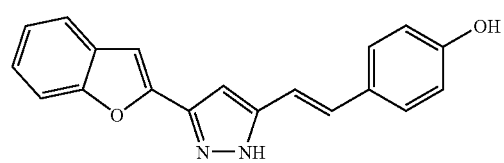 [SMILES: Oc1ccc(/C=C/c2cc(-c3cc4ccccc4o3)n[nH]2)cc1] |
| 46 | N-(4-{3-[4-(4-methylpiperazin-1-yl)phenyl]-1H-pyrazol-5-yl}phenyl)-N'-(2-phenylethyl)ethanediamide | 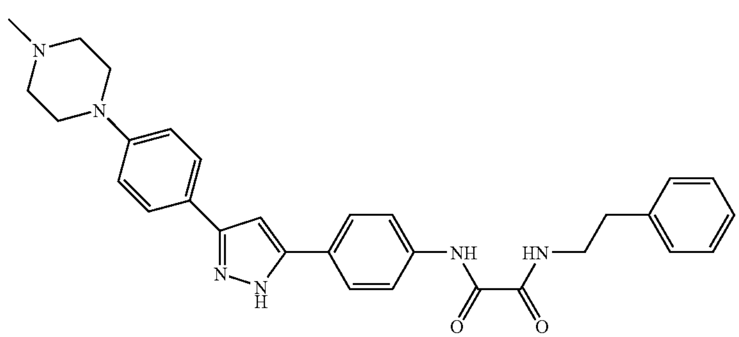 [SMILES: CN1CCN(c2ccc(-c3cc(-c4ccc(NC(=O)C(=O)NCCc5ccccc5)cc4)[nH]n3)cc2)CC1] |

TABLE 1-continued

| Entry | Name | Structure |
|---|---|---|
| 47 | 4-{(E)-2-[3-(1H-benzimidazol-2-yl)-1H-pyrazol-5-yl]ethenyl}phenol | 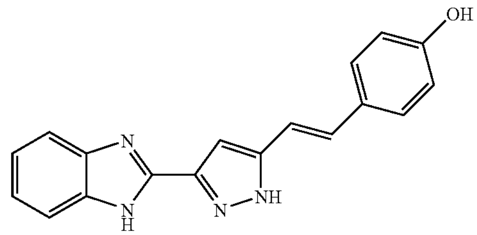 [SMILES: Oc1ccc(/C=C/c2cc(-c3nc4ccccc4[nH]3)n[nH]2)cc1] |
| 48 | 4-((E)-2-{3-[(E)-2-(4-chlorophenyl)ethenyl]-1H-pyrazol-5-yl}ethenyl)-2-(methyloxy)phenol | 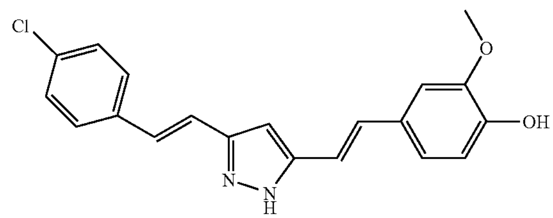 [SMILES: COc1cc(/C=C/c2cc(/C=C/c3ccc(Cl)cc3)n[nH]2)ccc1O] |
| 49 | 4-{(E)-2-[3-(1-benzothien-2-yl)-1H-pyrazol-5-yl]ethenyl}phenol | 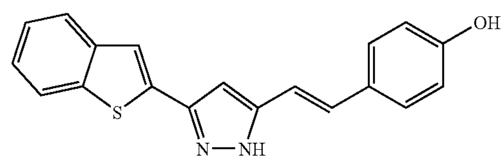 |
| 50 | N-[4-chloro-3-(trifluoromethyl)phenyl]-N'-[4-(3-phenyl-1H-pyrazol-5-yl)phenyl]urea | 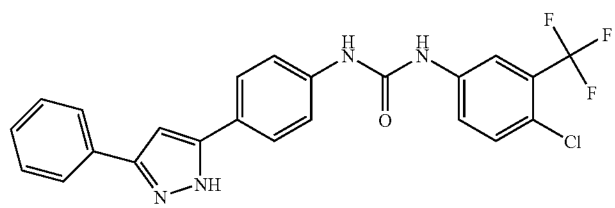 [SMILES: O=C(Nc1ccc(-c2cc(-c3ccccc3)n[nH]2)cc1)Nc1ccc(Cl)c(C(F)(F)F)c1] |
| 51 | 4-((E)-2-{3-[4-(4-methylpiperazin-1-yl)phenyl]-1H-pyrazol-5-yl}ethenyl)phenol | 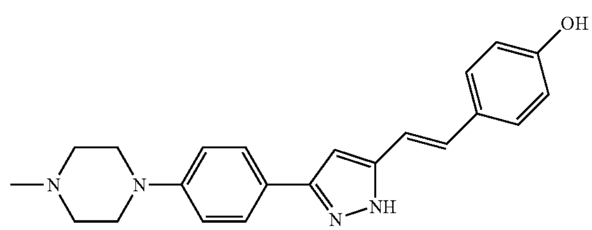 [SMILES: CN1CCN(c2ccc(-c3cc(/C=C/c4ccc(O)cc4)[nH]n3)cc2)CC1] |
| 52 | 1,1-dimethylethyl{4-[3-(1H-benzimidazol-2-yl)-1H-pyrazol-5-yl]phenyl}carbamate | 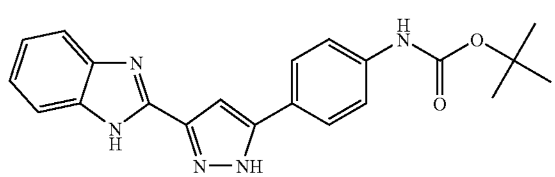 [SMILES: CC(C)(C)OC(=O)Nc1ccc(-c2cc(-c3nc4ccccc4[nH]3)n[nH]2)cc1] |
| 53 | N-(5-fluoro-2-methylphenyl)-N'-(4-{5-[4-(4-methylpiperazin-1-yl)phenyl]-1H-pyrazol-3-yl}phenyl)urea | 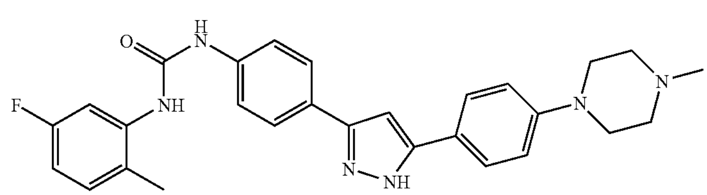 [SMILES: Cc1ccc(F)cc1NC(=O)Nc1ccc(-c2cc(-c3ccc(N4CCN(C)CC4)cc3)[nH]n2)cc1] |

TABLE 1-continued

| Entry | Name | Structure |
|---|---|---|
| 54 | 4-[(E)-2-(3-phenyl-1H-pyrazol-5-yl)ethenyl]phenol | 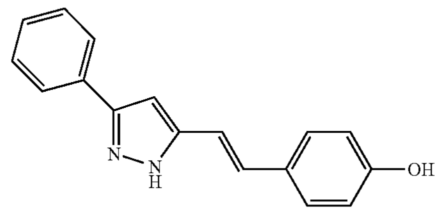 [SMILES: Oc1ccc(/C=C/c2cc(-c3ccccc3)n[nH]2)cc1] |
| 55 | 2-(methyloxy)-4-[(E)-2-(5-phenyl-1H-pyrazol-3-yl)ethenyl]phenol | 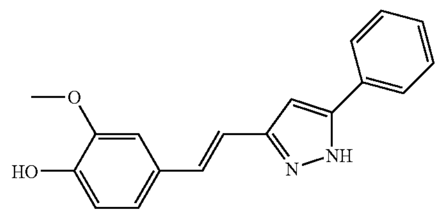 [SMILES: COc1cc(/C=C/c2cc(-c3ccccc3)[nH]n2)ccc1O] |
| 56 | 4-[(E)-2-(5-naphthalen-2-yl-1H-pyrazol-3-yl)ethenyl]phenol | 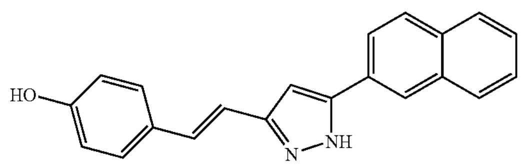 [SMILES: Oc1ccc(/C=C/c2cc(-c3ccc4ccccc4c3)[nH]n2)cc1] |
| 57 | 4-{(E)-2-[5-(2-fluorophenyl)-1H-pyrazol-3-yl]ethenyl}phenol | 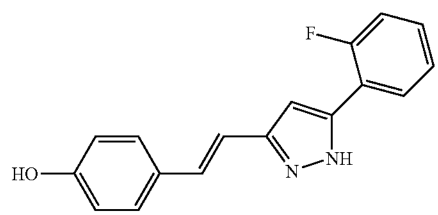 [SMILES: Oc1ccc(/C=C/c2cc(-c3ccccc3F)[nH]n2)cc1] |
| 58 | 4-((E)-2-{3-[3-(4-methylpiperazin-1-yl)phenyl]-1H-pyrazol-5-yl}ethenyl)phenol | 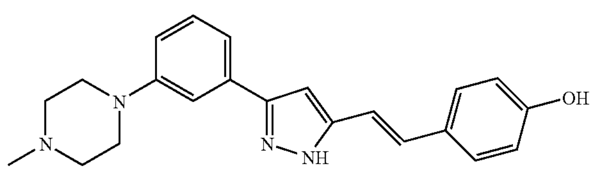 [SMILES: CN1CCN(c2cccc(-c3cc(/C=C/c4ccc(O)cc4)[nH]n3)c2)CC1] |
| 59 | 4-((E)-2-{3-[(E)-2-(2,4-difluorophenyl)ethenyl]-1H-pyrazol-5-yl}ethenyl)-2-(methyloxy)phenol | 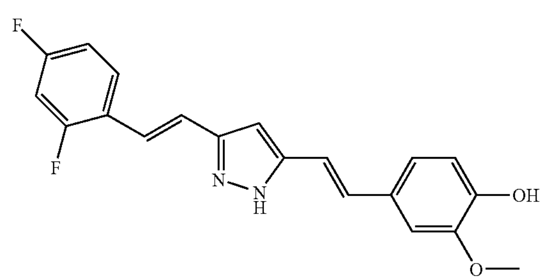 [SMILES: COc1cc(/C=C/c2cc(/C=C/c3ccc(F)cc3F)n[nH]2)ccc1O] |
| 60 | 4-{(E)-2-[5-(4-fluorophenyl)-1H-pyrazol-3-yl]ethenyl}phenol | 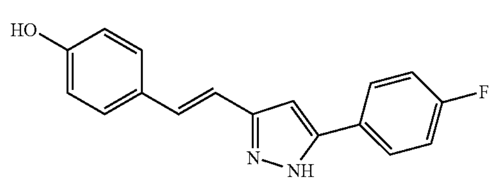 [SMILES: Oc1ccc(/C=C/c2cc(-c3ccc(F)cc3)[nH]n2)cc1] |

TABLE 1-continued

| Entry | Name | Structure |
|---|---|---|
| 61 | 4-{(E)-2-[3-(4-chlorophenyl)-1H-pyrazol-5-yl]ethenyl}phenol | 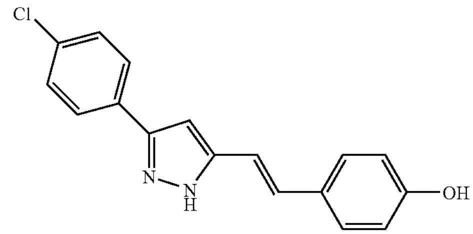 [SMILES: Oc1ccc(/C=C/c2cc(-c3ccc(Cl)cc3)n[nH]2)cc1] |
| 62 | 4-[(E)-2-(5-pyridin-2-yl-1H-pyrazol-3-yl)ethenyl]phenol | 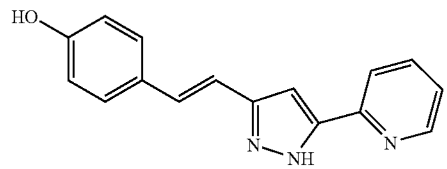 [SMILES: Oc1ccc(/C=C/c2cc(-c3ccccn3)[nH]n2)cc1] |
| 63 | 4-{(E)-2-[3-(5-chloro-1-benzofuran-2-yl)-1H-pyrazol-5-yl]ethenyl}phenol | 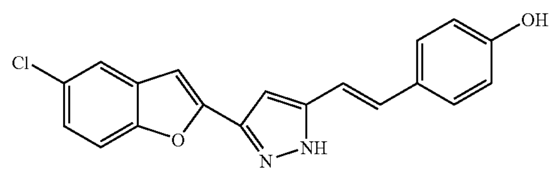 [SMILES: Oc1ccc(/C=C/c2cc(-c3cc4cc(Cl)ccc4o3)n[nH]2)cc1] |
| 64 | N-(1,1-dimethylethyl)-N'-(4-{3-[5-(4-ethylpiperazin-1-yl)-1H-benzimidazol-2-yl]-1H-pyrazol-5-yl}phenyl)urea | 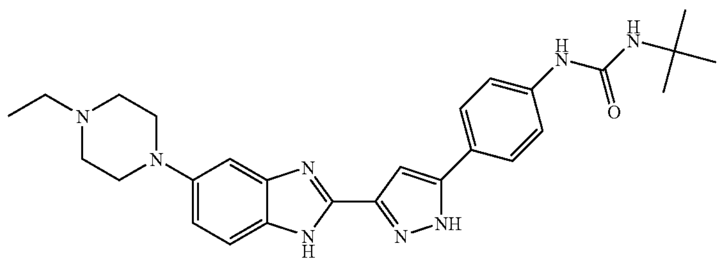 [SMILES: CCN1CCN(c2ccc3[nH]c(-c4cc(-c5ccc(NC(=O)NC(C)(C)C)cc5)[nH]n4)nc3c2)CC1] |
| 65 | 4-[(E)-2-(3-pyridin-4-yl-1H-pyrazol-5-yl)ethenyl]phenol | 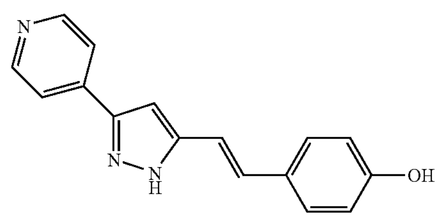 [SMILES: Oc1ccc(/C=C/c2cc(-c3ccncc3)n[nH]2)cc1] |
| 66 | 4-{(E)-2-[3-(3-chlorophenyl)-1H-pyrazol-5-yl]ethenyl}phenol | 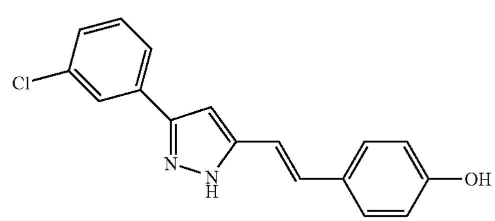 [SMILES: Oc1ccc(/C=C/c2cc(-c3cccc(Cl)c3)n[nH]2)cc1] |
| 67 | 4-((E)-2-{5-[2-(methyloxy)phenyl]-1H-pyrazol-3-yl}ethenyl)phenol | 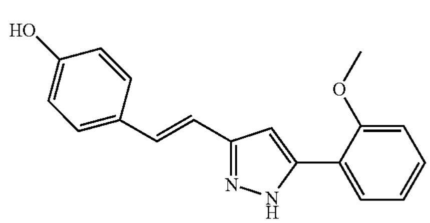 [SMILES: COc1ccccc1-c1cc(/C=C/c2ccc(O)cc2)n[nH]1] |

TABLE 1-continued

| Entry | Name | Structure |
|---|---|---|
| 68 | 4-{(E)-2-[3-(2-chlorophenyl)-1H-pyrazol-5-yl]ethenyl}phenol | 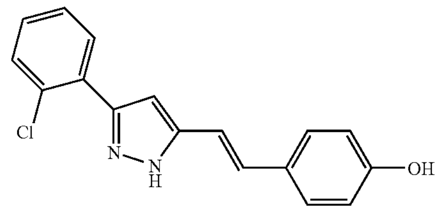 [SMILES: Oc1ccc(/C=C/c2cc(-c3ccccc3Cl)n[nH]2)cc1] |
| 69 | 4-[(E)-2-(3-pyridin-3-yl-1H-pyrazol-5-yl)ethenyl]phenol | 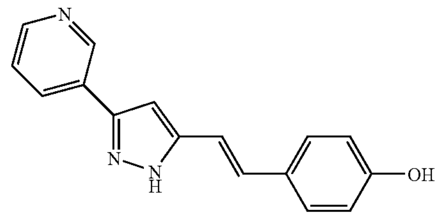 [SMILES: Oc1ccc(/C=C/c2cc(-c3cccnc3)n[nH]2)cc1] |
| 70 | 4-((E)-2-{5-[3-(methyloxy)phenyl]-1H-pyrazol-3-yl}ethenyl)phenol | 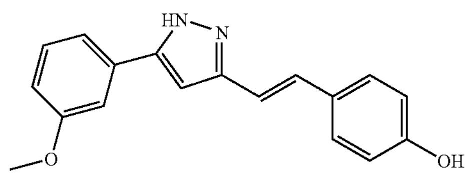 [SMILES: COc1cccc(-c2cc(/C=C/c3ccc(O)cc3)n[nH]2)c1] |
| 71 | 1,1-dimethylethyl(4-{3-[(E)-2-phenylethenyl]-1H-pyrazol-5-yl}phenyl)carbamate | 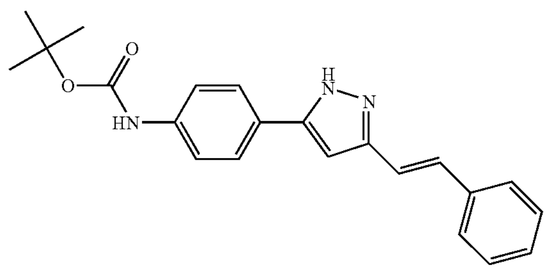 [SMILES: CC(C)(C)OC(=O)Nc1ccc(-c2cc(/C=C/c3ccccc3)n[nH]2)cc1] |
| 72 | 4-{(E)-2-[3-(3,4-dichlorophenyl)-1H-pyrazol-5-yl]ethenyl}phenol | 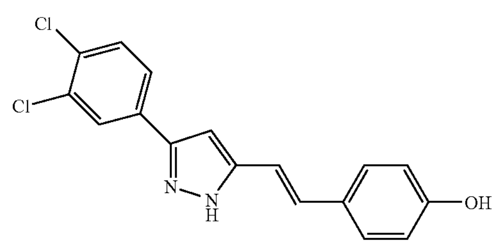 [SMILES: Oc1ccc(/C=C/c2cc(-c3ccc(Cl)c(Cl)c3)n[nH]2)cc1] |
| 73 | 2-{5-[(E)-2-phenylethenyl]-1H-pyrazol-3-yl}-1-benzofuran-6-ol | 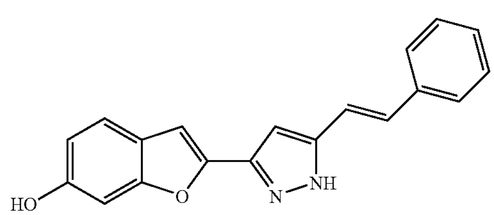 [SMILES: Oc1ccc2cc(-c3cc(/C=C/c4ccccc4)[nH]n3)oc2c1] |
| 74 | 4-{(E)-2-[5-(3-fluorophenyl)-1H-pyrazol-3-yl]ethenyl}phenol | 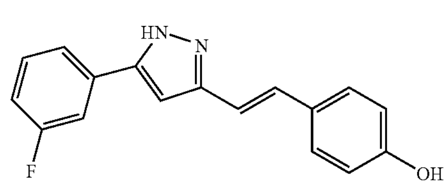 [SMILES: Oc1ccc(/C=C/c2cc(-c3cccc(F)c3)[nH]n2)cc1] |

TABLE 1-continued

| Entry | Name | Structure |
|---|---|---|
| 75 | 2-(5-phenyl-1H-pyrazol-3-yl)-1H-benzimidazole | 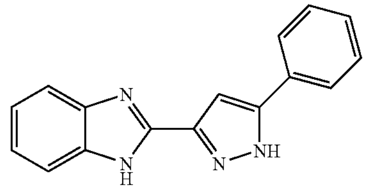 [SMILES: c1ccc(-c2cc(-c3nc4ccccc4[nH]3)n[nH]2)cc1] |
| 76 | N-phenyl-N'-[4-(3-phenyl-1H-pyrazol-5-yl)phenyl]urea | 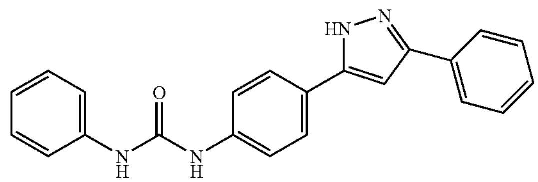 [SMILES: O=C(Nc1ccccc1)Nc1ccc(-c2cc(-c3ccccc3)n[nH]2)cc1] |
| 77 | 4-[3-(1H-benzimidazol-2-yl)-1H-pyrazol-5-yl]aniline | 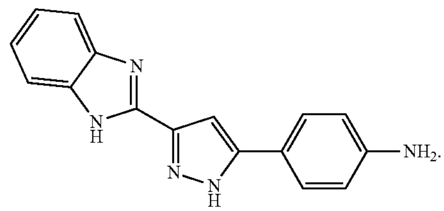 [SMILES: Nc1ccc(-c2cc(-c3nc4ccccc4[nH]3)n[nH]2)cc1] |
| 78 | 4-[(E)-2-(5-biphenyl-3-yl-1H-pyrazol-3-yl)ethenyl]phenol | 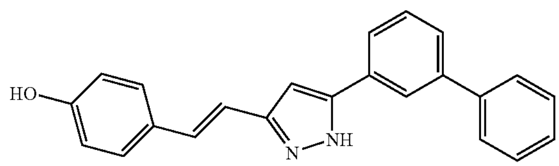 [SMILES: Oc1ccc(/C=C/c2cc(-c3cccc(-c4ccccc4)c3)[nH]n2)cc1] |
| 79 | 4-((E)-2-{5-[5-(4-methylpiperazin-1-yl)-1H-benzimidazol-2-yl]-1H-pyrazol-3-yl}ethenyl)phenol | 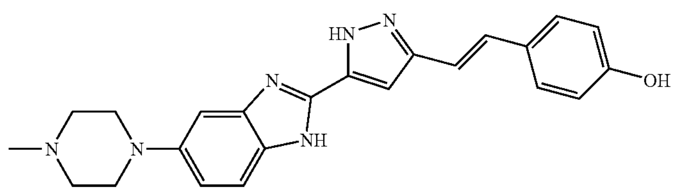 [SMILES: CN1CCN(c2ccc3[nH]c(-c4cc(/C=C/c5ccc(O)cc5)n[nH]4)nc3c2)CC1] |

Another aspect of the invention is a pharmaceutical composition comprising the compound according to any one of paragraphs [0023]-[0063] and a pharmaceutically acceptable carrier.

Another aspect of the invention is a metabolite of the compound or the pharmaceutical composition according to any one of paragraphs [0023]-[0064].

Another aspect of the invention is a method of modulating the in vivo activity of a kinase, the method comprising administering to a subject an effective amount of a composition comprising at least one of the compound according to any of paragraphs [0023]-[0063] and the pharmaceutical composition according to paragraph [0064].

Another aspect of the invention is the method according to paragraph [0066], wherein the kinase is selected from c-Kit and flt-3.

Another aspect of the invention is the method according to paragraph [0067], wherein modulating the in vivo activity of said kinase comprises inhibition of said kinase.

Another aspect of the invention is a method of treating diseases or disorders associated with uncontrolled, abnormal, and/or unwanted cellular activities, the method comprising administering, to a mammal in need thereof, a therapeutically effective amount of a composition comprising at least one of the compound according to any of paragraphs [0023]-[0063] and the pharmaceutical composition according to paragraph [0064].

Another aspect of the invention is a method of screening for modulator of a kinase, the method comprising combining either a composition comprising at least one of the compound according to any of paragraphs [0023]-[0063] and the pharmaceutical composition according to paragraph [0064], and at least one candidate agent and determining the effect of the candidate agent on the activity of said kinase.

Another aspect of the invention is a method of inhibiting proliferative activity in a cell or a plurality of cells, the method comprising administering an effective amount of at least one of the compound according to any of paragraphs [0023]-[0063] and the pharmaceutical composition according to paragraph [0064] to said cell or plurality of cells.

Definitions

As used in the present specification, the following words and phrases are generally intended to have the meanings as set forth below, except to the extent that the context in which they are used indicates otherwise or they are expressly defined to mean something different.

The symbol "—" means a single bond, "═" means a double bond, "≡" means a triple bond. The symbol "⌇" refers to a group on a double-bond as occupying either position on the terminus of a double bond to which the symbol is attached; that is, the geometry, E- or Z-, of the double bond is ambiguous. When a double bond is depicted in textual format, for example —C(H)═C(H)—, then this is meant to construe both E- and Z-geometries. When a group is depicted removed from its parent formula, the "~" symbol will be used at the end of the bond which was theoretically cleaved in order to separate the group from its parent structural formula.

Chemical formulae use descriptors such as "$R^1$" accompanied by a list of formulae or verbage describing the scope of what is meant by the descriptor. A subsequent descriptor such as "$R^{1a}$" is used to describe some subset of the scope of $R^1$, and "$R^{1b}$" is used to describe another subset of the scope of $R^1$, and so on. In such subsequent cases, all other formulae containing simply "$R^1$" are meant to include the entire scope of the descriptor.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

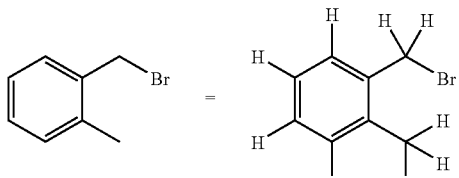

In this application, some ring structures are depicted generically and will be described textually. For example, in the schematic below, if in the structure on the left, ring A is used to describe a "spirocyclyl," then if ring A is cyclopropyl, there are at most four hydrogens on ring A (when "R" can also be —H). In another example, as depicted on the right side of the schematic below, if ring B is used to describe a "phenylene" then there can be at most four hydrogens on ring B (assuming depicted cleaved bonds are not C—H bonds).

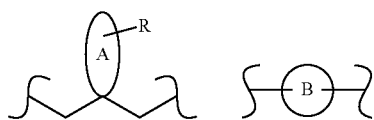

If a group "W" is depicted as "floating" on a ring system, as for example in the formula:

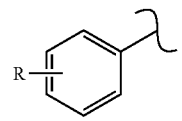

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

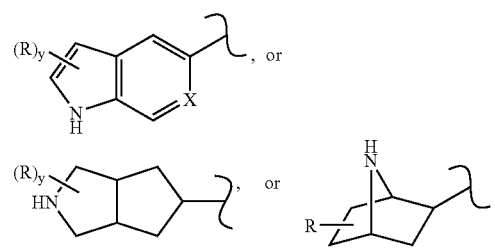

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "X" equals ═CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When a group "R" is depicted as existing on a ring system containing saturated carbons, as for example in the formula:

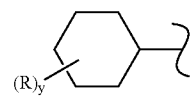

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

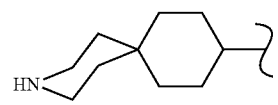

"Alkyl" is intended to include linear, branched, or cyclic hydrocarbon structures and combinations thereof, inclusively. For example, "$C_8$ alkyl" may refer to an n-octyl, iso-octyl, cyclohexylethyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more that eight carbon atoms. Exemplary alkyl groups are those of $C_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus, when an alkyl residue having a specific number of carbons is named, all geometric isomers having that number of carbons are intended to be encompassed; thus, for example, either "butyl" or "$C_4$alkyl" is meant to include n-butyl, sec-butyl, isobutyl, t-butyl, isobutenyl and but-2-yne radicals; and for example, "propyl" or "$C_3$alkyl" each include n-propyl, propenyl, and isopropyl. Otherwise, if alkenyl and/or alkynyl descriptors are used in a particular definition of a group, for example "$C_4$alkyl" along "$C_4$alkenyl," then $C_4$alkenyl geometric isomers are not meant to be included in "$C_4$alkyl," but other 4-carbon isomers are, for example $C_4$alkynyl. For example, a more general description, intending to encompass the invention as a whole may describe a particular group as "$C_{1-8}$alkyl" while a preferred species may describe the same group as including, "$C_{1-8}$alkyl," "$C_{1-6}$alkenyl" and "$C_{1-5}$alkynyl."

"Alkylene" refers to straight or branched chain divalent radical consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), and cyclohexylpropylene (—$CH_2CH_2CH(C_6H_{13})$).

"Alkylidene" refers to a straight or branched chain unsaturated divalent radical consisting solely of carbon and hydrogen atoms, having from two to ten carbon atoms, for example, ethylidene, propylidene, n-butylidene, and the like. Alkylidene is a subset of alkyl, referring to the same residues as alkyl, but having two points of attachment and, specifically, double bond unsaturation. The unsaturation present includes at least one double bond.

"Alkylidyne" refers to a straight or branched chain unsaturated divalent radical consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above radicals, "alkylene," "alkylidene" and "alkylidyne," when optionally substituted, may contain alkyl substitution which itself contains unsaturation. For example, 2-(2-phenylethynyl-but-3-enyl)-haphthalene (IUPAC name) contains an n-butylid-3-ynyl radical with a vinyl substituent at the 2-position of said radical.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Substituted alkoxy" refers to the group —O-(substituted alkyl), the substitution on the alkyl group generally containing more than only carbon (as defined by alkoxy). One exemplary substituted alkoxy group is "polyalkoxy" or —O-optionally substituted alkylene-optionally substituted alkoky, and includes groups such as —$OCH_2CH_2OCH_3$, and glycol ethers such as polyethyleneglycol and —$O(CH_2CH_2O)_xCH_3$, where x is an integer of between about two and about twenty, in another example, between about two and about ten, and in a further example between about two and about five. Another exemplary substituted alkoxy group is hydroxyalkoxy or —$OCH_2(CH_2)_yOH$, where y is for example an integer of between about one and about ten, in another example y is an integer of between about one and about four.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons.

"α-Amino Acids" refer to naturally occurring and commercially available amino acids and optical isomers thereof. Typical natural and commercially available α-amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), and the like.

"Amino" refers to the group —$NH_2$. "Substituted amino," refers to the group —N(H)R or —N(R)R where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, for example, diethylamino, methylsulfonylamino, and furanyl-oxy-sulfonamino.

"Aryl" refers to aromatic six- to fourteen-membered carbocyclic ring, for example, benzene, naphthalene, indane, tetralin, fluorene and the like, univalent radicals. As univalent radicals, the aforementioned ring examples are named, phenyl, naphthyl, indanyl, tetralinyl, and fluorenyl.

"Arylene" generically refers to any aryl that has at least two non-hydrogen groups attached thereto. For a more specific example, "phenylene" refers to a divalent phenyl ring radical. A phenylene, thus may have more than two groups attached, but is defined by a minimum of two non-hydrogen groups attached thereto. The terms "ortho-arylene," "meta-arylene" or "para-arylene" refer to geometrical isomers of a particular arylene wherein, two groups attached to an aryl as depicted in a formula are situated in an ortho, meta or para geometrical relationship about the aryl, respectively.

"Arylalkyl" refers to a residue in which an aryl moiety is attached to a parent structure via one of an alkylene, alkylidene, or alkylidyne radical. Examples include benzyl, phenethyl, phenylvinyl, phenylallyl and the like. Both the aryl, and the corresponding alkylene, alkylidene, or alkylidyne radical portion of an arylalkyl group may be optionally substituted. "Lower arylalkyl" refers to an arylalkyl where the "alkyl" portion of the group has one to six carbons; this can also be refered to as aryl $C_{1-6}$alkyl.

"Exo-alkenyl" refers to a double bond that emanates from an annular carbon, and is not within the ring system, for example the double bond depicted in the formula below.

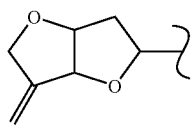

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl radicals that are substituted with one or more halogens, respectively. Thus, "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroarylene" generically refers to any heteroaryl that has at least two groups attached thereto. For a more specific example, "pyridylene" refers to a divalent pyridyl ring radical. A pyridylene, thus may have more than two groups attached, but is defined by a minimum of two non-hydrogen groups attached thereto. For the purposes of this application, the term "ortho-heteroarylene" refers to a geometrical isomer of a particular heteroarylene wherein two groups attached to a heteroaryl as depicted in a formula are situated on contiguous atoms of the heteroaryl.

"Heteroatom" refers to O, S, N, or P.

"Heterocyclyl" refers to a stable three- to fifteen-membered ring radical that consists of carbon atoms and from one to five heteroatoms selected from the group consisting of nitrogen, phosphorus, oxygen and sulfur. For purposes of this invention, the heterocyclyl radical may be a monocyclic, bicyclic or tricyclic ring system, which may include fused or bridged ring systems as well as spirocyclic systems; and the nitrogen, phosphorus, carbon or sulfur atoms in the heterocyclyl radical may be optionally oxidized to various oxidation states. In a specific example, the group —$S(O)_{0-2}$—, refers to —S— (sulfide), —S(O)— (sulfoxide), and —$SO_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring radical may be partially or fully saturated or aromatic. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, pthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzpyrazolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl radical. A heteroalicyclic may contain unsaturation, but is not aromatic.

"Heteroaryl" refers specifically to an aromatic heterocyclyl radical.

"Heterocyclylalkyl" refers to a residue in which a heterocyclyl is attached to a parent structure via one of an alkylene, alkylidene, or alkylidyne radical. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl and the corresponding alkylene, alkylidene, or alkylidyne radical portion of a heterocyclylalkyl group may be optionally substituted. "Lower heterocyclylalkyl" refers to a heterocyclylalkyl where the "alkyl" portion of the group has one to six carbons. "Heteroalicyclylalkyl" refers specifically to a heterocyclylalkyl where the heterocyclyl portion of the group is non-aromatic; and "heteroarylalkyl" refers specifically to a heterocyclylalkyl where the heterocyclyl portion of the group is aromatic. Such terms may be described in more than one way, for example, "lower heterocyclylalkyl" and "heterocyclyl $C_{1-6}$alkyl" are equivalent terms.

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substituents, that only sterically practical and/or synthetically feasible compounds are meant to be included. "Optionally substituted" refers to all subsequent modifiers in a term, for example in the term "optionally substituted aryl $C_{1-8}$alkyl," optional substitution may occur on both the "$C_{1-8}$alkyl" portion and the "aryl" portion of the molecule; and for example, optionally substituted alkyl includes optionally substituted cycloalkyl groups, which in turn are defined as including optionally substituted alkyl groups, potentially ad infinitum. A list of exemplary optional substitutions is included below in the definition of "substituted."

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system.

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

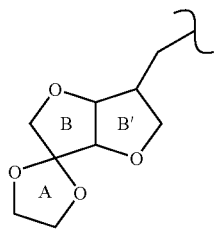

"Substituted" alkyl, aryl, and heterocyclyl, refer respectively to alkyl, aryl, and heterocyclyl, wherein one or more (for example up to about five, in another example, up to about three) hydrogen atoms are replaced by a substituent independently selected from: optionally substituted alkyl (for example, fluoromethyl, hydroxypropyl, nitromethyl, aminoethyl and the like.), optionally substituted aryl (for example, 4-hydroxyphenyl, 2,3-difluorophenyl, and the like), optionally substituted arylalkyl (for example, 1-phenyl-ethyl, para-methoxyphenylethyl and the like), optionally substituted heterocyclylalkyl (for example, 1-pyridin-3-yl-ethyl, N-ethylmorphonlino and the like), optionally substituted heterocyclyl (for example, 5-chloro-pyridin-3-yl, 1-methyl-piperidin-4-yl and the like), optionally substituted alkoxy (for example methoxyethoxy, hydroxypropyloxy, methylenedioxy and the like), optionally substituted amino (for example, methylamino, diethylamino, trifluoroacetylamino and the like), optionally substituted amidino, optionally substituted aryloxy (for example, phenoxy, para-chlorophenoxy, meta-aminophenoxy, para-phenoxyphenoxy and the like), optionally substituted arylalkyloxy (for example, benzyloxy, 3-chlorobenzyloxy, meta-phenoxybenzyloxy and the like), carboxy (—$CO_2H$), optionally substituted carboalkoxy (that is, acyloxy or —OC(=O)R), optionally substituted carboxyalkyl (that is, esters or —$CO_2R$), optionally substituted carboxamido, optionally substituted benzyloxycarbonylamino (CBZ-amino), cyano, optionally substituted acyl, halogen, hydroxy, nitro, optionally substituted alkylsulfanyl, optionally substituted alkylsulfinyl, optionally substituted alkylsulfonyl, thiol, oxo, carbamyl, optionally substituted acylamino, optionally substituted hydrazino, optionally substituted hydroxylamino, and optionally substituted sulfonamido.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —$S(O_2)$—H, —$S(O_2)$-(optionally substituted alkyl), —$S(O_2)$-optionally substituted aryl), —$S(O_2)$-(optionally substituted heterocyclyl), —$S(O_2)$-(optionally substituted alkoxy), —$S(O_2)$-optionally substituted aryloxy), and —$S(O_2)$-(optionally substituted heterocyclyloxy).

"Yield" for each of the reactions described herein is expressed as a percentage of the theoretical yield.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS).

Tautomers. As known to one of ordinary skill in the art, compounds can exist in tautomeric forms. Of particular relevance to this invention is the possibility of tautomeric forms of pyrazoles, benzimidazoles, and 1,3-diketones, for example. An exemplary depiction of pyrazole tautomerism is shown below.

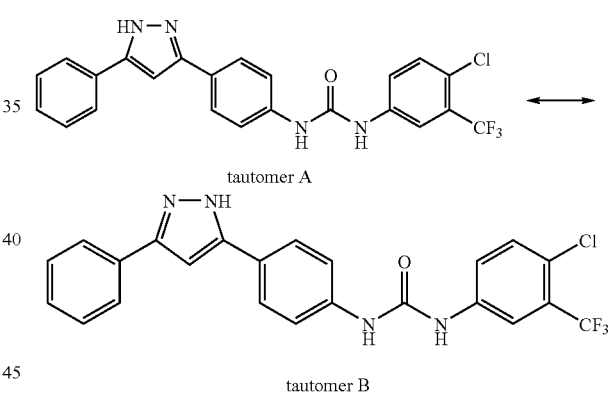

In this application, a compound may be drawn in a particular tautomeric form for illustrative purposes, however such illustrations are meant to include all tautomeric forms. Note, the tautomeric form in which a compound is drawn also determines, for example, the IUPAC name of the compound. As depicted above, tautomers A and B have different IUPAC names (other naming schemes may also generate distinct names for particular tautomers). Under the IUPAC system, tautomer A is N-[4-chloro-3-(trifluoromethyl)phenyl]-N'-[4-(5-phenyl-1H-pyrazol-3-yl)phenyl]urea, and tautomer B is N-[4-chloro-3-(trifluoro-methyl)phenyl]-N-[4-(3-phenyl-1H-pyrazol-5-yl)phenyl]urea. One of ordinary skill in the art would understand that these names (and tautomeric representations) are meant to describe the same compound.

The tautomer/name issue is seemingly more complex when various parts of a molecule each have possible tautomers. For example the compound depicted below (a compound of the invention) has four different tautomeric forms each with a corresponding unique IUPAC name. The compound, depending on how its pyrazole and benzimidazole moiety tautomers are drawn, can be named as N-[4-chloro-3-(trifluoromethyl)phenyl]-N'-(4-{5-[6-(4-methylpiperazin-1-yl)-1H-benzimidazol-2-yl]-1H-pyrazol-3-yl}phenyl)urea, N-[4-chloro-3-(trifluoromethyl)phenyl]-N'-(4-{5-[5-(4-methylpiperazin-1-yl)-1H-benzimidazol-2-yl]-1H-pyrazol-3-yl}phenyl)urea, N-[4-chloro-3-(trifluoromethyl)phenyl]-N'-(4-{3-[6-(4-methyl-piperazin-1-yl)-1H-benzimidazol-2-yl]-1H-pyrazol-5-yl}phenyl)urea or N-[4-chloro-3-(trifluoromethyl)phenyl]-N'-(4-{3-[5-(4-methylpiperazin-1-yl)-1H-benzimidazol-2-yl]-1H-pyrazol-5-yl}phenyl)urea. Thus in this description, particular tautomeric illustrations and names are used for convenience purposes. Such illustrations and names are meant to include all tautomeric forms of the particular molecule indicated tion or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major

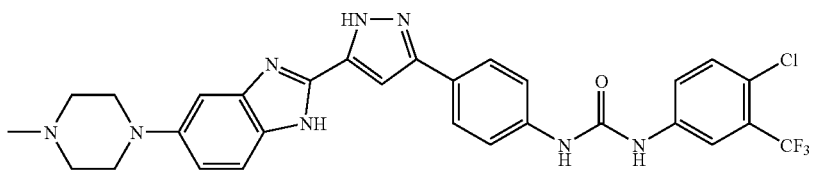 [SMILES: CN1CCN(c2ccc3[nH]c(-c4cc(-c5ccc(NC(=O)Nc6ccc(Cl)c(C(F)(F)F)c6)cc5)n[nH]4)nc3c2)CC1]

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that there can theoretically be some constructs which would not normally be considered as stable compounds (that is, sterically practical and/or synthetically feasible, supra).

When a particular group with its bonding structure is denoted as being bonded to two partners; that is, a divalent radical, for example, —OCH$_2$—, then it is understood that either of the two partners may be bound to the particular group at one end, and the other partner is necessarily bound to the other end of the particular group, unless stated explicitly otherwise. Stated another way, divalent radicals are not to be construed as limited to the depicted orientation, for example "—OCH$_2$—" is meant to mean not only "—OCH$_2$—" as drawn, but also "—CH$_2$O—."

Methods for the preparation and/or separation and isolation of single stereoisomers from racemic mixtures or non-racemic mixtures of stereoisomers are well known in the art. For example, optically active (R)— and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidacomponent enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma [pinealoma], glioblastorna multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma, vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal lands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucainine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was under-taken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

One of ordinary skill in the art would understand that certain crystallized, protein-ligand complexes, in particular c-Kit and flt-3-ligand complexes, and their corresponding x-ray structure coordinates can be used to reveal new structural information useful for understanding the biological activity of kinases as described herein. As well, the key structural features of the aforementioned proteins, particularly the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods may be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one of ordinary skill in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one of ordinary skill in the art would appreciate that compounds of the invention can be used in a method of evaluating the ability of a test agent to associate with a molecule or molecular complex comprising a ligand-binding domain of a kinase. Such a method may be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or, carrier) such as sodium citrate or, dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Utility of Compounds of the Invention as Screening Agents

To employ the compounds of the invention in a method of screening for candidate agents that bind to, for example c-Kit or flt-3 receptor kinase, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, c-Kit or flt-3 protein may be done in a number of ways. In one example, the candidate agent (the compound of the invention) is labeled, for example, with a fluorescent or radioactive moiety and binding determined directly. For example, thus may be done by attaching all or a portion of the c-Kit or flt-3 protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, for example, radioisotope, fluorescent tag, enzyme, antibodies, particles such as magnetic particles, chemiluminescent tag, or specific binding molecules, and the like. Specific binding molecules include pairs, such as biotin and streptavidin, digoxin and antidigoxin, and the like. For the specific binding members, the complementary member would normally be labeled with a molecule which provides for detection, in accordance with known procedures, as outlined above. The label can directly or indirectly provide a detectable signal.

In some embodiments, only one of the components is labeled. For example, c-Kit or flt-3 protein may be labeled at tyrosine positions using $^{125}$I, or with fluorophores. Alternatively, more than one component may be labeled with different labels; using $^{125}$I for the proteins, for example, and a fluorophor for the candidate agents.

The compounds of the invention may also be used as competitors to screen for additional drug candidates. "candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to c-Kit or flt-3.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to c-Kit or flt-3, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to c-Kit or flt-3 protein for a time sufficient to allow binding, if present. Incubations may be performed at any temperature that facilitates optimal activity, typically between 4° C. and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to c-Kit or flt-3 and thus is capable of binding to, and potentially modulating, the activity of the c-Kit or flt-3. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to c-Kit or flt-3 with a higher affinity. Thus, if the candidate agent is labeled, the presence of the label on the support, coupled with a lack of competitor binding, may indicate the candidate agent is capable of binding to c-Kit or flt-3.

It may be of value to identify the binding site of c-Kit or flt-3. This can be done in a variety of ways. In one embodiment, once c-Kit or flt-3 has been identified as binding to the candidate agent, the c-Kit or flt-3 is fragmented or modified and the assays repeated to identify the necessary components for binding.

Modulation is tested by screening for candidate agents capable of modulating the activity of c-Kit or flt-3 comprising the steps of combining a candidate agent with c-Kit or flt-3, as above, and determining an alteration in the biological activity of the c-Kit or flt-3. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening may be used to identify drug candidates that bind to native c-Kit or flt-3, but cannot bind to modified c-Kit or flt-3.

Positive controls and negative controls can be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components can be added in any order that provides for the requisite binding.

Abbreviations and Their Definitions

The following abbreviations and terms have the indicated meanings throughout:

| Abbreviation | Meaning |
|---|---|
| Ac | acetyl |
| ACN | acetonitrile |
| ATP | adenosine triphosphate |
| BNB | 4-bromomethyl-3-nitrobenzoic acid |
| Boc | t-butyloxy carbonyl |
| br | broad |
| Bu | butyl |
| °C. | degrees Celsius |
| c- | cyclo |
| CBZ | CarboBenZoxy = benzyloxycarbonyl |
| d | doublet |
| dd | doublet of doublet |
| dt | doublet of triplet |
| DBU | Diazabicyclo[5.4.0]undec-7-ere |
| DCM | dichloromethane = methylene chloride = $CH_2Cl_2$ |
| DCE | dichloroethylene |
| DEAD | diethyl azodicarboxylate |
| DIC | diisopropylcarbodiimide |
| DIEA | N,N-diisopropylethyl amine |
| DMAP | 4-N,N-dimethylaminopyridine |
| DMF | N,N-dimethylfonnamide |
| DMSO | dimethyl sulfoxide |
| DVB | 1,4-divinylbenzene |
| EEDQ | 2-ethoxy-1-ethoxycarbonyl-1,2-dihydroquinoline |
| EI | Electron Impact ionization |
| Et | ethyl |
| Fmoc | 9-fluorenylmethoxycarbonyl |
| g | gram(s) |
| GC | gas chromatography |
| h or hr | hour(s) |
| HATU | O-(7-Azabenzotriazol-1-yl)-1,1,3,3-tetramethyluronium hexafluorophosphate |
| HMDS | hexamethyldisilazane |
| HOAc | acetic acid |
| HOBt | hydroxybenzotriazole |
| HPLC | high pressure liquid chromatography |
| L | liter(s) |
| M | molar or molarity |
| m | multiplet |
| Me | methyl |
| mesyl | methanesulfonyl |
| mg | milligram(s) |
| MHz | megahertz (frequency) |
| Min | minute(s) |
| mL | milliliter(s) |
| mM | millimolar |
| mmol | millimole(s) |
| mol | mole(s) |
| MS | mass spectral analysis |
| MTBE | methyl t-butyl ether |
| N | normal or normality |
| NBS | N-bromosuccinimide |
| NCS | N-chlorosuccinimide |

-continued

| Abbreviation | Meaning |
|---|---|
| nM | nanomolar |
| NMO | N-methylmorpholine oxide |
| NMR | nuclear magnetic resonance spectroscopy |
| PEG | polyethylene glycol |
| pEY | poly-glutamine, tyrosine |
| Ph | phenyl |
| PhOH | phenol |
| PfP | pentafluorophenol |
| PfPy | pentafluoropyridine |
| PPTS | Pyridinium p-toluenesulfonate |
| Py | pyridine |
| PyBroP | bromo-tris-pyrrolidino-phosphonium hexafluorophosphate |
| q | quartet |
| RT | Room temperature |
| Sat'd | saturated |
| s | singlet |
| s- | secondary |
| t- | tertiary |
| t or tr | triplet |
| TBDMS | t-butyldimethylsilyl |
| TES | triethylsilane |
| TFA | trifluoroacetic acid |
| THF | tetrahydrofuran |
| TMOF | trimethyl orthoformate |
| TMS | trimethylsilyl |
| tosyl | p-toluenesulfonyl |
| Trt | triphenylmethyl |
| μL | microliter(s) |
| μM | Micromole(s) or micromolar |

Compound Synthesis

Schemes 1-2 depict general synthetic routes for compounds of the invention and are not intended to be limiting. Specific examples are described subsequently to this general synthetic description. With the descriptions of the general routes and the specific examples thereafter, one of ordinary skill in the art would be able to make compounds of the invention as described.

Scheme 1 shows that in general, compounds of formula I can be made, for example, via a convergent route. For example, ring A and ring B can be linked via functionality a' and b', respectively. Functionality a' and b' are used to construct a linking group between ring A and ring B. Typically, but not necessarily, such a linking group contains functionality according to formula I (e.g. $L^1$, $L^2$ and $R^4$) along with a 1,3-diketo moiety. Such 1,3-diketones are converted to the corresponding pyrazines, typically using hydrazine, according to formula I. Although Scheme 1 depicts functionality (e.g. $L^1$, $L^2$, $R^1$, $R^2$ and $R^4$) according to formula I as being introduced at particular stages of synthesis, one of ordinary skill in the art would understand that such functionality can be introduced or manipulated at any of various stages of the synthetic procedure used to make particular compounds depending on the nature of the functionality and the chemistry needed to introduce or otherwise protect the functionality.

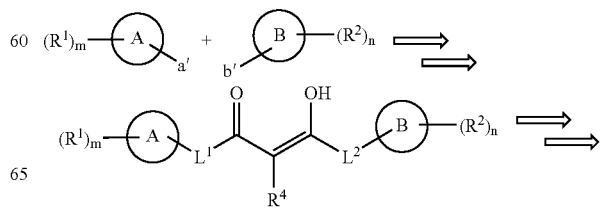

Scheme 1

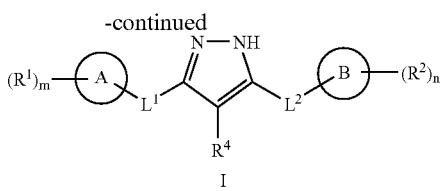

Scheme 2 shows another example using terminology consistent with Scheme 1. In this case a linear approach is used wherein the pyrazole ring and linker $L^2$ are appended onto ring B via functionality b'. Generally, but not necessarily, a radical containing a 1,3-diketo moiety is appended to ring B using b'. Then, the pyrazole ring is introduced as described in relation to Scheme 1. Once the pyrazole is made, then functionality c' is used to couple ring A and thereby form linking group $L^1$ and produce compounds according to formula I. The order of the steps described above can be varied, that is, ring A and the pyrazole can be linked first, followed by appending ring B to the pyrazole to make compounds of formula I. Again, although Scheme 2 depicts functionality (e.g. $L^1$, $L^2$, $R^1$, $R^2$ and $R^4$) according to formula I as being introduced at particular stages of synthesis, one of ordinary skill in the art would understand that such functionality can be introduced or manipulated at any of various stages of the synthetic procedure.

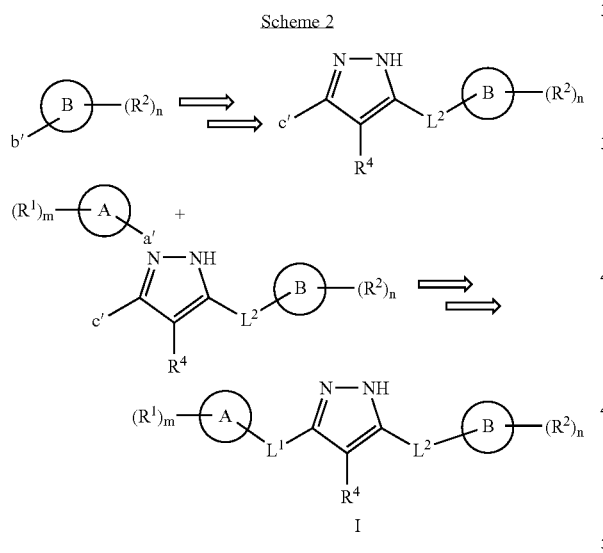

Scheme 2

One of ordinary skill in the art would recognize that the descriptions associated with Schemes 1-2 are generalizations; provided below are exemplary chemistries used to make compounds in accordance with Schemes 1-2 and formula I. One of ordinary skill in the art would also appreciate that there are other combinations of steps and chemistries that can be used to make compounds of the invention.

EXAMPLES

The following examples serve to more fully describe the manner of using the above-described invention, as well as to set forth the best mode contemplated for carrying out various aspects of the invention. It is understood that these examples in no way serve to limit the true scope of this invention, but rather are presented for illustrative purposes. All references cited herein are incorporated by reference in their entirety.

Example 1

4-{(E)-2-[3-(3-chlorophenyl)-1H-pyrazol-5-yl]ethenyl}phenol

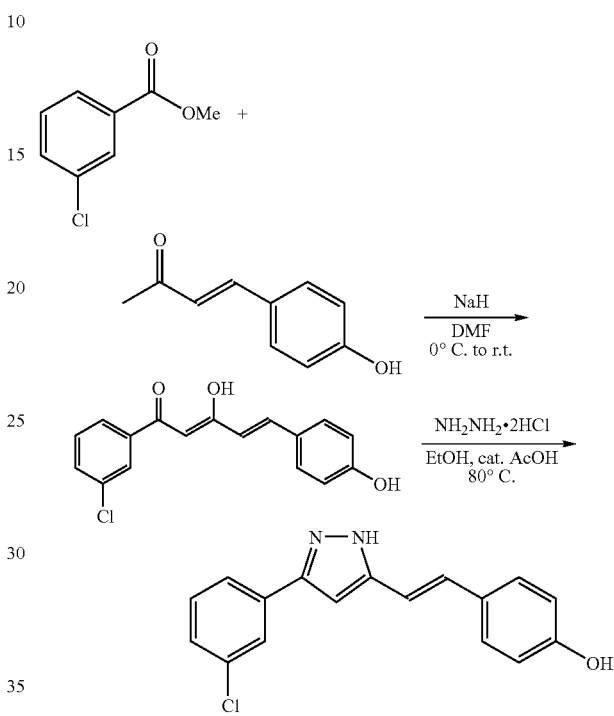

(2Z,4E)-1-(3-Chlorophenyl)-3-hydroxy-5-(4-hydroxyphenyl)penta-2,4-dien-1-one; NaH (60% dispersion, 0.477 g, 11.9 mmol) was added to a solution of methyl 3-chlorobenzoate (0.677 g, 3.97 mmol) and 4-hydroxybenzylideneacetone (0.644 g, 3.97 mmol) in anhydrous DMF (20 mL) at 0° C. The reaction was allowed to warm to room temperature overnight and quenched with saturated aqueous $NH_4Cl$ and neutralized with 1M HCl. The reaction was diluted with ethyl acetate (80 mL) and the organic layer washed successively with saturated aqueous $NaHCO_3$ and brine. The organic phase was separated and dried over $Na_2SO_4$, filtered, and concentrated in vacuo to provide the condensation product as a yellow oil (0.717 g, 60% yield).

4-{(E)-2-[3-(3-Chlorophenyl)-1H-pyrazol-5-yl]ethenyl}phenol: Hydrazine dihydro-chloride (0.263 g, 2.50 mmol) was added to a sealed tube charged with (2Z,4E)-1-(3-chlorophenyl)-3-hydroxy-5-(4-hydroxyphenyl)penta-2,4-dien-1-one (0.717 g, 2.39 mmol) in absolute ethanol (8 mL) and a catalytic amount of acetic acid. The reaction tube was sealed and heated to 80° C. After 12 hours the reaction was cooled to room temperature and concentrated in vacuo. The residue was dissolved in a small amount of methanol and precipitated with water, and the solid was collected by vacuum filtration to provide the title compound in (288 mg, 41% yield) as a yellow solid: $^1$H NMR (400 MHz, $CD_3OD$): δ 7.79 (bs, 1H), 7.68 (bd, J=7.6 Hz, 1H), 7.37 (m, 3H), 7.29 (bd, J=7.6 Hz, 1H), 7.12 (d, J=16.4 Hz, 1H), 6.86 (d, J=16.4 Hz, 1H), 6.81 (bs, 1H), 6.77 (m, 2H); MS (EI) for $C_{17}H_{13}ClN_2O$: 297.1 (MH$^+$).

Using the same or analogous synthetic techniques and/or substituting with alternative reagents, the following compounds of the invention were prepared:

4-[(E)-2-(3-Phenyl-1H-pyrazol-5-yl)ethenyl]phenol: $^1$H NMR (400 MHz, CD$_3$OD): δ 7.76 (bs, 2H), 7.37 (m, 4H), 7.31 (bs, 1H), 7.12 (d, J=16.4 Hz, 1H), 6.87 (bs, J=16.8 Hz, 1H), 6.77 (m, 3H); MS (EI) for C$_{17}$H$_{14}$N$_2$O: 263.1 (MH$^+$).

4-{(E)-2-[3-(4-Chlorophenyl)-1H-pyrazol-5-yl]ethenyl}phenol: $^1$H NMR (400 MHz, CD$_3$OD): δ 7.74 (bs, 2H), 7.38 (m, 4H), 7.11 (d, J=16.8 Hz, 1H), 6.87 (bd, J=16.4 Hz, 1H), 6.76 (m, 3H); MS (EI) for C$_{17}$H$_{13}$ClN$_2$O: 297.1 (MH$^+$).

4-{(E)-2-[3-(2-Chlorophenyl)-1H-pyrazol-5-yl]ethenyl}phenol: $^1$H NMR (400 MHz, CD$_3$OD): δ 7.68 (bs, 1H), 7.49 (bs, 1H), 7.39 (m, 2H), 7.35 (m, 2H), 7.12 (d, J=16.4 Hz, 1H), 6.90 (bd, J=16.4 Hz, 1H), 6.82 (bs, 1H), 6.78 (m, 2H); MS (EI) for C$_{17}$H$_{13}$ClN$_2$O: 297.1 (MH$^+$).

4-{(E)-2-[3-(1-Benzothien-2-yl)-1H-pyrazol-5-yl]ethenyl}phenol: $^1$H NMR (400 MHz, DMSO-d$_6$): δ 9.62 (bs, 1H), 7.92 (d, J=7.6 Hz, 1H), 7.81 (d, J=7.6 Hz, 1H), 7.70 (s, 1H), 7.39-7.30 (m, 4H), 7.13 (d, J=16.4 Hz, 1H), 6.89 (s, 1H), 6.88 (d, J=16.4 Hz, 1H), 6.78 (m, 2H); MS (EI) for C$_{19}$H$_{14}$N$_2$OS: 319.1 (MH$^+$).

4-{(E)-2-[3-(3,4-Dichlorophenyl)-1H-pyrazol-5-yl]ethenyl}phenol: $^1$H NMR (400 MHz, CD$_3$OD): δ 7.95 (d, J=2.0 Hz, 1H), 7.69 (dd, J=8.0, 2.0 Hz, 1H), 7.54 (d, J=8.0 Hz, 1H), 7.37 (m, 2H), 7.12 (d, J=16.4 Hz, 1H), 6.87 (d, J=16.4 Hz, 1H), 6.84 (s, 1H), 6.76 (m, 2H); MS (EI) for C$_{17}$H$_{12}$C$_{12}$N$_2$O: 331.01 (M+).

4-{(E)-2-[3-(5-Chloro-1-benzofuran-2-yl)-1H-pyrazol-5-yl]ethenyl}phenol: $^1$H NMR (400 MHz, DMSO-d$_6$): δ 9.63 (bs, 1H), 7.72 (d, J=2.4 Hz, 1H), 7.64 (d, J=8.4 Hz, 1H), 7.37 (m, 2H), 7.31 (dd, J=8.4, 2.4 Hz, 1H), 7.17 (d, J=16.4 Hz, 1H), 7.16 (s, 1H), 6.91 (s, 1H), 6.89 (d, J=16.4 Hz, 1H), 6.77 (m, 2H); MS (EI) for C$_{19}$H$_{13}$ClN$_2$O$_2$: 337.1 (MH$^+$).

4-{(E)-2-[3-(1-Benzofuran-2-yl)-1H-pyrazol-5-yl]ethenyl}phenol: $^1$H NMR (400 MHz, DMSO-d$_6$): δ 9.63 (bs, 1H), 7.64 (d, J=7.6 Hz, 1H), 7.60 (d, J=8.4 Hz, 1H), 7.37 (m, 2H), 7.27 (m, 2H), 7.17 (s, 1H), 7.16 (d, J=16.4 Hz, 1H), 6.89 (s, 1H), 6.89 (d, J=16.4 Hz, 1H), 6.77 (m, 2H); MS (EI) for C$_{19}$H$_{14}$N$_2$; O$_2$: 303.1 (MH$^+$).

4-{(E)-2-[5-(2-Fluorophenyl)-1H-pyrazol-3-yl]ethenyl}phenol: $^1$H NMR (400 MHz, DMSO-d$_6$): δ 7.81 (m, 2H), 7.36 (d, 2H), 7.24 (m, 2H), 7.08 (d, 1H), 6.88 (d, 1H), 6.86 (s, 1H), 6.75 (d, 2H); MS (EI) for C$_{17}$H$_{13}$N$_2$OF: 281.1 (MH$^+$).

4-{(E)-2-[5-(3-fluorophenyl)-1H-pyrazol-3-yl]ethenyl}phenol: $^1$H NMR (400 MHz, DMSO-d$_6$): δ 7.63 (d, 1H), 7.58 (d, 1H), 7.44 (m, 1H), 7.36 (d, 2H), 7.13 (m, 1H), 7.09 (d, 1H), 6.94 (s, 1H), 6.85 (d, 1H), 6.78 (d, 2H); MS (EI) for C$_{17}$H$_{13}$N$_2$OF: 281.1 (MH$^+$).

4-{(E)-2-[5-(4-fluorophenyl)-1H-pyrazol-3-yl]ethenyl}phenol: $^1$H NMR (400 MHz, DMSO-d$_6$): δ 7.80 (t, 2H), 7.36 (d, 2H), 7.23 (t, 2H), 7.07 (d, 1H), 6.88 (d, 1H), 6.85 (s, 1H), 6.74 (d, 2H); MS (EI) for C$_{17}$H$_{13}$N$_2$OF: 281.1 (MH$^+$).

4-((E)-2-{5-[2-(methyloxy)phenyl]-1H-pyrazol-3-yl}ethenyl)phenol: $^1$H NMR (400 MHz, DMSO-d$_6$): δ 7.77 (dd, 1H), 7.38 (d, 2H), 7.31 (dt, 1H), 7.11 (d, 1H), 7.00 (dt, 1H), 6.91 (d, 1H), 6.90 (s, 1H), 3.90 (s, 3H); MS (EI) for C$_{18}$H$_{16}$N$_2$O$_2$: 293.1 (MH$^+$).

4-((E)-2-{5-[3-(methyloxy)phenyl]-1H-pyrazol-3-yl}ethenyl)phenol: $^1$H NMR (400 MHz, DMSO-d$_6$): δ 7.35 (m, 5H), 7.08 (d, 1H), 6.88 (m, 3H), 6.76 (d, 2H), 3.80 (s, 3H); MS (EI) for C$_{18}$H$_{16}$N$_2$O$_2$: 293.1 (MH$^+$).

Example 2

4-{(E)-2-[3-(1H-Benzimidazol-2-yl)-1H-pyrazol-5-yl]ethenyl}phenol

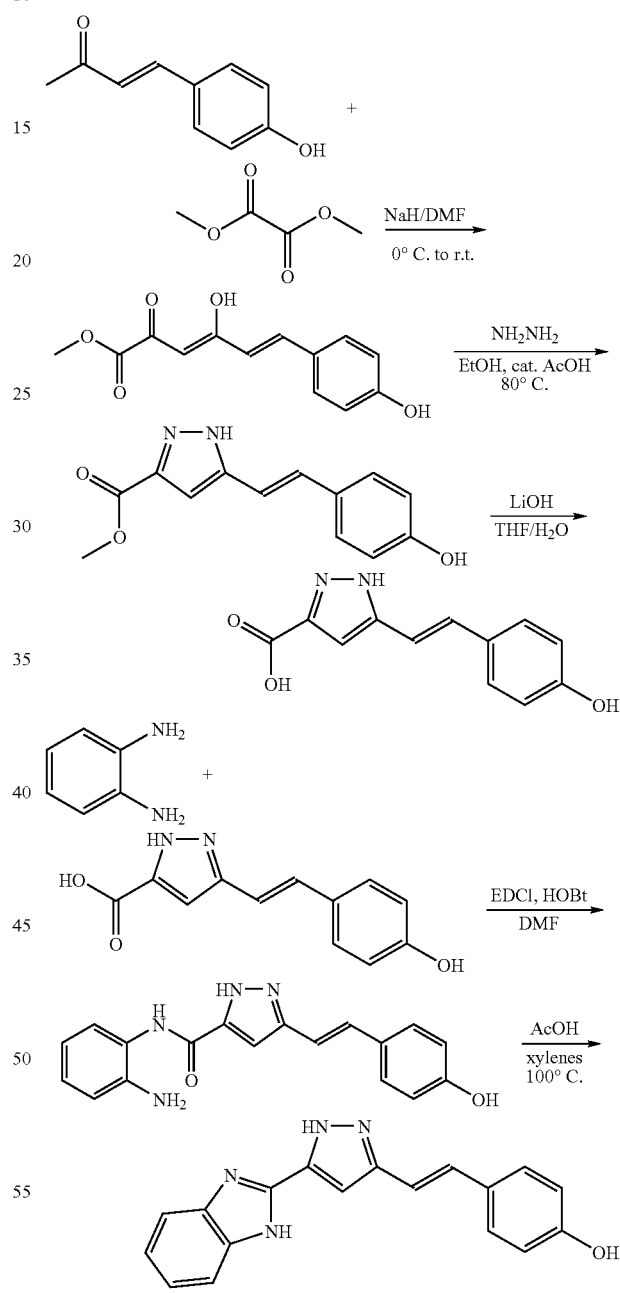

Methyl (2Z,4E)-3-hydroxy-5-(4-hydroxyphenyl)penta-2,4-dienoate: NaH (60% dispersion, 0.183 g, 7.6 mmol) was added to a solution of dimethyl oxylate (0.375 g, 3.2 mmol) and 4-hydroxybenzylideneacetone (0.515 g, 3.2 mmol) in anhydrous DMF (10 mL) at 0° C. The reaction was allowed to warm to room temperature overnight and quenched with saturated aqueous NH$_4$Cl and neutralized with 1M HCl. The reaction was diluted with ethyl acetate (80 mL) and the organic layer washed successively with saturated aqueous NaHCO$_3$ and brine. The organic phase was separated and dried over Na$_2$SO$_4$, filtered, and concentrated in vacuo to provide the condensation product as a yellow oil (0.391 g, 50% yield).

1H-Pyrazole-3-carboxylic acid, 5-[(E)-2-(4-hydroxyphenyl)ethenyl]-, methyl ester: Hydrazine (0.079 g, 1.6 mmol) was added to a sealed tube charged with methyl (2Z,4E)-3-hydroxy-5-(4-hydroxyphenyl)penta-2,4-dienoate (0.391 g, 1.6 mmol) in absolute ethanol (8 mL) and a catalytic amount of acetic acid. The reaction tube was sealed and heated to 80° C. After 12 hours the reaction was cooled to room temperature and concentrated in vacuo. The residue was dissolved in a small amount of methanol and precipitated with water and the solid was collected by vacuum filtration to provide the title compound (240 mg, 41% yield): $^1$H NMR (400 MHz, CD$_3$OD): δ 13.15 (bs, 1H), 7.37 (d, J=8.59 Hz, 1H), 7.18 (d, J=16.6 Hz, 1H), 6.87 (s, 1H), 6.85 (d, J=16.6 Hz, 1H), 6.78 (d, J=8.59 Hz, 1H), 3.80 (s, 3H).

4-{(E)-2-[3-(1H-Benzimidazol-2-yl)-1H-pyrazol-5-yl]ethenyl}phenol: Glacial acetic acid (1.0 mL) was added to a sealed tube charged with a solution of N-(2-aminophenyl)-3-[(E)-2-(4-hydroxyphenyl)ethenyl]-1H-pyrazole-5-carboxamide (0.044 g, 1.36 mmol) in xylenes (1.0 mL) and heated to 100° C. After twelve hours the reaction was cooled to room temperature and concentrated in vacuo. The residue was purified on reverse phase HPLC using water-acetonitrile gradient (0.1% TFA) to provide the title benzimidazole (10 mg, 25% yield) as a white solid: $^1$H NMR (400 MHz, CD$_3$OD): δ 7.59 (bs, 2H), 7.41 (m, 2H), 7.25 (m, 2H), 7.16 (d, J=16.4 Hz, 1H), 7.03 (s, 1H), 6.92 (d, J=16.4 Hz, 1H), 6.79 (m, 2H); MS (EI) for C$_{18}$H$_{14}$N$_4$O: 303.1 (MH$^+$).

Example 3

4-((E)-2-{3-[6-(4-Methylpiperazin-1-yl)-1H-benzimidazol-2-yl]-1H-pyrazol-5-yl}ethenyl)phenol

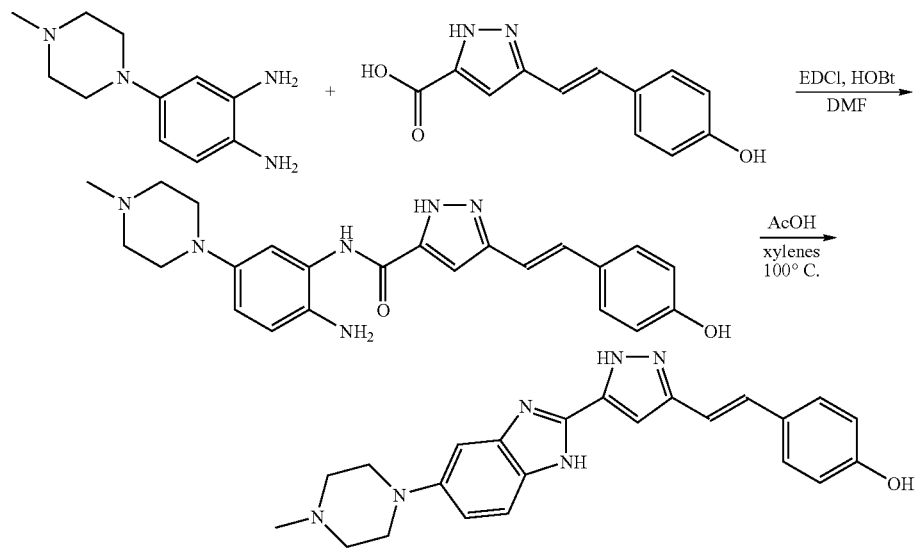

5-[(E)-2-(4-Hydroxyphenyl)ethenyl]-1H-pyrazole-3-carboxylic acid: Lithium hydroxide hydrate (0.522 g, 12.44 mmol) was added to the solution of 1H-pyrazole-3-carboxylic acid, 5-[(E)-2-(4-hydroxyphenyl)ethenyl]-, methyl ester (1.52 g, 6.22 mmol) in THF (50 mL) and H$_2$O (12.5 mL). The reaction mixture was stirred overnight at room temperature. THF was removed on a rotary evaporator. The residue was neutralized with 3N HCl, and the solid was collected by vacuum filtration to provide the title compound in (1.2 g, 84% yield).

N-(2-Aminophenyl)-3-[(E)-2-(4-hydroxyphenyl)ethenyl]-1H-pyrazole-5-carboxamide: 1-[3-(Dimethylamino)propyl]-3-ethylcarbodiimide hydrochloride (EDCI, 0.377 g, 1.97 mmol) was added to a solution of 1,2-diaminobenzene (0.141 g, 1.31 mmol), 5-[2[(4-hydroxyphenyl)-vinyl]-2H-pyrazol-3-carboxylic acid (0.301 g, 1.31 mmol) and HOBt (0.266 g, 1.97 mmol) in anhydrous DMF (7 mL). The reaction was stirred under nitrogen at room temperature. After twelve hours the reaction was concentrated in vacuo and precipitated from methanol with a small amount of water. The solid was collected by vacuum filtration and further purified on reverse phase HPLC using water-acetonitrile gradient (0.1% TFA) to provide the corresponding amide (44 mg, 10% yield).

N-[2-Amino-5-(4-methylpiperazin-1-yl)phenyl]-3-[(E)-2-(4-hydroxyphenyl)ethenyl]-1H-pyrazole-5-carboxamide: EDCI (0.078 g, 0.41 mmol) was added to a solution of 5-(4-methyl-piperazin-1-yl)-1,2-aminobenzene (0.085 g, 0.41 mmol), 5-[2[(4-hydroxyphenyl)-vinyl]-2H-pyrazol-3-carboxylic acid (0.047 g, 0.21 mmol) and DMAP (0.050 g, 0.41 mmol) in anhydrous DMF (2 mL) at room temperature. After twelve hours the reaction was concentrated in vacuo affording crude product.

4-((E)-2-{5-[5-(4-Methylpiperazin-1-yl)-1H-benzimidazol-2-yl]-1H-3-yl}ethenyl)phenol: The 0.21 mmol of crude N-[2-amino-5-(4-methylpiperazin-1-yl)phenyl]-3-[(E)-2-(4-hydroxyphenyl)ethenyl]-1H-pyrazole-5-carboxamide in a solution of AcOH:xylenes (1:1, 2 mL) was heated to 100° C. in a sealed tube. After twelve hours the reaction was cooled to room temperature and concentrated in vacuo. The residue was purified on reverse phase HPLC using water-acetonitrile gradient (0.1% TFA) to provide the title benzimidazole (12 mg, 14% yield) as a dark purple solid: $^1$H NMR (400 MHz, CD$_3$OD): δ 7.89 (s, 1H), 7.65 (bs, 1H), 7.36 (m, 2H), 7.23 (bs, 1H), 7.14 (bd, J=16.4 Hz, 2H), 6.86 (bd, J=15.2 Hz, 1H), 6.75 (m, 2H), 3.92 (bd, J=11.6 Hz, 2H), 3.65 (bd, J=11.2 Hz, 2H), 3.39-3.21 (m, 3H), 2.99 (s, 3H), 2.90 (bt, J=12.4 Hz, 1H); MS (EI) for C$_{23}$H$_{24}$N$_6$O: 401.2 (MH$^+$).

Example 4

4-((E)-2-{3-[4-(4-Methylpiperazin-1-yl)phenyl]-1H-pyrazol-5-yl}ethenyl)phenol

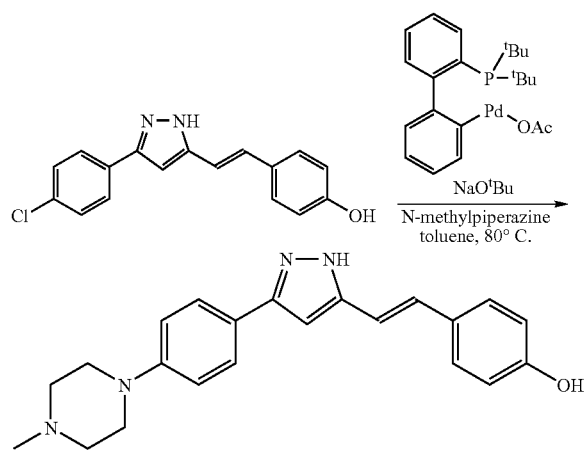

4-((E)-2-{3-[4-(4-Methylpiperazin-1-yl)phenyl]-1H-pyrazol-5-yl}ethenyl)phenol: N-Methylpiperazine (50 μL, 0.49 mmol) was added to a suspension of 4-{(E)-2-[3-(4-chlorophenyl)-1H-pyrazol-5-yl]ethenyl}phenol (0.097 g, 0.33 mmol), NaOtBu (0.110 g, 1.14 mmol) and acetato(2'-di-tert-butylphosphino-1,1'-biphenyl-2-yl)palladium (0.015 g, 33 μmol, 10 mol %) in anhydrous toluene (1.5 mL) and heated to 80° C. After 24 hours, the reaction was cooled to room temperature, diluted with methanol and filtered though a celite pad. The filtrate was concentrated in vacuo and the residue purified on reverse phase HPLC using water-acetonitrile gradient (0.1% TFA) to provide the title compound (10 mg, 9% yield) as an off-white solid: $^1$H NMR (400 MHz, CD$_3$OD): δ 7.71 (m, 2H), 7.40 (m, 2H), 7.20 (d, J=16.4 Hz, 1H), 7.10 (m, 2H), 6.87 (d, J=16.4 Hz, 1H), 6.84 (s, 1H), 6.79 (m, 2H), 3.95 (bd, J=14.4 Hz, 2H), 3.63 (bd, J=11.2 Hz, 2H), 2.28 (m, 2H), 3.10 (bt, J=13.2 Hz, 2H), 2.99 (s, 3H); MS (EI) for C$_{22}$H$_{24}$N$_4$O: 361.2 (MH$^+$).

Using the same or analogous synthetic techniques and/or substituting with alternative reagents, the following compound of the invention was prepared:

4-((E)-2-{3-[3-(4-Methylpiperazin-1-yl)phenyl]-1H-pyrazol-5-yl}ethenyl)phenol: $^1$H NMR (400 MHz, CD$_3$OD): δ 7.50-7.45 (m, 4H), 7.36 (bd, J=8.4 Hz, 1H), 7.34 (s, 1H), 7.21 (dd, J=8.0, 2.4 Hz, 1H), 6.89 (d, J=16.4 Hz, 1H), 6.82 (m, 2H), 3.99 (bd, J=14.0 Hz, 2H), 3.65 (bd, J=12.0 Hz, 2H), 3.31 (m, 2H), 3.20 (dt, J=13.6, 1.6 Hz, 2H), 2.99 (s, 3H); MS (EI) for C$_{22}$H$_{24}$N$_4$O: 361.2 (MH$^+$).

Example 5

2-(Methyloxy)-4-[(E)-2-(5-phenyl-1H-pyrazol-3-yl)ethenyl]phenol

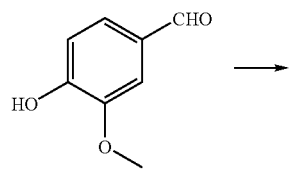

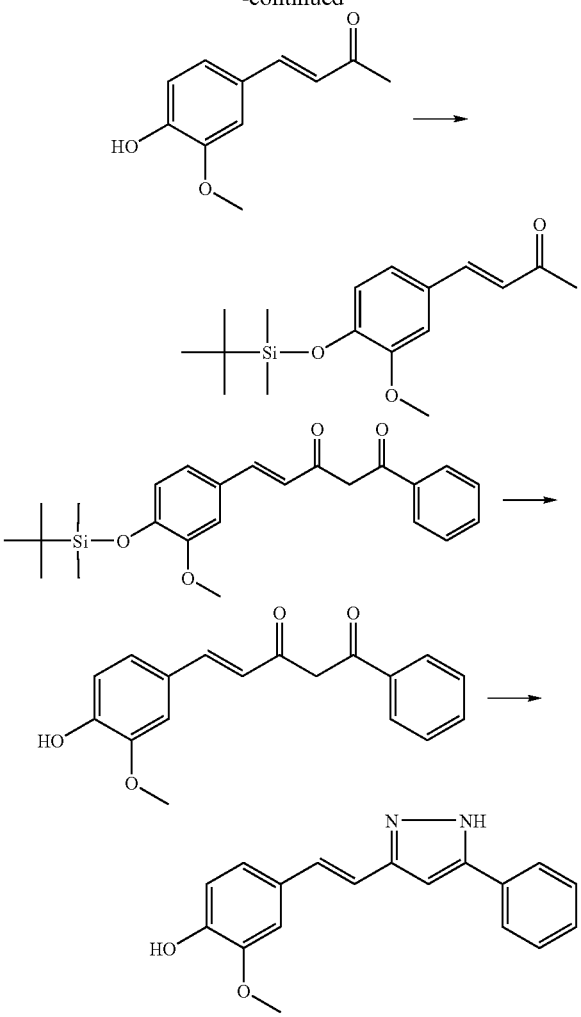

4-(4-Hydroxy-3-methoxy-phenyl)but-3-ene-2-one: To a solution of acetone (15.30 g, 263.76 mmol) in a mixture of ethanol (35 mL) and water (15 mL) were added sodium hydroxide (2.90 g, 72.54 mmol) and 4-hydroxy-3-methoxy-benzaldehyde (5.01 g, 32.97 mmol). The reaction mixture was stirred at room temperature for 15 h. The reaction was cooled to 0° C. and quenched with 2.0 N hydrochloric acid until the solution became slightly acidic. The solution was extracted with ethyl acetate (4×100 mL). The combined organic layers were washed with water (50 mL) and saturated aqueous sodium chloride (50 mL). The organic layer was dried over magnesium sulfate, filtered, and concentrated at reduced pressure to afford 4-(4-hydroxy-3-methoxy-phenyl)but-3-ene-2-one (5.52 g, 87% yield) as a yellow solid: MS (EI) for C$_{11}$H$_{12}$O$_3$: 193 (MH$^+$).

4-{4-[(tert-Butyl-dimethyl-silanyloxy)-methyl}-3-methoxy-phenyl}-but-3-ene-2-one: To a solution of 4-(4-Hydroxy-3-methoxy-phenyl)but-3-ene-2-one (4.402 g, 22.93 mmol) in N,N-dimethylformamide (28.5 mL) were added imidazole (1.71 g, 25.22 mmol) and tert-butyldimethylsilyl chloride (3.8 g; 25.22 mmol). The reaction was allowed to stir for 4 h, then diluted with ethyl acetate (300 mL) and washed with water (50 mL), saturated aqueous sodium bicarbonate (40 mL), and saturated aqueous sodium chloride (50 mL). The organic layer was dried over magnesium sulfate, filtered, and concentrated at reduced pressure to give crude product. Column purification on silica (8:2 hexanes/ethyl acetate) afforded 4-{4-[(tert-butyl-dimethyl-silanyloxy)-methyl}-3-methoxy-phenyl}-but-3-ene-2-one (5.24 g, 73% yield) as a solid: $^1$H NMR (400 MHz, CDCl$_3$): δ 7.32 (d, 2H), 6.92 (m, 2H), 6.78 (d, 1H), 6.53 (d, 2H), 3.78 (s, 3H), 2.28 (s, 3H), 0.92 (s, 9H), 0.16 (s, 6H).

5-(Hydroxy-3-methoxy-phenyl)-1-phenyl-pent-4-ene-1,3-dione: To a slurry solution of sodium hydride (60%, 0.13 g, 3.28 mmol) in N,N-dimethylformamide were added 4-{4-[(tert-butyl-dimethyl-silanyloxy)-methyl}-3-methoxy-phenyl}-but-3-ene-2-one (0.50 g, 1.54 mmol) and methyl benzoate (0.26 g, 1.97 mmol) at 0° C. The reaction was stirred at 0° C. for 1 h. The reaction mixture was removed from ice-bath and heated for 1 h at 60° C. The reaction was cooled to room temperature and quenched with aqueous 1.0 N hydrochloric acid (2.0 mL) slowly. Excess tetrabutylammonium fluoride was added to the above solution to deprotect the silyl group. The reaction was diluted with ethyl acetate (200 mL), washed with water (3×60 mL) and saturated aqueous sodium chloride (50 mL). The organic layer dried over magnesium sulfate, filtered, and concentrated to give impure crude product. Purification on silica (9:1 to 7:3 hexanes/ethyl acetate) to afford 5-(hydroxy-3-methoxy-phenyl)-1-phenyl-pent-4-ene-1,3-dione (0.14 g, 30% yield) as a solid: MS (EI) for $C_{18}H_{16}O_4$: 297 (MH$^+$).

2-(Methyloxy)-4-[(E)-2-(5-phenyl-1H-pyrazol-3-yl)ethenyl]phenol: To a mixture of 5-(hydroxy-3-methoxy-phenyl)-1-phenyl-pent-4-ene-1,3-dione (0.14 g, 0.48 mmol) and hydrazine monohydrate (0.02 g, 0.48 mmol) were added ethanol (24 mL) and acetic acid (1 drop) in a sealed tube. The reaction was heated at 65-70° C. overnight. The solvent was removed under reduced pressure to afford crude product. Purification on triethylamine treated silica (1:1 hexanes/ethyl acetate) afforded a mixture of two products. Reverse phase HPLC purification afforded 2-(methyloxy)-4-[(E)-2-(5-phenyl-1H-pyrazol-3-yl)ethenyl]phenol (0.015 g, 10% yield) as trifluoroacetate salt: $^1$H NMR (400 MHz, CDCl$_3$): δ 9.21 (br s, 2H), 7.78 (br s, 2H), 7.42 (m, 3H), 7.20 (br d, 1H), 6.94 (m, 6H), 3.92 (s, 3H); MS (EI) for $C_{18}H_{16}N_2O_2$: 293 (MH$^+$).

Using the same or analogous synthetic techniques and/or substituting with alternative reagents, the following compounds of the invention were prepared:

2-(methyloxy)-4-((E)-2-{5-[(E)-2-phenylethenyl]-1H-pyrazol-3-yl}ethenyl)phenol: $^1$H NMR (400 MHz, CDCl$_3$): δ 7.42 (br d, 2H), 7.30 (m, 3H), 7.15 (m, 2H), 7.02 (m, 3H), 6.85 (m, 3H), 6.68 (br s, 1H), 3.85 (s, 3H); MS (EI) for $C_{20}H_{18}N_2O_2$: 319 (MH$^+$).

4-((E)-2-{3-[(E)-2-(4-chlorophenyl)ethenyl]-1H-pyrazol-5-yl}ethenyl)-2-(methyloxy)phenol: $^1$H NMR (400 MHz, CDCl$_3$): δ 7.38 (br d, 2H), 7.32 (br d, 2H), 7.20 (m, 3H), 6.90 (m, 6H), 6.62 (br s, 1H), 3.95 (s, 3H); MS (EI) for $C_{20}H_{17}N_2O_2Cl$: 343, 355 (MH$^+$).

4-((E)-2-{3-[(E)-2-(4-fluorophenyl)ethenyl]-1H-pyrazol-5-yl}ethenyl)-2-(methyloxy)phenol: $^1$H NMR (400 MHz, d-MeOH): δ 7.46 (m, 2H), 7.08 (m, 5H), 6.90 (m, 2H), 6.75 (d, 1H), 6.68 (br d, 2H), 3.82 (s, 3H); MS (EI) for $C_{20}H_{17}N_2O_2F$: 337 (MH$^+$).

4-((E)-2-{3-[(E)-2-(2,4-difluorophenyl)ethenyl]-1H-pyrazol-5-yl}ethenyl)-2-(methyloxy)phenol: $^1$H NMR (400 MHz, d-MeOH): δ 7.42 (m, 1H), 7.25 (d, 1H), 7.15 (m, 3H), 7.02 (m, 3H), 6.90 (d, 1H), 6.78 (br t, 2H), 3.92 (s, 3H); MS (EI) for $C_{20}H_{16}N_2O_2F_2$: 355 (MH$^+$).

4-((E)-2-{5-[(E)-2-phenylethenyl]-1H-pyrazol-3-yl}ethenyl)phenol: $^1$H NMR (400 MHz, d-MeOH): δ 7.64 (br d, 2H), 7.44 (m, 7H), 7.12 (br t, 2H), 6.87 (m, 3H); MS (EI) for $C_{19}H_{16}N_2O$: 289 (MH$^+$).

4-[(E)-2-(3-pyridin-3-yl-1H-pyrazol-5-yl)ethenyl]phenol: $^1$H NMR (400 MHz, d-MeOH): δ 9.20 (br s, 1H), 8.85 (d, 1H), 8.65 (br s, 1H), 8.20 (br s, 1H), 7.42 (d, 2H), 7.20 (d, 1H), 7.04 (s, 1H), 6.85 (d, 1H), 6.80 (d, 2H); MS (EI) for $C_{16}H_{13}N_3O$: 264 (MH$^+$).

4-[(E)-2-(3-pyridin-4-yl-1H-pyrazol-5-yl)ethenyl]phenol: $^1$H NMR (400 MHz, d-MeOH): δ 8.64 (br d, 1H), 8.50 (br t, 1H), 8.34 (br d, 1H), 7.82 (br t, 1H), 7.40 (d, 2H), 7.18 (m, 2H), 6.90@(d, 1H), 6.80 (d, 2H); MS (EI) for $C_{16}H_{13}N_3O$: 264 (MH$^+$).

4-[(E)-2-(5-naphthalen-2-yl-1H-pyrazol-3-yl)ethenyl]phenol: $^1$H NMR (400 MHz, d-MeOH): δ 8.38 br s, 1H), 7.94 (m, 5H), 7.60 (m, 2H), 7.52 (m, 3H), 7.38 (s, 1H), 6.92 (d, 1H), 6.84 (d, 2H); MS (EI) for $C_{21}H_{16}N_2O$: 313 (MH$^+$).

4-[(E)-2-(5-pyridin-2-yl-1H-pyrazol-3-yl)ethenyl]phenol: $^1$H NMR (400 MHz, d-MeOH): δ 8.70 (d, 1H), 8.62 (t, 1H), 8.44 (d, 1H), 7.92 (t, 1H), 7.40 (d, 2H), 7.20 (d, 2H), 6.90 (d, 1H), 6.80 (d, 2H); MS (EI) for $C_{16}H_{13}N_3O$: 264 (MH$^+$).

4-[(E)-2-(5-biphenyl-3-yl-1H-pyrazol-3-yl)ethenyl]phenol: $^1$H NMR (400 MHz, d-MeOH): δ 7.42 (m, 1H), 7.25 (d, 1H), 7.15 (m, 3H), 7.02 (m, 3H), 6.90 (d, 1H), 6.78 (br t, 2H), 3.92 (s, 3H); MS (EI) for $C_{20}H_{16}N_2O_2F_2$: 355 (MH$^+$).

1,1-Dimethylethyl(4-{3-[(E)-2-phenylethenyl]-1H-pyrazol-5-yl}phenyl)carbamate: $^1$H NMR (400 MHz, d-MeOH): δ 7.66 (br d, 2H), 7.50 (in, 5H), 7.35 (br t, 3H), 7.28 (br d, 1H), 7.20 (d, 1H), 7.08 (d, 1H), 6.82 (s, 1H), 1.50 (s, 9H); MS (EI) for $C_{22}H_{23}N_3O_2$: 362 (MH$^+$).

Example 6

2-{5-[(E)-2-phenylethenyl]-1H-pyrazol-3-yl}-1-benzofuran-6-ol

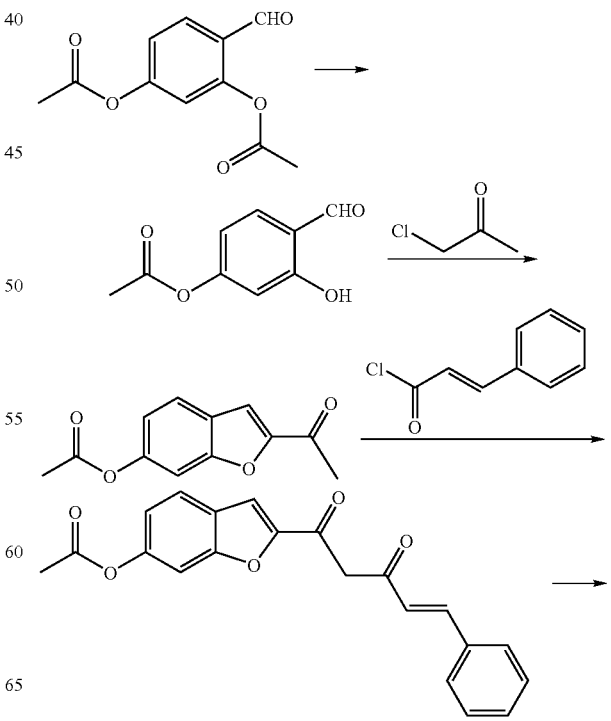

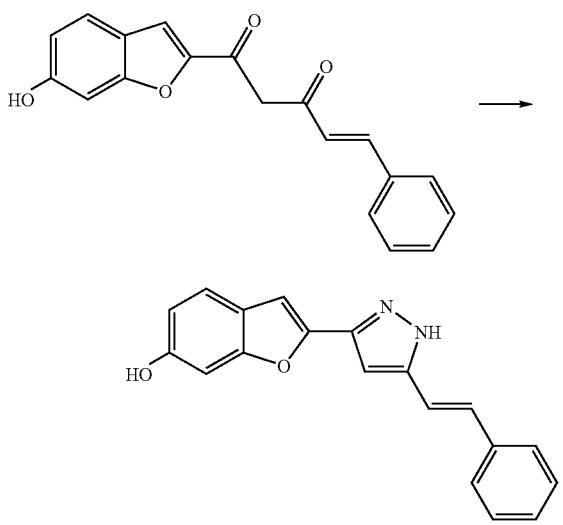

4-Formyl-3-hydroxyphenyl acetate: To a solution of 4-formylbenzene-1,3-diyl diacetate (5.56 g, 25.08 mmol) in ethanol (20 mL) was added a solution of sodium hydroxide (1.00 g, 25.08 mmol) in water (12 mL). The reaction was stirred overnight at room temperature. The reaction was carefully neutralized with 2.0 N aqueous solution of hydrochloric acid (12.8 mL) at 0° C. and diluted with ethyl acetate (400 mL). The organic layer was washed with water (60 mL) and saturated aqueous sodium chloride (50 mL), dried over magnesium sulfate, filtered, and concentrated to afford, the product (2.01 g, 44% yield) as a gray solid: $^1$H NMR (400 MHz, d-MeOH): δ 9.90 (s, 1H), 7.68 (d, 1H), 6.80 (d, 1H), 6.75 (s, 1H), 4.82 (br s, 1H), 2.20 (s, 3H).

2-Acetyl-1-benzofuran-6-yl acetate: To a'solution of acetic acid 4-Formyl-3-hydroxyphenyl acetate (1.74 g, 9.67 mmol) in acetonitrile (10 mL) was added solid anhydrous potassium carbonate (1.33 g, 9.67 mmol) and stirred for 30 min at room temperature prior to the slow addition of chloroacetone (0.98 g, 9.67 mmol) via a syringe. A reflux condenser was attached and the reaction was heated to reflux overnight, then cooled to room temperature and diluted with ethyl acetate (350 mL). The organic layer was washed with 2.0 N aqueous HCl (100 mL), saturated aqueous sodium chloride (60 mL), dried over magnesium sulfate, filtered, and concentrated to afford crude product. Purification on silica (9:1 to 7:3, hexanes/ethyl, acetate) afforded the desired product together with the product without the acetate group. The total weight of the mixture obtained was 0.4421 g. This mixture was taken to the next step without further purification.

(4E)-1-(6-Hydroxy-1-benzofuran-2-yl)-5-phenylpent-4-ene-1,3-dione: To a solution of the crude 2-acetyl-1-benzofuran-6-yl acetate (0.23 g) in tetrahydrofuran (5 mL) at −78° C. was added lithium diisopropylamine (2.0 N solution in THF, 1.63 mL, 3.25 mmol). The mixture was stirred at the same temperature for 20 min prior to the addition of cinnamoyl chloride (0.22 g, 1.3 mmol). The reaction was warmed slowly to room temperature and stirred overnight. The reaction was treated with 1.0 N aqueous hydrochloric acid solution (10 mL) at 0° C. and diluted with ethyl acetate (250 mL). The organic layer was washed with 2N aqueous hydrochloric acid (100 mL), saturated aqueous sodium chloride (60 mL), dried over magnesium sulfate, filtered, and concentrated to afford crude product. Purification on silica (gradient 8:2 to 6:4, hexanes/ethyl acetate) afforded the product (0.12 g, 30% yield) as a yellow solid: MS (EI) for $C_{19}H_{14}O_4$: 307 (MH$^+$).

2-{5-[(E)-2-Phenylethenyl]-1H-pyrazol-3-yl}-1-benzofuran-6-ol: To a mixture of (4E)-1-(6-hydroxy-1-benzofuran-2-yl)-5-phenylpent-4-ene-1,3-dione (0.48 mmol) and hydrazine monohydrate (0.02 g, 0.48 mmol) were added ethanol (24 mL) and acetic acid (1 drop) in a sealed tube. The reaction was heated at 65-700° C. overnight. The solvent was removed under reduced pressure to afford crude product. The crude product was purified by reverse phase HPLC. The fractions from HPLC were combined, neutralized with 1.0 N aqueous sodium hydroxide solution, and diluted with ethyl acetate (200 mL). The organic layer was washed with saturated aqueous sodium chloride (50 mL), dried over magnesium sulfate, filtered, and concentrated to afford the product (11% yield): $^1$H NMR (400 MHz, CD$_3$Cl): δ 7.58 (br d, 2H), 7.35 (m, 4H), 7.25 (t, 2H), 7.10 (br d, 1H), 7.05 (br s, 1H), 6.94 (br d, 1H), 6.88 (br s, 1H), 6.75 (dd, 1H); MS (EI) for $C_{19}H_{14}N_2O_2$: 303 (MH$^+$).

Example 7

N-[4-chloro-3-(trifluoromethyl)phenyl]-N'-[4-(3-phenyl-1H-pyrazol-5-yl)phenyl]urea

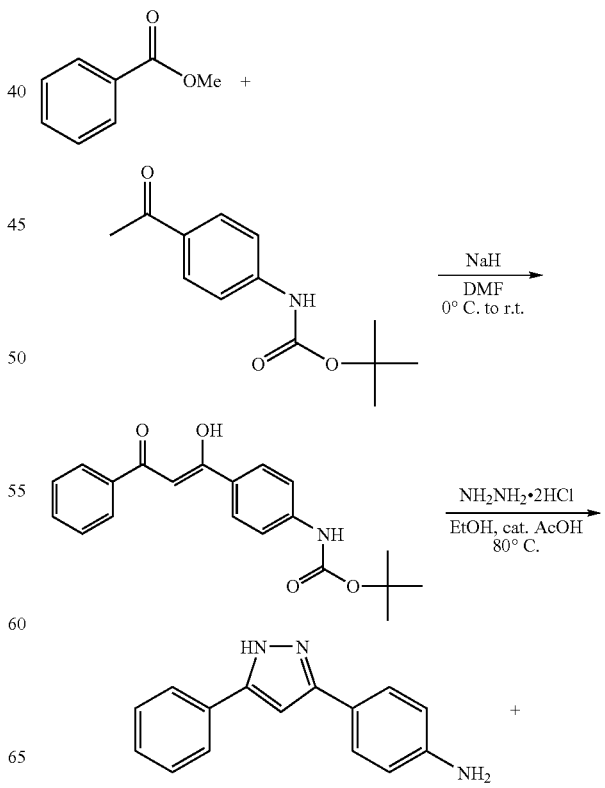

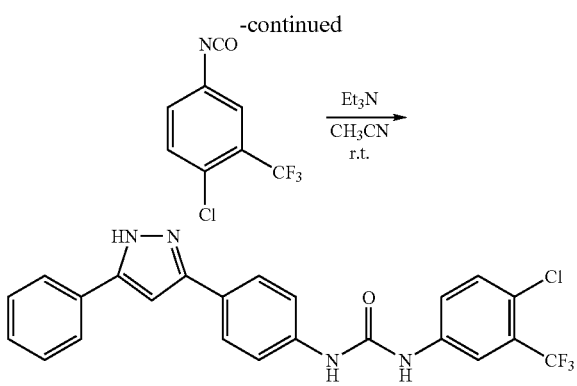

1,1-Dimethylethyl {4-[(1z)-1-hydroxy-3-oxo-3-phenyl-prop-1-en-1-yl]phenyl}carbamate: NaH (60% dispersion, 0.388 g, 16.2 mmol) was added to a solution of methyl benzoate (0.629 g, 4.62 mmol) and 1,1-dimethylethyl (4-acetylphenyl)carbamate (N-BOC-4-aminoacetophenone 1.09 g, 4.62 mmol) in anhydrous DMF (20 mL) at 0° C. The reaction was allowed to warm to room temperature overnight then quenched with saturated aqueous NH$_4$Cl and neutralized with 1M HCl. The reaction was diluted with ethyl acetate (80 mL) and the organic layer washed successively with saturated aqueous NaHCO$_3$ and brine. The organic phase was separated and dried over Na$_2$SO$_4$, filtered, and concentrated in vacuo to provide the condensation product as a yellow oil (1.31 g, 83% yield). The product was used in the subsequent step without further purification.

4-(5-Phenyl-1H-pyrazol-3-yl) aniline: Hydrazine dihydro chloride (0.427 g, 4.00 mmol) was added to a sealed tube charged with the above product (1.31 g, 3.87 mmol) in absolute ethanol (17 mL) and a catalytic amount of acetic acid. The reaction tube was sealed and heated to 85° C. After 12 hours the reaction was cooled to room temperature and concentrated in vacuo. The residue was dissolved in a small amount of methanol and precipitated with water and the solid was collected by vacuum filtration to provide the desired compound in (974 mg, 75% yield) as a white solid. The BOC group was removed under the reaction conditions: $^1$H NMR (400 MHz, DMSO-d$_6$): δ 7.95 (m, 3H), 7.82 (m, 2H), 7.45 (m, 3H), 7.34 (m, 2H), 7.23 (s, 1H), 2.30 (bs, 2H); MS (EI) for C$_{15}$H$_{13}$N$_3$: 236.1 (MH$^+$).

N-[4-chloro-3-(trifluoromethyl)phenyl]-N'-[4-(5-phenyl-1H-pyrazol-3-yl)phenyl]urea: Triethylamine (64 mL, 0.45 mmol) was added to a suspension of N-[4-(3-phenyl-1H-pyrazol-5-yl)aminobenzene (0.102 g, 0.43 mmol) and 4-chloro-3-trifluoromethyl-phenylisocyanate (0.096 g, 0.43 mmol) in anhydrous acetonitrile (2.0 mL) at room temperature. After twelve hours the reaction was concentrated in vacuo and purified on reverse phase HPLC using water-acetonitrile gradient (0.1% TFA) to provide the title compound (23 mg, 16% yield) as a white solid: $^1$H NMR (400 MHz, DMSO-d$_6$): δ 9.24 (s, 1H), 9.01 (s, 1H), 8.11 (d, J=2.0 Hz, 1H), 7.81 (m, 2H), 7.74 (m, 2H), 7.62 (m, 2H), 7.53 (m, 2H), 7.42 (t, J=8.0 Hz, 2H), 7.32 (t, J=7.6 Hz, 1H), 7.10 (s, 1H); MS (EI) for C$_{23}$H$_{16}$ClF$_3$N$_4$O: 457.1 (MH$^+$).

Using the same or analogous synthetic techniques and/or substituting with alternative reagents, the following compound of the invention was prepared:

N-phenyl-N'-[4-(3-phenyl-1H-pyrazol-5-yl)phenyl]urea: $^1$H NMR (400 MHz, DMSO-d$_6$): δ 8.80 (bs, 1H), 8.72 (bs, 1H), 7.81 (d, J=7.2 Hz, 2H), 7.72 (d, J=8.0 Hz, 2H), 7.51 (d, J=8.8 Hz, 2H), 7.44 (m, 3H), 7.29 (m, 3H), 7.08 (s, 1H), 6.96 (t, J=7.2 Hz, 1H); MS (EI) for C$_{22}$H$_{18}$N$_4$O: 355.1 (MH$^+$).

Example 8

N-[4-chloro-3-(trifluoromethyl)phenyl]-N'-(4-{3-[4-(4-ethylpiperazin-1-yl)phenyl]-1H-pyrazol-5-yl}phenyl)urea

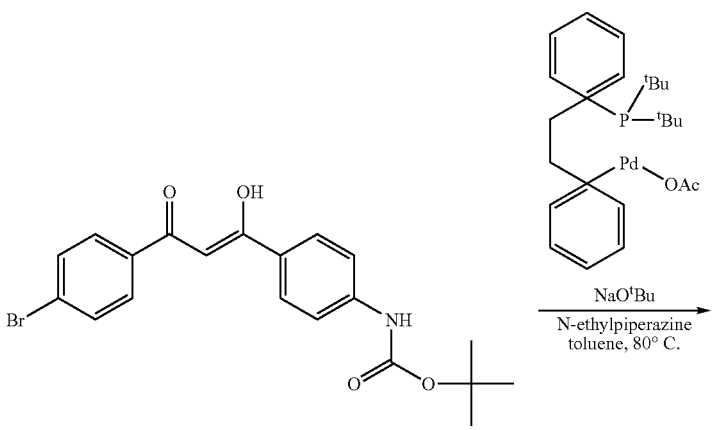

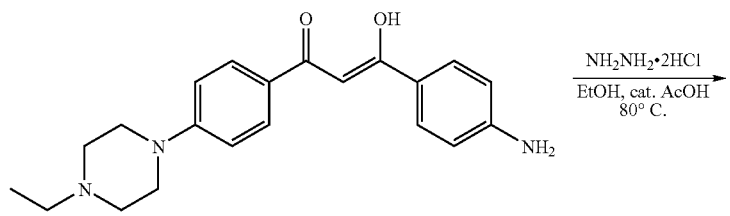

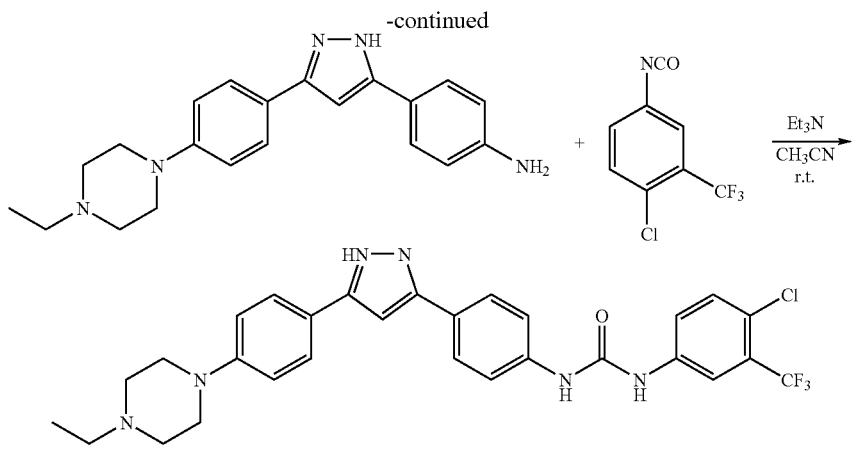

(2Z)-3-(4-Aminophenyl)-1-[4-(4-ethylpiperazin-1-yl)phenyl]-3-hydroxyprop-2-en-1-one: N-Ethylpiperazine (334 μL, 2.62 mmol) was added to a sealed tube charged with {4-[3-(4-bromophenyl)-1-hydroxy-3-oxo-propenyl]-phenyl}-carbamic acid tert-butyl ester (0.842 g, 2.01 mmol), NaOtBu (0.483 g, 5.03 mmol) and acetato(2'-di-t-butylphosphino-1,1'-biphenyl-2-yl)palladium (0.140 g, 0.30 mmol, 15 mol %) in anhydrous toluene (10 mL). The reaction tube was sealed and heated to 110° C. After 24 hours, the reaction was cooled to room temperature, diluted with methanol and filtered though a celite pad. The filtrate was concentrated in vacuo and the residue purified on reverse phase HPLC using water-acetonitrile gradient (0.1% TFA) to provide 3-(4-aminophenyl)-3-hydroxy-1-[4-(4-ethylpiperazin-1-yl)-phenyl]-propenone (208 mg, 32% yield) as an off-white solid. Note that the BOC group was removed during the purification: $^1$H NMR (400 MHz, CD$_3$OD): δ 7.97 (m, 2H), 7.85 (m, 2H), 7.10 (m, 2H), 6.84 (s, 1H), 6.78 (m, 2H), 4.11 (bd, J=12.0 Hz, 2H), 3.69 (bd, J=10.4 Hz, 2H), 3.32-3.22 (m, 6H), 1.41 (t, J=5.4 Hz, 3H); MS (EI) for C$_{21}$H$_{25}$N$_3$O$_2$: 352.1 (MH$^+$).

4-{3-[4-(4-ethylpiperazin-1-yl)phenyl]-1H-pyrazol-5-yl}aniline:

Hydrazine dihydrochloride (0.093 g, 0.89 mmol) was added to a sealed tube charged with the above product (0.208 g, 0.59 mmol) in absolute ethanol (5 mL) and a catalytic amount of acetic acid. The reaction tube was sealed and heated to 85° C. After 12 hours the reaction was cooled to room temperature and concentrated in vacuo. The residue was dissolved in a small amount of methanol and precipitated with a solution of methylene chloride:hexanes (1:1). The solid was collected by vacuum filtration to provide the corresponding pyrazole product (174 mg, 85% yield) as a yellow solid: $^1$H NMR (400 MHz, CD$_3$OD): δ 8.01 (m, 2H), 7.77 (m, 2H), 7.51 (m, 2H), 7.24 (s, 1H), 7.16 (m, 2H), 4.03 (bd, J=12.0 Hz, 2H), 3.70 (bd, J=10.4 Hz, 2H), 3.32-3.22 (m, 6H), 1.42 (t, J=5.4 Hz, 3H); MS (EI) for C$_{21}$H$_{25}$N$_5$: 348.1 (MH$^+$)

N-[4-Chloro-3-(trifluoromethyl)phenyl]-N'-(4-{3-[4-(4-ethylpiperazin-1-yl)phenyl]-1H-pyrazol-5-yl}phenyl)urea: Triethylamine (35 μL, 0.25 mmol) was added to a suspension of the above pyrazole (0.067 g, 0.19 mmol) and 4-chloro-3-trifluoromethyl-phenylisocyanate (0.055 g, 0.25 mmol) in anhydrous acetonitrile (2.0 mL) at room temperature. After twelve hours the reaction was concentrated in vacuo and purified on reverse phase HPLC using water-acetonitrile gradient (0.1% TFA) to provide the title compound (8 mg, 8% yield) as a white solid: $^1$H NMR (400 MHz, CD$_3$OD): δ 8.02 (bd, J=2.8 Hz, 1H), 7.78 (m, 4H), 7.64 (bd, J=2.8 Hz, 1H), 7.61 (m, 2H), 7.51 (d, J=10.8 Hz, 1H), 7.15 (m, 2H), 7.11 (bs, 1H), 4.03 (bd, J=12.0 Hz, 2H), 3.71 (bd, J=10.4 Hz, 2H), 3.31 (m, 4H), 3.13 (m, 2H), 1.42 (t, J=5.4 Hz, 3H); MS (EI) for C$_{29}$H$_{28}$ClF$_3$N$_6$O: 569.2 (MH$^+$).

Using the same or analogous synthetic techniques and/or substituting with alternative reagents, the following compounds of the invention were prepared:

N-[4-chloro-3-(trifluoromethyl)phenyl]-N'-(4-{3-[4-(4-methylpiperazin-1-yl)phenyl-]-1H-pyrazol-5-yl}phenyl)urea: $^1$H NMR (400 MHz, DMSO-d$_6$): δ 8.07 (d, J=5.6 Hz, 1H), 7.74 (m, 4H), 7.61 (dd, J=8.4, 2.4 Hz, 1H), 7.54 (m, 3H), 7.07 (m, 3H), 3.92 (bd, J=13.2 Hz, 2H), 3.52 (bd, J=12.0 Hz, 2H), 3.17 (dt, J=11.2, 2.0 Hz, 2H), 3.07 (bt, J=12.0 Hz, 2H), 2.86 (s, 3H); MS (EI) for C$_{28}$H$_{26}$ClF$_3$N$_6$O: 556.2 (MH$^+$).

N-(4-{3-[4-(4-methylpiperazin-1-yl)phenyl]-1H-pyrazol-5-yl}phenyl)-N'-(2-phenylethyl)ethanediamide: $^1$H NMR (400 MHz, DMSO-d$_6$): δ 7.85-7.58 (m, 7H), 7.26-7.13 (m, 6H), 6.92 (m, 4H), 3.81 (bs, 1H), 3.44 (bt, J=6.8 Hz, 2H), 3.17 (m, 5H), 2.82 (t, J=7.6 Hz, 2H), 2.48 (m, 2H), 2.23 (s, 3H); MS (EI) for C$_{30}$H$_{32}$N$_6$O$_2$: 509.3 (MH$^+$).

N-[4-chloro-3-(trifluoromethyl)phenyl]-N'-(4-{3-[3-(4-methylpiperazin-1-yl)phenyl]-1H-pyrazol-5-yl}phenyl)urea: $^1$H NMR (400 MHz, CD$_3$OD): δ 8.10 (d, J=2.4 Hz, 1H), 7.81 (m, 2H), 7.67 (dd, J=8.8, 2.4 Hz, 1H), 7.62 (m, 2H), 7.57 (d, J=8.8 Hz, 1H), 7.53 (bs, 1H), 7.42 (m, 2H), 7.15 (s, 1H), 7.09 (m, 1H), 4.01 (bd, J=13.2 Hz, 2H), 3.65 (bd, J=12.0 Hz, 2H), 3.32 (m, 2H), 3.17 (dt, J=13.2, 1.6 Hz, 2H), 2.99 (s, 3H); MS (EI) for C$_{28}$H$_{26}$ClF$_3$N$_6$O: 555.2 (MH$^+$).

N-(2,4-difluorophenyl)-N'-(4-{3-[4-(4-methylpiperazin-1-yl)phenyl]-1H-pyrazol-5-yl}phenyl)urea: $^1$H NMR (400 MHz, DMSO-d$_6$): δ 8.09 (m, 1H), 7.73 (m, 4H), 7.51 (m, 2H), 7.28 (m, 1H), 7.07 (m, 2H), 7.03 (m, 1H), 7.00 (s, 1H), 3.92 (bd, J=12.8 Hz, 2H), 3.52 (bd, J=12.8 Hz, 2H), 3.17 (dt, J=12.4, 2.4 Hz, 2H), 3.05 (dt, J=12.4, 2.4 Hz, 2H), 2.86 (s, 3H); MS (EI) for C$_{27}$H$_{26}$F$_2$N$_6$O: 489.2 (MH$^+$).

N-[2,4-bis(methyloxy)phenyl]-N'-(4-{5-[4-(4-methylpiperazine-1-yl)phenyl]-1H-pyrazol-3-yl}phenyl)urea: $^1$H NMR (400 MHz, CH$_3$OH-d4): δ 8.80 (m, 2H), 7.70 (m, 1H), 7.50 (m, 2H), 6.50 (m, 5H), 3.95 (s, 3H), 3.85 (s, 3H), 3.78 (m, 4H), 2.68 (m, 4H), 2.40 (s, 3H); MS (EI) for C$_{29}$H$_{32}$N$_6$O$_3$: 513.2 (MH$^+$).

N-[5-chloro-2-(methyloxy)phenyl]-N'-(4-{5-[4-(4-methylpiperazine-1-yl)phenyl]-1H-pyrazol-3-yl}phenyl)urea: $^1$H NMR (400 MHz, CH$_3$OH-d4): δ 8.25 (s, 1H), 7.70 (dd, 4H), 7.60 (d, 2H), 7.00 (d, 2H), 6.80 (s, 1H), 3.95 (s, 3H), 3.38 (m, 4H), 2.60 (m, 4H), 2.40 (s, 3H); MS (EI) for C$_{28}$H$_{29}$ClN$_6$O$_2$: 517.2 (M)

N-(3,4-dimethylphenyl)-N'-(4-{5-[4-(4-methylpiperazine-1-yl)phenyl]-1H-pyrazol-3-yl}phenyl)urea: ¹H NMR (400 MHz, DMSO-d6): δ 13.0 (s, 1H), 8.78 (s, 1H), 8.60 (s, 1H), 7.60 (m, 7H), 7.30 (m, 5H), 3.20 (m, 4H), 2.50 (m, 4H), 2.10 (m, 9H); MS (EI) for $C_{29}H_{32}N_6O_2$: 481.3 (MH⁺).

N-(4-{5-[4-(4-methylpiperazine-1-yl)phenyl]-1H-pyrazol-3-yl}phenyl)-N'-[4-(phenyloxy)phenylurea: ¹H NMR (400 MHz, DMSO-d6): δ 8.78 (br, 2H), 7.70 (m, 3H), 7.50 (m, 3H), 7.40 (m, 3H), 7.00 (m, 8H), 3.20 (m, 4H), 2.50 (m, 4H), 2.20 (s, 3H); MS (EI) for $C_{33}H_{32}N_6O_2$: 545.3 (MH⁺).

N-(2,3-dihyro-1,4-benzodioxin-6-yl)-N'-(4-{5-[4-(4-methylpiperazine-1-yl)phenyl]-1H-pyrazol-3-yl}phenyl)urea: ¹H NMR (400 MHz, CH₃OH-d4): δ 7.70 (m, 4H), 7.50 (d, 2H), 7.10 (m, 3H), 6.90 (s, 1H), 6.80 (m, 2H), 4.20 (m, 4H), 3.90 (m, 2H), 3.60 (m, 2H), 3.30 (m, 2H), 3.10 (m, 2H), 2.90 (s, 3H); MS (EI) for $C_{29}H_{30}N_6O_3$: 511.3 (MH⁺).

N-(5-fluoro-2-methylphenyl)-N'-(4-{5-[4-(4-methylpiperazine-1-yl)phenyl]-1H-pyrazol-3-yl}phenyl)urea: ¹H NMR (400 MHz, CH₃OH-d4): δ 7.70 (m, 5H), 7.60 (d, 2H), 7.20 (m, 3H), 6.90 (s, 1H), 6.80 (m, 1H), 4.00 (m, 2H), 3.60 (m, 2H), 3.30 (m, 2H), 3.10 (m, 2H), 2.90 (s, 3H), 2.25 (s, 3H); MS (EI) for $C_{28}H_{29}FN_6O$: 485.3 (MH⁺).

Example 9

N-[4-Chloro-3-(trifluoromethyl)phenyl]-N'-(4-{3-[5-(4-ethylpiperazin-yl)-1H-benzimidazol-2-yl]-1H-pyrazol-3-yl}phenyl)urea trile gradient (0.1% TFA) to provide the product (87 mg, 99% yield) as a light purple solid. Note that the BOC group was removed under the purification conditions: ¹H NMR (400 MHz, CDCl₃): δ 7.90 (m, 2H), 7.71 (d, J=8.8 Hz, 1H), 7.46 (m, 2H), 7.42 (dd, J=9.2, 2.0 Hz, 1H), 7.41 (s, 1H), 7.30 (d, J=2.4 Hz, 1H), 4.01 (bd, J=12.0 Hz, 2H), 3.74 (bd, J=10.4 Hz, 2H), 3.35-3.27 (m, 4H), 3.23 (m, 2H), 1.44 (t, J=7.2 Hz, 3H); MS (EI) for $C_{22}H_{25}N_7$: 388.2 (MH⁺).

N-[4-Chloro-3-(trifluoromethyl)phenyl]-N'-(4-{3-[5-(4-ethylpiperazin-yl)-1H-benzimidazol-2-yl]-1H-pyrazol-3-yl}phenyl)urea: Triethylamine (250 μL, 1.78 mmol) was added to a solution of the above pyrazole (0.087 g, 0.18 mmol) and 4-chloro-3-trifluoromethyl-phenylisocyanate (0.039 g, 0.18 mmol) in anhydrous DMSO (2.0 mL) at room temperature. After twelve hours the reaction was concentrated in vacuo and purified on reverse phase HPLC using water-acetonitrile gradient (0.1% TFA) to provide the title compound (46 mg, 43% yield) as an off-white solid: ¹H NMR (400 MHz, DMSO-d₆): δ 10.81 (bs, 1H), 9.95 (s, 1H), 9.69 (s, 1H), 8.14 (s, 1H), 7.78 (m, 2H), 7.69 (d, J=8.8 Hz, 1H), 7.66 (m, 5H), 7.54 (s, 1H), 7.36 (bd, J=9.2 Hz, 1H), 7.16 (s, 1H), 3.91 (bd, J=11.2 Hz, 2H), 3.60 (bd, J=10.8 Hz, 2H), 3.19 (m, 6H), 1.30 (t, J=7.2 Hz, 3H); MS (EI) for $C_{30}H_{28}ClF_3N_8O$: 609.3 (M+).

Using the same or analogous synthetic techniques and/or substituting with alternative reagents, the following compounds of the invention were prepared:

N-(2,4-difluorophenyl)-N'-(4-{3-[6-(4-ethylpiperazin-1-yl)-1H-benzimidazol-2-yl]-1H-pyrazol-3-yl}phenyl)urea:

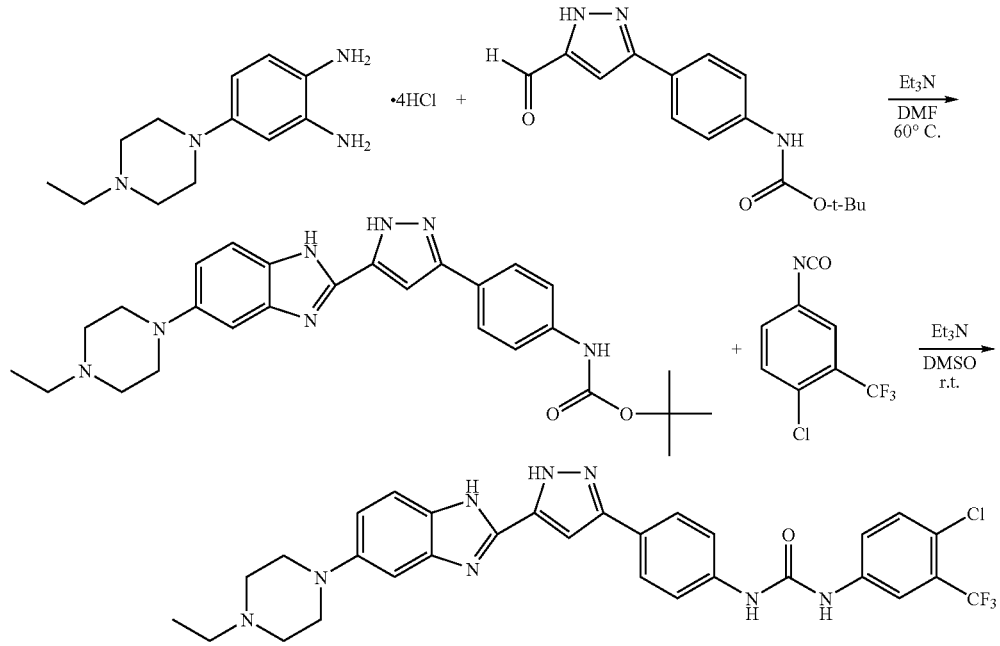

4-{5-[5-(4-Ethylpiperazin-1-yl)-1H-benzimidazol-2-yl]-1H-pyrazol-3-yl}aniline: Triethylamine (509 μL, 3.62 mmol) was added to a solution of 4-(4-ethylpiperazin-1-yl)-benzene-1,2-diamine as the tetra-hydrochloride salt in anhydrous DMF (4 mL). After five minutes, a solution of [4-(5-formyl-1H-pyrazol-3-yl)phenyl]carbamic acid tert-butyl ester in anhydrous DMF (2 mL) was added to the diamine. The reaction flask was left open to the air and heated to 65° C. After twelve hours the reaction was concentrated in vacuo and the residue purified on reverse phase HPLC using water-acetoni- ¹H NMR (400 MHz, DMSO-d₆): δ 8.04 (m, 1H), 7.69 (m, 2H), 7.64 (d, J=9.2 Hz, 1H), 7.54 (m, 2H), 7.34 (s, 1H), 7.31 (dd, J=9.2, 2.0 Hz, 1H), 7.17 (d, J=2.0 Hz, 1H), 7.11 (m, 1H), 6.93 (m, 1H), 3.88 (bd, J=10.8 Hz, 2H), 3.61 (bd, J=12.4 Hz, 2H), 3.18 (m, 6H), 1.30 (t, J=7.2 Hz, 3H); MS (EI) for $C_{29}H_{28}F_2N_8O$: 543.3 (MH⁺).

N-(3-ethylphenyl)-N'-(4-{3-[5-(4-ethylpiperazin-1-yl)-1H-benzimidazol-2-yl]-1H-pyrazol-3-yl}phenyl)urea: ¹H NMR (400 MHz, DMSO-d₆): δ 7.77 (m, 2H), 7.71 (d, J=8.8 Hz, 1H), 7.66 (m, 2H), 7.51 (s, 1H), 7.39 (dd, J=9.2, 1.6 Hz, 1H), 7.35 (bs, 1H), 7.31 (bd, J=8.0 Hz, 1H), 7.22 (m, 2H), 6.85 (bd, J=5.6 Hz, 1H), 3.94 (bd, J=9.2 Hz, 2H), 3.65 (bd, J=8.4 Hz, 2H), 3.22 (m, 4H), 3.14 (m, 2H), 3.10 (q, J=7.2 Hz, 2H), 1.21 (t, J=7.2 Hz, 3H), 1.20 (t, J=7.6 Hz, 3H); MS (EI) for $C_{31}H_{34}N_8O$: 535.3 (MH$^+$).

N-(4-{3-[5-(4-ethylpiperazin-1-yl)-1H-benzimidazol-2-yl]-1H-pyrazol-3-yl}phenyl)-N'-[3-(trifluoromethyl)phenyl]urea: $^1$H NMR (400 MHz, DMSO-d$_6$): δ 11.0 (bs, 1H), 9.91 (s, 1H), 9.77 (s, 1H), 8.04 (bs, 1H), 7.78 (m, 2H), 7.70 (d, J=8.8 Hz, 1H), 7.66 (m, 2H), 7.60 (d, J=8.4 Hz, 1H), 7.58 (s, 1H), 7.53 (t, J=8.0 Hz, 1H), 7.38 (dd, J=9.2, 4.0, 1H), 7.32 (bd, J=7.6 Hz, 1H), 7.17 (d, J=2.0 Hz, 1H), 3.91 (bd, J=12.4 Hz, 2H), 3.69 (m, 1H), 3.61 (bd, J=10.8 Hz, 2H), 3.48 (m, 1H), 3.21 (m, 4H), 1.31 (t, J=7.2 Hz, 3H); MS (EI) for $C_{30}H_{29}F_3N_8O$: 575.3 (MH$^+$).

N-(1,1-dimethylethyl)-N'-4-{3-[5-(4-ethylpiperazin-1-yl)-1H-benzimidazol-2-yl]-1H-pyrazol-3-yl}phenyl)urea: $^1$H NMR (400 MHz, DMSO-d$_6$): δ 7.67 (d, J=9.2 Hz, 1H), 7.65 (m, 2H), 7.50 (m, 2H), 7.43 (s, 1H), 7.34 (dd, J=9.2, 2.0 Hz, 1H), 7.16 (d, J=2.0, 1H), 3.89 (bd, J=9.2 Hz, 2H), 3.60 (bd, J=8.8 Hz, 2H); 3.17 (m, 6H), 1.29 (t, J=7.2 Hz, 3H), 1.27 (s, 9H); MS (EI) for $C_{27}H_{34}N_8O$: 487.3 (MH$^+$).

Example 10

2-(5-Phenyl-1H-pyrazol-3-yl)-1H-benzimidazole

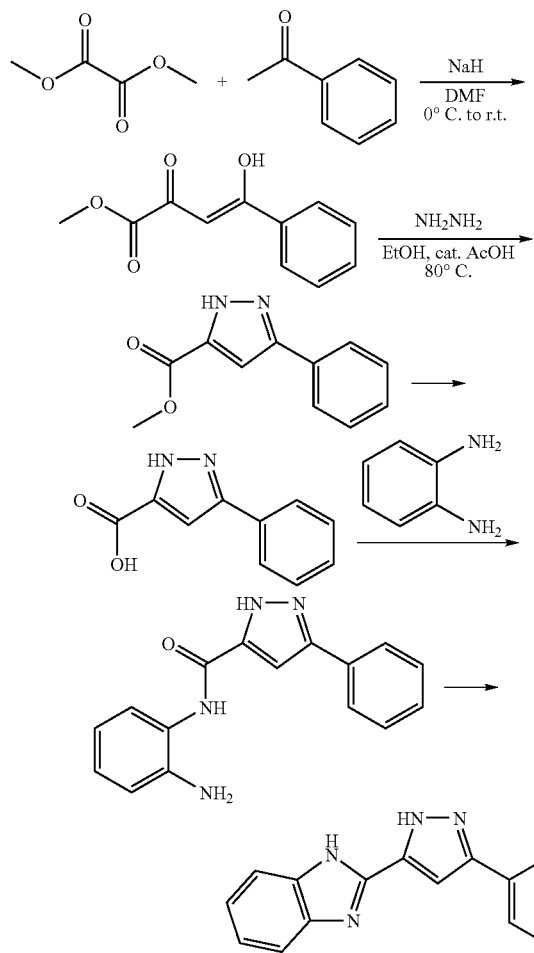

Methyl(2Z)-3-hydroxy-3-phenylprop-2-enoate: To a solution of acetophenone (10.0 g, 83.2 mmol) and dimethyl oxalate (11.8 g, 100.0 mmol) in DMF (80 mL) was added sodium hydride (4.0 g, 100 mmol, 60% oil dispersion). This mixture was stirred for 1 h at room temperature and reacted for 30 min. at 50° C. It was cooled on ice bath, quenched with water saturated with sodium chloride and neutralized with 2N hydrochloric acid. The organic layer was separated and dried with sodium sulfate. After flash column chromatography (30% Ethyl acetate/hexane), the product was obtained as a colorless solid (12.0 g, 70.2% yield): MS (EI) for $C_{11}H_{10}O_4$: 207.06 (MH$^+$).

Methyl 3-phenyl-1H-pyrazole-5-carboxylate: To a solution of 2-hydroxy-4-oxo-4-phenyl-but-2-enoic acid methyl ester (12.0 g, 58.2 mmol) in EtOH (30 ml) was added hydrazine monohydrate (2.84 mL, 58.2 mmol) and the mixture was heated at reflux for 5 h. The reaction mixture was cooled to room temperature and filtered in vacuo. The precipitate was washed with EtOH to give the desired product (6.02 g, 51.5% yield): MS (EI) for $C_{11}H_{10}N_2O_2$: 203.08 (MH$^+$).

3-Phenyl-1H-pyrazole-5-carboxylic acid: To a solution of methyl 3-phenyl-1H-pyrazole-5-carboxylate (6.02 g, 29.8 mmol) in THF and H$_2$O (3:1, 140 mL) was added LiOH (3.42 g, 142.8 mmol) and the mixture was stirred overnight at room temperature. It was poured into 2N HCl solution (150 mL) and extracted with ethyl acetate. After extration, the organic layer was dried over anhydrous sodium sulfate, filtered and concentrated at reduced pressure to afford product (3.2 g, 57.1%): MS (EI) for $C_{10}H_8N_2O_2$: 189.26 (MH$^+$).

N-(2-aminophenyl)-3-phenyl-1H-pyrazole-5-carboxamide: EDCI (288 mg, 1.5 mmol) was added to a solution of 1,2-diaminobenzene (0.141 g, 1.31 mmol), 3-phenyl-1H-pyrazole-5-carboxylic acid (188 mg, 1.0 mmol) and HOBT (203 mg, 1.5 mmol) in anhydrous DMF (5 mL). The reaction was stirred under nitrogen at room temperature. After twelve hours the reaction was concentrated in vacuo and precipitated from methanol with a small amount of water. The solid was collected by vacuum filtration and further purified on reverse phase HPLC using water-acetonitrile gradient (0.1% TFA) to provide the corresponding amide (60 mg, 38% yield).

2-(3-Phenyl-1H-pyrazol-5-yl)-1H-benzimidazole: Glacial acetic acid (1.0 mL) was added to a sealed tube charged with a solution of the amide (60 mg, 0.38 mmol) in xylenes (1.0 mL) and heated to 100° C. After twelve hours the reaction was cooled to room temperature and concentrated in vacuo. The residue was purified on reverse phase HPLC using water-acetonitrile gradient (0.1% TFA) to provide the title benzimidazole (26 mg, 25% yield) as a white solid: $^1$H NMR (400 MHz, DMSO-d$_6$): δ 13.76 (d, 1H), 12.90 (s, 1H), 7.87 (m, 2H), 7.52 (m, 4H), 7.41 (m, 1H), 6.94 (m, 1H), 7.33 (s, 1H), 7.20 (m, 2H); MS (EI) for $C_{16}H_{12}N_4$: 261.2 (MH$^+$).

Example 11

N-{4-[3-(1H-Benzimidazol-2-yl)-1H-pyrazol-5-yl]phenyl}-N'-phenylurea

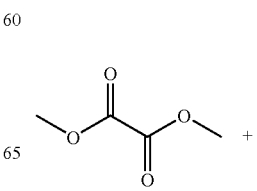

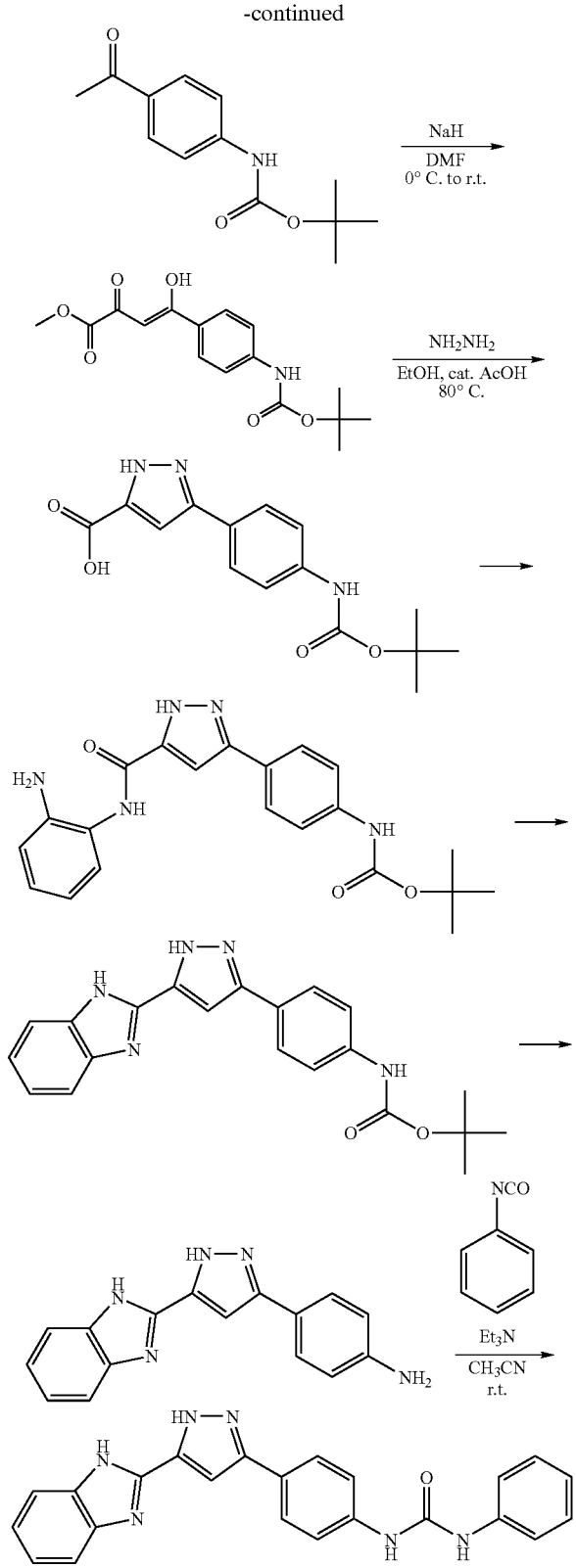

none, 5.44 g, 23.1 mmol) in anhydrous DMF (50 mL) at 0° C. The reaction mixture was allowed to warm to room temperature overnight and quenched with saturated aqueous NH₄Cl and neutralized with 1M HCl. The reaction was diluted with ethyl acetate (80 mL) and the organic layer washed successively with saturated aqueous NaHCO₃ and brine. The organic phase was separated and dried over Na₂SO₄, filtered, concentrated in vacuo and triturated with chloroform to provide the condensation product (3.77 g, 53.1% yield).

3-[4-({[(1,1-Dimethylethyl)oxy]carbonyl}amino)phenyl]-1H-pyrazole-5-carboxylic acid: Hydrazine monohydrate (0.696 g, 13.89 mmol) was added to a suspension of the above product (3.27 g, 13.89 mmol) in absolute ethanol (46 mL). The reaction mixture was refluxed for 1 hour. The reaction mixture was cooled to room temperature and filtered to provide the desired product (2.76, 65.5% yield): $^1$H NMR (400 MHz, DMSO-$d_6$): δ 9.44 (s, 1H), 7.68 (d, 2H), 7.48 (d, 2H), 6.88 (s, 1H), 1.48 (s, 9H).

1,1-Dimethylethyl[4-(5-{[(2-aminophenyl)amino]carbonyl}-1H-pyrazol-3-yl)phenyl]carbamate: EDCI (0.372 g, 1.94 mmol) was added to a solution of 1,2-diaminobenzene (0.28 g, 2.58 mmol), 3-[4-({[(1,1-dimethylethyl)oxy]carbonyl}amino)phenyl]-1H-pyrazole-5-carboxylic acid (0.392 g, 1.29 mmol) and HOBt (0.262 g, 1.94 mmol) in anhydrous DMF (13 mL). The reaction was stirred under nitrogen at room temperature over. After twelve hours the reaction was concentrated in vacuo and precipitated form methanol with a small amount of water. The solid was collected by vacuum filtration and was submitted to the next step.

1,1-Dimethylethyl{4-[5-(1H-benzimidazol-2-yl)-1H-pyrazol-3-yl]phenyl}carbamate: Glacial acetic acid (1.0 mL) was added to a sealed tube charged with the above amide in xylenes (10.0 mL) and heated to 100° C. After twelve hours the reaction was cooled to room temperature and concentrated in vacuo. The residue was purified on reverse phase HPLC using water-acetonitrile gradient (0.1% TFA) to provide 40 mg of product (29% yield over two steps) as a white solid: 1H NMR (400 MHz, DMSO-$d_6$): δ 9.62 (s, 1H), 7.74 (m, 4H), 7.61 (m, 2H), 7.45 (s, 2H), 7.35 (s, 1H); MS (EI) for $C_{21}H_{21}N_5O_2$: 376.2 (MH⁺)

4-[5-(1H-benzimidazol-2-yl)-1H-pyrazol-3-yl]aniline: To a solution of 1,1-dimethylethyl{4-[5-(1H-benzimidazol-2-yl)-1H-pyrazol-3-yl]phenyl}carbamate (130 mg, 0.266 mmol) in methanol (9.0 mL) was added 4M hydrochloric acid in dioxane (3 mL) solution. The reaction mixture was evaporated in vaccuo and triturated with ethyl acetate to provide product as the hydrochloride salt (95.2 mg, 88% yield).

N-{4-[3-(1H-Benzimidazol-2-yl)-1H-pyrazol-5-yl]phenyl}-N'-phenylurea: Triethylamine (35 µL, 0.25 mmol) was added to a suspension of 4-[3-(1H-benzimidazol-2-yl)-1H-pyrazol-5-yl]aniline (20 mg, 0.064 mmol) and phenyl isocyanate (7.6 mg, 0.064 mmol) in anhydrous acetonitrile (1.0 mL) at room temperature. After twelve hours the reaction was concentrated in vacuo and purified on reverse phase HPLC using water-acetonitrile gradient (0.1% TFA) to provide the title compound (9 mg, 36% yield) as a white solid: $^1$H NMR (400 MHz, DMSO-$d_6$): δ 9.08 (s, 1H), 8.92 (s, 1H), 7.78 (m, 4H), 7.63 (m, 2H), 7.48 (m, 4H), 7.40 (s, 1H), 7.30 (m, 2H), 7.00 (m, 1H); MS (EI) for $C_{23}H_{18}N_6O$: 395.2 (MH⁺).

Using the same or analogous synthetic techniques and/or substituting with alternative reagents, the following compounds of the invention were prepared:

N-{4-[3-(1H-benzimidazol-2-yl)-1H-pyrazol-5-yl]phenyl}-N'-[4-chloro-3-(trifluoromethyl)phenyl]urea: $^1$H NMR (400 MHz, DMSO-$d_6$): δ 9.58 (s, 1H), 9.38 (s, 1H), 8.16 (s, 1H), 7.80 (m, 4H), 7.66 (m, 4H), 7.53 (m, 2H), 7.45 (s, 1H); MS (EI) for $C_{24}H_{16}N_6OF_3Cl$: 497.1 (MH⁺).

Methyl(2Z)-3-[4-({[(1,1-dimethylethyl)oxy]carbonyl}amino)phenyl]-3-hydroxyprop-2-enoate: NaH (60% dispersion, 2.22 g, 55.5 mmol) was added to a solution of dimethyl oxalate (2.73 g, 23.1 mmol) and 1,1-dimethylethyl(4-acetylphenyl)carbamate (N-BOC-4-aminoacetophe- N-{4-[3-(1H-benzimidazol-2-yl)-1H-pyrazol-5-yl]phenyl}-N'-[2-fluoro-5-(trifluoromethyl)phenyl]urea: $^1$H NMR (400 MHz, DMSO-$d_6$): δ 9.73 (s, 1H), 9.14 (d, 1H), 8.64 (dd, 1H), 7.81 (in, 4H), 7.67 (m, 2H), 7.54 (m, 3H), 7.50 (s, 1H); 7.42 (m, 1H): MS (EI) for $C_{24}H_{16}N_6OF_4$: 481.1 (MH$^+$).

Example 12

N-(4-{3-[5-(4-Methylpiperazin-1-yl)-1H-benzimidazol-2-yl]-1H-pyrazol-5-yl}phenyl)-N'-{4-[(trifluoromethyl)oxy]phenyl}urea

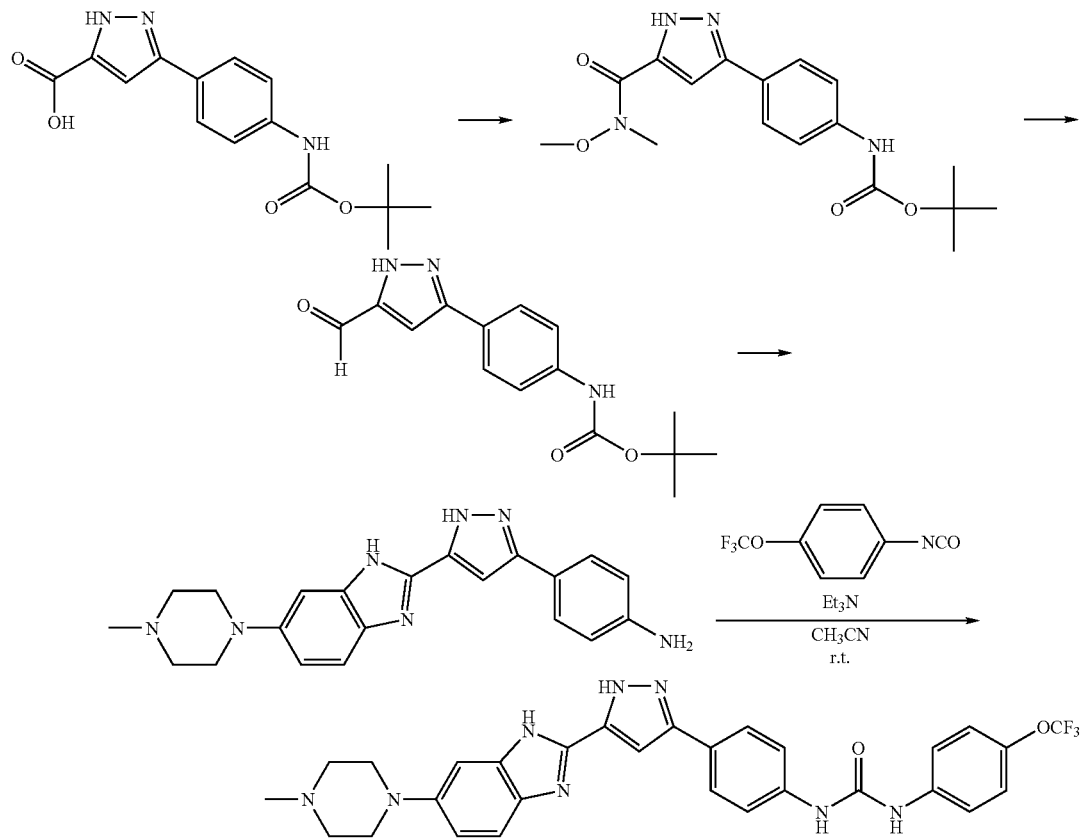

1,1-Dimethylethyl[4-(5-{[methyl(methyloxy)amino]carbonyl}-1H-pyrazol-3-yl)phenyl]carbamate: EDCI (2.56 g, 13.35 mmol) was added to a solution of N,O-dimethylhydroxyamine hydrochloride (0.87 g, 8.9 mmol), 3-[4-({[(1,1-dimethylethyl)oxy]carbonyl}amino)phenyl]-1H-pyrazole-5-carboxylic acid (2.7 g, 8.9 mmol) and HOBt (1.804 g, 13.35 mmol) in anhydrous DMF (30 mL). The reaction was stirred under nitrogen at room temperature. After twelve hours the reaction was concentrated under reduced pressure, diluted with ethyl acetate (200 mL), washed with water. The organic layer was concentrated to afford the crude product (2.46 g, 80% yield).

1,1-Dimethylethyl[4-(5-formyl-1H-pyrazol-3-yl)phenyl]carbamate: To a suspension of lithium aluminum hydride (0.889 g, 23.44 mmol) in THF (50 mL) was added a solution of 1,1-dimethylethyl[4-(5-{[methyl(methyloxy)amino]carbonyl}-1H-pyrazol-3-yl)phenyl]carbamate (2.46 g, 7.1 mmol) in THF (20 mL) at −78° C. After addition, the reaction mixture was stirred at −78° C. for 30 minutes The reaction mixture was then allowed to warm to room temperature overnight. The reaction was quenched with 30% sodium hydroxide aqueous solution, and extracted with ethyl acetate. The organic layer was dried over anhydrous $Na_2SO_4$, filtered, and evaporated under reduced pressure to afford the desired product (1.5 g, 74% yield).

4-{5-[6-(4-Methylpiperazin-1-yl)-1H-benzimidazol-2-yl]-1H-pyrazol-3-yl}aniline: Triethylamine (2.32 g, 23 mmol) was added to a solution of 4-(4-methylpiperazin-1-yl)-benzene-1,2-diamine as the tetra-hydrochloride salt in anhydrous DMF (11 mL) after five minutes, a solution of 1,1-dimethylethyl[4-(5-formyl-1H-pyrazol-3-yl)phenyl]carbamate in anhydrous DMF (2 mL) was added to the diamine. The reaction flask was left open to the air and heated to 65° C. After twelve hours the reaction was concentrated in vacuo and the residue purified on reverse phase HPLC using water-acetonitrile gradient (0.1% TFA) to provide the product (0.60 g, 70% yield). (Note that the BOC group was removed under the purification conditions.)

N-(4-{3-[5-(4-Methylpiperazin-1-yl)-1H-benzimidazol-2-yl]-1H-pyrazol-5-yl}phenyl)-N'-{4-[(trifluoromethyl)oxy]phenyl}urea: To a solution of 4-{5-[6-(4-methylpiperazin-1-yl)-1H-benzimidazol-2-yl]-1H-pyrazol-3-yl}aniline (45 mg, 0.12 mmol) in DMSO (2 mL) were added 1-isocyanato-4-trifluoromethoxybenzene (36.6 mg, 0.18 mmol), triethylamine (36.4 mg, 0.36 mmol) in $CH_3CN$ (1 mL) at room temperature. The reaction mixture was monitored by LC-MS until reaction was complete (1 h). The resulting mixture was concentrated in vacuo and separated by preparative HPLC (0.1% TFA/$CH_3CN$, 0.05% TFA/water). The corresponding fractions were concentrated and dried. The resulting solid was dissolved in MeOH (1 mL) and was added 4N HCl (0.5 mL). The solution was concentrated and repeated three times to afford product (24%, 34.7 mg) as light yellow solid as the hydrochloride salt: $^1$H NMR (400 MHz, DMSO-d6): δ 11.07 (s, 1H), 9.68 (d, 2H), 7.79-7.57 (7H, m), 7.38-7.29 (m, 3H), 7.17 (s, 1H), 3.90 (m, 2H), 3.46 (m, 2H), 3.21 (m, 4H), 2.85 (m, 3H) MS (EI) for $C_{29}H_{27}F_3N_8O_2$: 577.3 (MH$^+$).

Using the same or analogous synthetic techniques and/or substituting with alternative reagents, the following compounds of the invention were prepared:

N-(4-{3-[5-(4-Methylpiperazin-1-yl)-1H-benzimidazol-2-yl]-1H-pyrazol-5-yl}phenyl)-N'-phenylurea: $^1$H NMR (400 MHz, DMSO-d$_6$): δ 10.90 (bs, 1H), 9.51 (s, 1H), 9.29 (s, 1H), 7.77 (d, 2H), 7.70 (d, 1H), 3.91 (m, 2H), 3.69 (m, 2H), 3.19 (m, 4H), 2.86 (s, 3H); MS (EI) for $C_{28}H_{28}N_8O$: 493.2 (MH$^+$).

N-[4-Chloro-3-(trifluoromethyl)phenyl]-N'-(4-{3-[5-(4-methlylpiperazin-1-yl)-1H-benzimidazol-2-yl]-1H-pyrazol-5-yl}phenyl)urea: $^1$H NMR (400 MHz, DMSO-d$_6$): δ 10.41 (bs, 1H), 9.67 (s, 1H), 9.46 (s, 1H), 8.13 (s, 1H), 7.57 (d, 2H), 7.64 (m, 5H), 7.45 (s, 1H), 7.31 (d, 1H), 7.13 (1H), 3.89 (d, 2H), 3.55 (m, 2H), 3.16 (m, 4H), 2.86 (s, 3H); MS (EI) for $C_{29}H_{26}ClF_3N_8O$: 595.2 (MH$^+$).

N-(2,4-Difluorophenyl)-N'-(4-{3-[5-(4-methylpiperazin-1-yl)-1H-benzimidazol-2-yl]-1H-pyrazol-5-yl}phenyl)urea: $^1$H NMR (400 MHz, DMSO-d$_6$): δ 10.87 (bs, 1H), 9.71 (s, 1H), 8.80 (s, 1H), 8.05 (m, 1H), 7.75 (d, 2H), 7.67 (d, 1H), 7.63 (d, 2H), 7.54 (s, 1H), 7.31 (m, 2H), 7.14 (m, 1H), 7.05 (m, 1H), 3.89 (d, 2H), 3.69 (m, 2H), 3.22 (m, 4H), 2.66 (s, 3H); MS (EI) for $C_{28}H_{26}F_2N_8O$: 529.2 (MH$^+$).

N-[3,4-Bis(methyloxy)phenyl]-N'-(4-{3-[5-(4-methylpiperazin-1-yl)-1H-benzimidazol-2-yl]-1H-pyrazol-5-yl}phenyl)urea: $^1$H NMR (400 MHz, DMSO-d$_6$): δ 10.43 (bs, 1H), 9.16 (s, 1H), 8.88 (s, 1H), 7.75 (d, 2H), 7.69 (d, 1H), 7.64 (d, 2H), 7.47 (s, 1H), 7.36 (d, 1H), 7.24 (s, 1H), 7.17 (s, 1H), 6.89 (s, 1H), 3.92 (d, 2H), 3.75 (s, 3H), 3.72 (s, 3H), 3.56 (d, 2H), 3.22 (d, 2H), 3.17 (d, 2H), 2.87 (d, 3H); MS (EI) for $C_{30}H_{32}N_8O_3$: 553.3 (MH$^+$).

N-(4-{3-[5-(4-Methylpiperazin-1-yl)-1H-benzimidazol-2-yl]-1H-pyrazol-5-yl}phenyl)-N'-[3-(trifluoromethyl)phenyl]urea: $^1$H NMR (400 MHz, DMSO-d$_6$): δ 10.81 (bs, 1H), 9.74 (s, 1H), 9.62 (s, 1H), 8.02 (s, 1H), 7.76 (d, 2H), 7.65 (m, 3H), 7.58 (d, 1H), 7.52 (m, 2H), 7.32 (m, 2H), 7.14 (s, 1H), 3.92 (d, 2H), 3.58 (d, 2H), 3.24 (m, 4H), 2.84 (d, 3H); MS (EI) for $C_{29}H_{27}F_3N_8O$: 561.3 (MH$^+$).

N-(4-Chlorophenyl)-N'-(4-{3-[5-(4-methylpiperazin-1-yl)-1H-benzimidazol-2-yl]-1H-pyrazol-5-yl}phenyl)urea: $^1$H NMR (400 MHz, DMSO-d$_6$): δ 10.58 (bs, 1H), 9.40 (s, 1H), 9.35 (s, 1H), 7.70 (d, 2H), 7.68 (d, 1H), 7.64 (d, 2H), 7.51 (d, 2H), 7.49 (d, 1H), 7.34 (m, 3H), 7.16 (s, 1H), 3.91 (d, 2H), 3.55 (d, 2H), 3.17 (m, 4H), 2.86 (d, 3H); MS (EI) for $C_{28}H_{27}ClN_8O$: 527.2 (MH$^+$).

N-(4-Fluorophenyl)-N'-(4-{3-[5-(4-methylpiperazin-1-yl)-1H-benzimidazol-2-yl]-1H-pyrazol-5-yl}phenyl)urea: $^1$H NMR (400 MHz, DMSO-d$_6$): δ 10.92 (bs, 1H), 9.50 (s, 1H), 9.36 (s, 1H), 7.76 (d, 2H), 7.69 (d, 1H), 7.64 (d, 2H), 7.55 (s, 1H), 7.49 (dd, 1H), 7.37 (dd, 1H), 7.15 (d, 2H), 7.12 (s, 1H), 3.91 (d, 2H), 3.55 (d, 2H), 3.17 (m, 4H), 2.86 (d, 3H); MS (EI) for $C_{28}H_{27}FN_8O$: 511.3 (MH$^+$).

N-(3-Fluorophenyl)-N'-(4-{3-[5-(4-methylpiperazin-1-yl)-1H-benzimidazol-2-yl]-1H-pyrazol-5-yl}phenyl)urea: $^1$H NMR (400 MHz, DMSO-d$_6$): δ 10.92 (bs, 1H), 9.63 (s, 1H), 9.62 (s, 1H), 7.83 (d, 2H), 7.68 (d, 1H), 7.65 (d, 2H), 7.53 (m, 2H), 7.34 (dd, 2H), 78.17 (s, 1H), 7.13 (d, 1H), 6.80 (m, 1H), 3.90 (d, 2H), 3.69 (m, 2H), 3.23 (m, 4H), 2.84 (s, 3H); MS (EI) for $C_{28}H_{27}FN_8O$: 511.3 (MH$^+$).

N-(2-Fluorophenyl)-N'-(4-{3-[5-(4-methylpiperazin-1-yl)-1H-benzimidazol-2-yl]-1H-pyrazol-5-yl}phenyl)urea: $^1$H NMR (400 MHz, DMSO-d$_6$): δ 11.14 (bs, 1H), 9.91 (s, 1H), 8.90 (s, 1H), 8.15 (t, 1H), 7.79 (d, 2H), 7.68 (m, 3H), 7.61 (s, 1H), 7.37 (d, 1H), 7.25 (dd, 1H), 7.16 (m, 2H), 7.03 (m, 1H), 3.54 (m, 2H), 3.48 (m, 2H), 3.21 (m, 4H), 2.84 (s, 3H); MS (ED) for $C_{28}H_{27}FN_8O$: 511.3 (MH$^+$).

N-(3,4-Dichlorophenyl)-N'-(4-{3-[5-(4-methylpiperazin-1-yl)-1H-benzimidazol-2-yl]-1H-pyrazol-5-yl}phenyl)urea urea: $^1$H NMR (400 MHz, DMSO-d$_6$): δ 11.05 (bs, 1H), 9.91 (s, 1H), 9.77 (s, 1H), 7.90 (d, 1H), 7.78 (d, 2H), 7.69 (d, 1H), 7.64 (d, 2H), 7.58 (s, 1H), 7.54 (d, 1H), 7.36 (dt, 2H), 7.16 (s, 1H), 3.90 (d, 2H), 3.53 (m, 2H), 3.20 (m, 4H), 2.84 (d, 3H); MS (EI) for $C_{28}H_{26}Cl_2N_8O$: 561.2 (MH$^+$).

N-(4-{3-[5-(4-Methylpiperazin-1-yl)-1H-benzimidazol-2-yl]-1H-pyrazol-5-yl}phenyl)-N'-[4-(phenyloxy)phenyl]urea: $^1$H NMR (400 MHz, CD$_3$OD): δ 7.67-7.61 (m, 3H), 7.55-7.52 (m, 2H), 7.45-7.42 (m, 2H), 7.37-7.30 (m, 3H), 7.24 (m, 1H), 7.19 (s, 1H), 7.09-7.05 (m, 1H), 6.97-6.93 (m, 4H), 3.95-3.89 (d, 2H), 3.75-3.71 (m, 1H), 3.68-3.63 (m, 3H), 3.59-3.56 (m, 1H), 3.23-3.15 (m, 2H), 2.97 (s, 3H); MS (EI) for $C_{34}H_{32}N_8O_2$: 585.3 (MH$^+$).

N-(3,5-Difluorophenyl)-N'-(4-{3-[5-(4-methylpiperazin-1-yl)-1H-benzimidazol-2-yl]-1H-pyrazol-5-yl}phenyl)urea: $^1$H NMR (400 MHz, CD$_3$OD): δ (m, 3H), 7.64-7.61 (m, 2H), 7.43-7.40 (m, 1H), 7.31-7.29 (m, 2H), 7.15-7.12 (m, 2H), 6.60-6.54 (m, 1H), 4.01-3.94 (d, 2H), 3.71-3.65 (m, 2H), 3.39-3.32 (m, 1H), 3.25-3.17 (m, 3H), 3.01 (s, 3H); MS (EI) for $C_{28}H_{26}F_2N_8O$: 529.2 (MH$^+$).

N-[3,5-Bis(trifluoromethyl)phenyl]-N'-(4-{3-[5-(4-methylpiperazin-1-yl)-1H-benzimidazol-2-yl]-1H-pyrazol-5-yl}phenyl)urea: $^1$H NMR (400 MHz, CD$_3$OD): δ 8.11 (s, 2H), 7.75-7.64 (m, 5H), 7.56 (m, 5H), 7.43-7.39 (dd, 1H), 7.30 (s, 2H), 4.01-3.94 (d, 2H), 3.75-3.64 (m, 4H), 3.25-3.17 (m, 2H), 3.01 (s, 3H); MS (EI) for $C_{30}H_{26}F_6N_8O$: 629.2 (MH$^+$).

N-(3-Chlorophenyl)-N'-(4-{3-[5-(4-methylpiperazin-1-yl)-1H-benzimidazol-2-yl]-1H-pyrazol-5-yl}phenyl)urea: $^1$H NMR (400 MHz, CD$_3$OD): δ 7.73-7.66 (m, 4H), 7.63-7.60 (m, 2H), 7.43-7.40 (m, 1H), 7.30-7.25 (m, 4H), 7.04-7.00 (m, 1H), 4.00-3.94 (d, 2H), 3.70-3.65 (m, 2H), 3.39-3.33 (m, 2H), 3.25-3.16 (m, 2H), 3.00 (s, 3H); MS (EI) for $C_{28}H_{27}ClN_8O$: 527.2 (MH$^+$).

N-[3-(Methyloxy)phenyl]-N'-(4-{3-[5-(4-methylpiperazin-1-yl)-1H-benzimidazol-2-yl]-1H-pyrazol-5-yl}phenyl)urea: $^1$H NMR (400 MHz, CD$_3$OD): δ 7.65-7.62 (d, 1H), 7.58-7.55 (d, 2H), 7.49-7.45 (d, 2H), 7.35-7.31 (m, 1H), 7.20-7.13 (m, 4H), 6.95 (6.92 (m, 1H0 6.61-6.58 (m, 1H), 3.92-3.87 (d, 2H), 3.79 (s, 3H), 3.68-3.60 (m, 2H), 3.28-3.13 (m, 4H), 2.94 (s, 3H), MS (EI) for $C_{29}H_{30}N_8O_2$: 523.3 (MH$^+$).

N-(3-Acetylphenyl)-N'-(4-{3-[5-(4-methylpiperazin-1-yl)-1H-benzimidazol-2-yl]-1H-pyrazol-5-yl}phenyl)urea: $^1$H NMR (400 MHz, CD$_3$OD): δ 7.72-7.57 (m, 8H), 7.46-7.38 (m, 2H), 7.29-7.26 (m, 2H), 4.00-3.93 (m, 2H), 3.70-3.64 (m, 4H), 3.25-3.17 (m, 2H), 3.00 (s, 3H), 2.61 (s, 3H); MS (EI) for $C_{30}H_{30}N_8O_2$: 535.3 (MH$^+$).

N-(3,4-Difluorophenyl)-N'-(4-{3-[5-(4-methylpiperazin-1-yl)-1H-benzimidazol-2-yl]-1H-pyrazol-5-yl}phenyl)urea: $^1$H NMR (400 MHz, CD$_3$OD): δ 7.73-7.69 (m, 3H), 7.63-7.58 (m, 3H), 7.43-7.40 (m, 1H), 7.31-7.29 (m, 2H), 7.22-7.15 (m, 1H), 7.10-7.05 (m, 1H), 4.00-3.94 (d, 2H), 3.71-3.56 (m, 3H), 3.40-3.33 (m, 1H), 3.25-3.16 (m, 2H), 3.00 (s, 3H); MS (EI) for $C_{28}H_{26}F_2N_8O$: 529.2 (MH$^+$).

N-[4-Fluoro-3-(trifluoromethyl)phenyl]-N'-(4-{3-[5-(4-methylpiperazin-1-yl)-1H-benzimidazol-2-yl]-1H-pyrazol-5-yl}phenyl)urea: $^1$H NMR (400 MHz, CD$_3$OD): δ 7.95-7.91

(m, 1H), 7.74-7.62 (m, 6H), 7.44-7.40 (m, 1H), 7.31-7.25 (m, 3H), 4.01-3.94 (d, 2H), 3.71-3.56 (m, 3H), 3.40-3.32 (m, 1H), 3.26-3.16 (m, 2H), 3.01 (s, 3H); MS (EI) for $C_{29}H_{26}F_4N_8O$: 579.2 (MH$^+$).

N-[3,5-Bis(methyloxy)phenyl]-N'-(4-{3-[6-(4-methylpiperazin-1-yl)-1H-benzimidazol-2-yl]-1H-pyrazol-5-yl}phenyl)urea: $^1$H NMR (400 MHz, d-MeOH): δ 7.70 (m, 3H), 7.60 (d, 2H), 7.41 (d, 1H), 7.24 (m, 2H), 6.70 (d, 2H), 6.22 (s, 1H), 3.86 (br d, 2H), 3.78 (s, 6H), 3.62 (br d, 2H), 3.30 (m, 4H), 3.02 (s, 3H); MS (EI) for $C_{30}H_{32}N_8O_3$: 590 (MH$^+$).

N-(3-Bromophenyl)-N'-(4-{3-[6-(4-methylpiperazin-1-yl)-1H-benzimidazol-2-yl]-1H-pyrazol-5-yl}phenyl)urea: $^1$H NMR (400 MHz, d-MeOH): δ 7.82 (br t, 1H), 7.72 (br d, 3H), 7.62 (br d, 2H), 7.42 (dd, 1H), 7.35 (m, 3H), 7.18 (m, 2H), 3.90 (br d, 2H), 3.78 (s, 6H), 3.63 (br d, 2H), 3.34 (m, 4H), 3.08 (s, 3H); MS (EI) for $C_{28}H_{27}BrN_8O$: 573 (MH$^+$).

N-(3-Cyanophenyl)-N'-(4-{3-[6-(4-methylpiperazin-1-yl)-1H-benzimidazol-2-yl]-1H-pyrazol-5-yl}phenyl)urea: $^1$H NMR (400 MHz, d-MeOH): δ 8.02 (br s, 1H), 7.61 (m, 6H), 7.51 (t, 1H), 7.34 (m, 4H), 3.90 (br s, 2H), 3.62 (br s, 2H), 3.25 (m, 4H), 3.04 (s, 3H); MS (EI) for $C_{29}H_{27}N_9O$: 518 (MH$^+$).

N-(5-Fluoro-2-methylphenyl)-N'-(4-{3-[6-(4-methylpiperazin-1-yl)-1H-benzimidazol-2-yl]-1H-pyrazol-5-yl}phenyl)urea: $^1$H NMR (400 MHz, d-MeOH): δ 7.72 (m, 5H), 7.40 (d, 1H), 7.31 (d, 2H), 7.20 (t, 1H), 6.72 (t, 1H), 3.98 (br d, 2H), 3.68 (br d, 2H), 3.26 (m, 4H), 3.02 (s, 3H); MS (EI) for $C_{29}H_{29}FN_8O$: 523 (MH$^+$).

N-(4-{3-[6-(4-Methylpiperazin-1-yl)-1H-benzimidazol-2-yl]-1H-pyrazol-5-yl}phenyl)-N'-[4-(trifluoromethyl)phenyl]urea: $^1$H NMR (400 MHz, d-MeOH): δ 7.71 (m, 3H), 7.64 (m, 3H), 7.62 (m, 3H), 7.42 (br d, 1H), 7.29 (m, 2H), 3.92 (d, 2H), 3.72 (d, 2H), 3.32 (m, 4H), 3.04 (s, 3H); MS (EI) for $C_{29}H_{27}FN_8O$: 561 (MH$^+$).

Assays

Kinase assays were performed by measurement of incorporation of γ-$^{33}$P ATP into immobilized myelin basic protein (MBP). High binding white 384 well plates (Greiner) were coated with MBP (Sigma #M-1891) by incubation of 60 ul/well of 20 μg/ml MBP in Tris-buffered saline (TBS; 50 mM Tris pH 8.0, 138 mM NaCl, 2.7 mM KCl) for 24 hours at 4° C. Plates were washed 3× with 100 μl TBS. Kinase reactions were carried out in a total volume of 34 μl in kinase buffer (5 mM Hepes pH 7.6, 15 mM NaCl, 0.01% bovine gamma globulin (Sigma #I-5506), 10 mM MgCl$_2$, 1 mM DTT, 0.02% TritonX-100). Compound dilutions were performed in DMSO and added to assay wells to a final DMSO concentration of 1%. Each data point was measured in duplicate, and at least two duplicate assays were performed for each individual compound determination. Enzyme was added to final concentrations of 10 nM or 20 nM, for example. A mixture of unlabeled ATP and γ-$^{33}$P ATP was added to start the reaction (2×10$^6$ cpm of γ-$^{33}$P ATP per well (3000 Ci/mmole) and either 10 μM or 30 μM unlabeled ATP, typically. The reactions were carried out for 1 hour at room temperature with shaking. Plates were washed 7× with TBS, followed by the addition of 50 μl/well scintillation fluid (Wallac). Plates were read using a Wallac Trilux counter. This is only one format of such assays, various other formats are possible, as known to one of ordinary skill in the art.

The above assay procedure can be used to determine the IC$_{50}$ for inhibition and/or the inhibition constant, K$_i$. The IC$_{50}$ is defined as the concentration of compound required to reduce the enzyme activity by 50% under the conditions of the assay. Exemplary compositions have IC$_{50}$'s of, for example, less than about 100 μM, less than about 10 μM, less than about 1 μM, and further for example having IC$_{50}$'s of less than about 100 nM, and still further, for example, less than about 10 nM. The K$_i$ for a compound may be determined from the IC$_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to equation (1) below; where V is the observed rate, V$_{max}$, is the rate of the free enzyme, T$_0$ is the inhibitor concentration, E$_0$ is the enzyme concentration, and K$_d$ is the dissociation constant of the enzyme-inhibitor complex.

$$V = V_{\max}E_0\left[1 - \frac{(E_0 + I_0 + K_d) - \sqrt{(E_0 + I_0 + K_d)^2 - 4E_0\,I_0}}{2E_0}\right] \quad \text{Equation (1)}$$

Kinase Specific Assays:

Kinase activity and compound inhibition are investigated using one or more of the three assay formats described below. The ATP concentrations for each assay are selected to be close to the Michaelis-Menten constant (K$_M$) for each individual kinase. Dose-response experiments are performed at 10 different inhibitor concentrations in a 384-well plate format. The data are fitted to four-parameter equation (2) below; where Y is the observed signal, X is the inhibitor concentration, Min is the background signal in the absence of enzyme (0% enzyme activity), Max is the signal in the absence of inhibitor (100% enzyme activity), IC$_{50}$ is the inhibitor concentration at 50% enzyme inhibition and H represents the empirical Hill's slope to measure the cooperativity. Typically H is close to unity.

$$Y = \text{Min} + (\text{Max} - \text{Min})/(1 + (X/IC_{50})^H) \quad \text{Equation (2)}$$

$^{33}$P Phosphoryl Transfer Assay:

Greiner 384-well white, clear bottom, high binding plates are coated with 2 μg/well of protein or peptide substrate in a 50 μL volume overnight at ambient temperature. The coating buffer typically contains 40 μg/mL substrate, 22.5 mM Na$_2$CO$_3$, 27.5 mM NaHCO$_3$, 150 mM NaCl and 3 mM NaN$_3$. The coating solution is aspirated and the plates are washed once with 50 μL of assay buffer and padded dry. Subsequently compounds and enzymes are mixed with γ$^{33}$P-ATP (3.3 μCi/nmol) in a total volume of 20 uL in suitable assay buffers. The mixture is incubated at ambient temperature for 1.5-2.5 hrs and terminated by aspiration using a Molecular Devices EMBLA 96-head plate washer. The plates are subsequently washed 6-12 times with PBST or TBS buffer. Scintillation fluid (50 μl/well) is then added, the plates are sealed and activity assessed by liquid scintillation spectrometry using a Perkin Elmer MicroBeta TriLux.

Luciferase-Coupled Chemiluminescent Assay (LCCA):

In the LCCA assays, kinase activity is measured as the percent ATP consumed following the kinase reaction using luciferase-luciferin-coupled chemiluminescence. Greiner 384-well white, clear bottom, medium-binding plates are used for LCCA. Briefly, the kinase reaction is initiated by mixing compounds, ATP and kinase in a 20 uL volume. The mixture is incubated at ambient temperature for 2-4 hrs. At the end of the kinase reaction, a 20 uL luciferase-luciferin mix is added and the chemiluminescent signal is read using a Wallac Victor$^2$ reader. The luciferase-luciferin mix consists of 50 mM HEPES, pH 7.8, 8.5 ug/mL oxalic acid (pH 7.8), 5 (or 50) mM DTT, 0.4% Triton X-100, 0.25 mg/mL coenzyme A, 63 uM AMP, 28 ug/mL luciferin and 40,000 units of light/mL luciferase. For the LCCA assays, total ATP consumption has been standardized to 25-45% and the $IC_{50}$ values correlates well with those determined by radiometric assays.

AlphaScreen

AlphaScreen technology is a proximity assay which utilizes the increase in fluorescent signal occurring when donor and acceptor beads are close in proximity. Biotinylated poly(Glu,Tyr) 4:1 is used as the kinase substrate, in conjunction with streptavidin-coated donor beads and anti-phosphortyrosine antibody PY100-coated acceptor beads. Upon phosphorylation, the peptide substrate can bind to both donor and acceptor beads giving rise to an increase in fluorescence. Compounds, ATP, biotinylated poly(Glu, Tyr) and kinases are mixed in a volume of 20 uL for 1 hr at ambient temperature using Greiner 384-well white clear bottom medium binding plates. Following incubation a 10 uL solution containing 15-30 mg/mL AlphaScreen beads, 75 mM Hepes, pH 7.4, 300 mM NaCl, 120 mM EDTA, 0.3% BSA and 0.03% Tween-20 is added to each well. After 2-16 hr incubation of the beads, plates are read in a Perkin Elmer AlphaQuest reader. The $IC_{50}$ values correlates well with those of radiometric assays.

c-Kit Assay c-Kit biochemical activity was assessed using AlphaScreen™ (Perkin Elmer) technology, described above. Test compounds, ATP, biotinylated poly(Glu, Tyr) and c-Kit kinase were combined in a volume of 20 µL in a 384-well white, medium binding microtiter plate (Greiner). Reaction mixtures were incubated for 1 hr at ambient temperature. Reactions were quenched by addition of 10 uL of 15-30 mg/mL AlphaScreen bead suspension containing 75 mM Hepes, pH 7.4, 300 mM NaCl, 120 mM EDTA, 0.3% BSA and 0.03% Tween-20. After 16 hr incubation at ambient temperature plates were read using an AlphaQuest reader (Perkin Elmer).

flt-3 Assay

Flt-3 biochemical activity was assessed using a Luciferase-Coupled Chemiluminescent Kinase assay (LCCA) format. Kinase activity was measured as the percent ATP remaining following the kinase reaction. Remaining ATP was detected by luciferase-luciferin-coupled chemiluminescence. Specifically, the reaction was initiated by mixing test compounds, 5 µM ATP, 3 µM poly-EY and 5 nM Flt-3 (baculovirus expressed human Flt-3 kinase domain R571-S993) in a 20 uL assay buffer (20 mM Tris-HCL pH7.5, 10 mM $MgCl_2$, 0.01% Triton X-100, 1 mM DTT, 2 mM $MnCl_2$). The mixture is incubated at ambient temperature for 3 hours after which 20 uL luciferase-luciferin mix is added and the chemiluminescent signal read using a Wallac Victor$^2$ reader. The luciferase-luciferin mix consists of 50 mM HEPES, pH 7.8, 8.5 ug/mL oxalic acid (pH 7.8), 5 (or 50) mM DTT, 0.4% Triton X-100, 0.25 mg/mL coenzyme A, 63 uM AMP, 28 ug/mL luciferin and 40,000 units of light/mL luciferase.

Structure Activity Relationships

Table 2 shows structure activity relationship data for exemplary compounds of the invention. Inhibition is indicated as $IC_{50}$ with the following key: A=$IC_{50}$ less than 50 nM, B=$IC_{50}$ greater than 50 nM, but less than 500 nM, C=$IC_{50}$ greater than 500 nM, but less than 5000 nM, and D=$IC_{50}$ equal to, or greater than 5,000 nM. Empty cells indicate lack of data only. Abbreviations for enzymes listed in Table 2 are defined as follows: c-Kit, also called stem cell factor receptor or steel factor receptor; flt-3 refers to fms-like tyrosine kinase-3; EphB4 refers to ephrin receptor tyrosine kinse family member B4; and EGFR refers to epidermal growth factor receptor tyrosine kinase.

TABLE 2

| Entry | Name | c-Kit | flt-3 | EphB4 | EGFR |
|---|---|---|---|---|---|
| 1 | 4-((E)-2-{3-[6-(4-methylpiperazin-1-yl)-1H-benzimidazol-2-yl]-1H-pyrazol-5-yl}ethenyl)phenol | A | A | C | D |
| 2 | N-[4-chloro-3-(trifluoromethyl)phenyl]-N'-(4-{3-[5-(4-ethylpiperazin-1-yl)-1H-benzimidazol-2-yl]-1H-pyrazol-5-yl}phenyl)urea | A | A | D | D |
| 3 | N-(3-ethylphenyl)-N'-(4-{3-[5-(4-ethylpiperazin-1-yl)-1H-benzimidazol-2-yl]-1H-pyrazol-5-yl}phenyl)urea | A | A | C | D |
| 4 | N-(4-{3-[5-(4-ethylpiperazin-1-yl)-1H-benzimidazol-2-yl]-1H-pyrazol-5-yl}phenyl)-N'-[3-(trifluoromethyl)phenyl]urea | A | A | C | D |
| 5 | N-(3-acetylphenyl)-N'-(4-{3-[5-(4-methylpiperazin-1-yl)-1H-benzimidazol-2-yl]-1H-pyrazol-5-yl}phenyl)urea | A | A | C | D |
| 6 | N-(3,4-dichlorophenyl)-N'-(4-{3-[5-(4-methylpiperazin-1-yl)-1H-benzimidazol-2-yl]-1H-pyrazol-5-yl}phenyl)urea | A | A | D | D |
| 7 | N-(3-bromophenyl)-N'-(4-{3-[6-(4-methylpiperazin-1-yl)-1H-benzimidazol-2-yl]-1H-pyrazol-5-yl}phenyl)urea | A | A | D | D |
| 8 | N-[4-fluoro-3-(trifluoromethyl)phenyl]-N'-(4-{3-[5-(4-methylpiperazin-1-yl)-1H-benzimidazol-2-yl]-1H-pyrazol-5-yl}phenyl)urea | A | A | D | D |
| 9 | N-(4-{3-[5-(4-methylpiperazin-1-yl)-1H-benzimidazol-2-yl]-1H-pyrazol-5-yl}phenyl)-N'-[4-(phenyloxy)phenyl]urea | A | A | D | D |
| 10 | N-(3-chlorophenyl)-N'-(4-{3-[5-(4-methylpiperazin-1-yl)-1H-benzimidazol-2-yl]-1H-pyrazol-5-yl}phenyl)urea | A | A | D | D |
| 11 | N-[3,5-bis(methyloxy)phenyl]-N'-(4-{3-[6-(4-methylpiperazin-1-yl)-1H-benzimidazol-2-yl]-1H-pyrazol-5-yl}phenyl)urea | A | A | D | D |

TABLE 2-continued

| Entry | Name | c-Kit | flt-3 | EphB4 | EGFR |
|---|---|---|---|---|---|
| 12 | N-(4-{3-[5-(4-methylpiperazin-1-yl)-1H-benzimidazol-2-yl]-1H-pyrazol-5-yl}phenyl)-N'-{4-[(trifluoromethyl)oxy]phenyl}urea | A | A | D | D |
| 13 | N-(4-{3-[6-(4-methylpiperazin-1-yl)-1H-benzimidazol-2-yl]-1H-pyrazol-5-yl}phenyl)-N'-[4-(trifluoromethyl)phenyl]urea | A | A | | |
| 14 | N-[4-chloro-3-(trifluoromethyl)phenyl]-N'-(4-{3-[5-(4-methylpiperazin-1-yl)-1H-benzimidazol-2-yl]-1H-pyrazol-5-yl}phenyl)urea | A | A | D | D |
| 15 | N-(4-{3-[5-(4-methylpiperazin-1-yl)-1H-benzimidazol-2-yl]-1H-pyrazol-5-yl}phenyl)-N'-[3-(trifluoromethyl)phenyl]urea | A | A | C | D |
| 16 | N-[4-chloro-3-(trifluoromethyl)phenyl]-N'-(4-{3-[4-(4-methylpiperazin-1-yl)phenyl]-1H-pyrazol-5-yl}phenyl)urea | A | A | D | D |
| 17 | N-(3,4-dimethylphenyl)-N'-(4-{5-[4-(4-methylpiperazin-1-yl)phenyl]-1H-pyrazol-3-yl}phenyl)urea | A | A | | |
| 18 | N-(4-chlorophenyl)-N'-(4-{3-[5-(4-methylpiperazin-1-yl)-1H-benzimidazol-2-yl]-1H-pyrazol-5-yl}phenyl)urea | A | A | D | D |
| 19 | N-(3,5-difluorophenyl)-N'-(4-{3-[5-(4-methylpiperazin-1-yl)-1H-benzimidazol-2-yl]-1H-pyrazol-5-yl}phenyl)urea | A | A | D | D |
| 20 | N-[3-(methyloxy)phenyl]-N'-(4-{3-[5-(4-methylpiperazin-1-yl)-1H-benzimidazol-2-yl]-1H-pyrazol-5-yl}phenyl)urea | A | A | D | D |
| 21 | N-[4-chloro-3-(trifluoromethyl)phenyl]-N'-(4-{3-[4-(4-ethylpiperazin-1-yl)phenyl]-1H-pyrazol-5-yl}phenyl)urea | A | A | D | D |
| 22 | N-(3-fluorophenyl)-N'-(4-{3-[5-(4-methylpiperazin-1-yl)-1H-benzimidazol-2-yl]-1H-pyrazol-5-yl}phenyl)urea | A | A | D | D |
| 23 | N-(4-fluorophenyl)-N'-(4-{3-[5-(4-methylpiperazin-1-yl)-1H-benzimidazol-2-yl]-1H-pyrazol-5-yl}phenyl)urea | A | A | D | D |
| 24 | N-(3-cyanophenyl)-N'-(4-{3-[6-(4-methylpiperazin-1-yl)-1H-benzimidazol-2-yl]-1H-pyrazol-5-yl}phenyl)urea | A | A | | |
| 25 | N-(3,4-difluorophenyl)-N'-(4-{3-[5-(4-methylpiperazin-1-yl)-1H-benzimidazol-2-yl]-1H-pyrazol-5-yl}phenyl)urea | A | A | D | D |
| 26 | N-[3,4-bis(methyloxy)phenyl]-N'-(4-{3-[5-(4-methylpiperazin-1-yl)-1H-benzimidazol-2-yl]-1H-pyrazol-5-yl}phenyl)urea | A | A | | |
| 27 | N-[5-chloro-2-(methyloxy)phenyl]-N'-(4-{5-[4-(4-methylpiperazin-1-yl)phenyl]-1H-pyrazol-3-yl}phenyl)urea | A | A | | |
| 28 | N-(4-{5-[4-(4-methylpiperazin-1-yl)phenyl]-1H-pyrazol-3-yl}phenyl)-N'-[4-(phenyloxy)phenyl]urea | A | A | | |
| 29 | N-(2,4-difluorophenyl)-N'-(4-{3-[6-(4-ethylpiperazin-1-yl)-1H-benzimidazol-2-yl]-1H-pyrazol-5-yl}phenyl)urea | A | A | D | D |
| 30 | N-{4-[3-(1H-benzimidazol-2-yl)-1H-pyrazol-5-yl]phenyl}-N'-[4-chloro-3-(trifluoromethyl)phenyl]urea | A | A | D | D |
| 31 | N-{4-[3-(1H-benzimidazol-2-yl)-1H-pyrazol-5-yl]phenyl}-N'-[2-fluoro-5-(trifluoromethyl)phenyl]urea | A | A | D | D |
| 32 | N-(2,4-difluorophenyl)-N'-(4-{3-[5-(4-methylpiperazin-1-yl)-1H-benzimidazol-2-yl]-1H-pyrazol-5-yl}phenyl)urea | A | A | D | D |
| 33 | N-{4-[3-(1H-benzimidazol-2-yl)-1H-pyrazol-5-yl]phenyl}-N'-phenylurea | A | 5000 | D | D |
| 34 | N-[3,5-bis(trifluoromethyl)phenyl]-N'-(4-{3-[5-(4-methylpiperazin-1-yl)-1H-benzimidazol-2-yl]-1H-pyrazol-5-yl}phenyl)urea | A | A | C | D |
| 35 | N-(2-fluorophenyl)-N'-(4-{3-[5-(4-methylpiperazin-1-yl)-1H-benzimidazol-2-yl]-1H-pyrazol-5-yl}phenyl)urea | A | A | D | D |
| 36 | 4-((E)-2-{5-[(E)-2-phenylethenyl]-1H-pyrazol-3-yl}ethenyl)phenol | A | A | D | D |
| 37 | 2-(methyloxy)-4-((E)-2-{5-[(E)-2-phenylethenyl]-1H-pyrazol-3-yl}ethenyl)phenol | A | A | C | D |

TABLE 2-continued

| Entry | Name | c-Kit | flt-3 | EphB4 | EGFR |
|---|---|---|---|---|---|
| 38 | N-(5-fluoro-2-methylphenyl)-N'-(4-{3-[6-(4-methylpiperazin-1-yl)-1H-benzimidazol-2-yl]-1H-pyrazol-5-yl}phenyl)urea | A | A | | |
| 39 | N-(4-{3-[5-(4-methylpiperazin-1-yl)-1H-benzimidazol-2-yl]-1H-pyrazol-5-yl}phenyl)-N'-phenylurea | B | A | D | D |
| 40 | N-[4-chloro-3-(trifluoromethyl)phenyl]-N'-(4-{3-[3-(4-methylpiperazin-1-yl)phenyl]-1H-pyrazol-5-yl}phenyl)urea | B | A | | |
| 41 | N-(2,4-difluorophenyl)-N'-(4-{3-[4-(4-methylpiperazin-1-yl)phenyl]-1H-pyrazol-5-yl}phenyl)urea | B | A | D | D |
| 42 | N-(2,3-dihydro-1,4-benzodioxin-6-yl)-N'-(4-{5-[4-(4-methylpiperazin-1-yl)phenyl]-1H-pyrazol-3-yl}phenyl)urea | B | A | D | D |
| 43 | N-[2,4-bis(methyloxy)phenyl]-N'-(4-{5-[4-(4-methylpiperazin-1-yl)phenyl]-1H-pyrazol-3-yl}phenyl)urea | B | A | | |
| 44 | 4-((E)-2-{3-[(E)-2-(4-fluorophenyl)ethenyl]-1H-pyrazol-5-yl}ethenyl)-2-(methyloxy)phenol | B | A | D | D |
| 45 | 4-{(E)-2-[3-(1-benzofuran-2-yl)-1H-pyrazol-5-yl]ethenyl}phenol | B | B | D | D |
| 46 | N-(4-{3-[4-(4-methylpiperazin-1-yl)phenyl]-1H-pyrazol-5-yl}phenyl)-N'-(2-phenylethyl)ethanediamide | B | D | C | D |
| 47 | 4-{(E)-2-[3-(1H-benzimidazol-2-yl)-1H-pyrazol-5-yl]ethenyl}phenol | B | A | C | D |
| 48 | 4-((E)-2-{3-[(E)-2-(4-chlorophenyl)ethenyl]-1H-pyrazol-5-yl}ethenyl)-2-(methyloxy)phenol | B | A | D | D |
| 49 | 4-{(E)-2-[3-(1-benzothien-2-yl)-1H-pyrazol-5-yl]ethenyl}phenol | B | B | D | D |
| 50 | N-[4-chloro-3-(trifluoromethyl)phenyl]-N'-[4-(3-phenyl-1H-pyrazol-5-yl)phenyl]urea | B | B | D | D |
| 51 | 4-((E)-2-{3-[4-(4-methylpiperazin-1-yl)phenyl]-1H-pyrazol-5-yl}ethenyl)phenol | B | A | D | D |
| 52 | 1,1-dimethylethyl{4-[3-(1H-benzimidazol-2-yl)-1H-pyrazol-5-yl]phenyl}carbamate | B | C | | |
| 53 | N-(5-fluoro-2-methylphenyl)-N'-(4-{5-[4-(4-methylpiperazin-1-yl)phenyl]-1H-pyrazol-3-yl}phenyl)urea | B | B | D | D |
| 54 | 4-[(E)-2-(3-phenyl-1H-pyrazol-5-yl)ethenyl]phenol | B | A | D | D |
| 55 | 2-(methyloxy)-4-[(E)-2-(5-phenyl-1H-pyrazol-3-yl)ethenyl]phenol | B | B | D | D |
| 56 | 4-[(E)-2-(5-naphthalen-2-yl-1H-pyrazol-3-yl)ethenyl]phenol | B | B | D | D |
| 57 | 4-{(E)-2-[5-(2-fluorophenyl)-1H-pyrazol-3-yl]ethenyl}phenol | B | B | D | D |
| 58 | 4-((E)-2-{3-[3-(4-methylpiperazin-1-yl)phenyl]-1H-pyrazol-5-yl}ethenyl)phenol | B | B | D | D |
| 59 | 4-((E)-2-{3-[(E)-2-(2,4-difluorophenyl)ethenyl]-1H-pyrazol-5-yl}ethenyl)-2-(methyloxy)phenol | B | A | D | D |
| 60 | 4-{(E)-2-[5-(4-fluorophenyl)-1H-pyrazol-3-yl]ethenyl}phenol | B | A | D | D |
| 61 | 4-{(E)-2-[3-(4-chlorophenyl)-1H-pyrazol-5-yl]ethenyl}phenol | C | B | D | D |
| 62 | 4-[(E)-2-(5-pyridin-2-yl-1H-pyrazol-3-yl)ethenyl]phenol | C | B | | |
| 63 | 4-{(E)-2-[3-(5-chloro-1-benzofuran-2-yl)-1H-pyrazol-5-yl]ethenyl}phenol | C | B | | |
| 64 | N-(1,1-dimethylethyl)-N'-(4-{3-[5-(4-ethylpiperazin-1-yl)-1H-benzimidazol-2-yl]-1H-pyrazol-5-yl}phenyl)urea | C | C | | |
| 65 | 4-[(E)-2-(3-pyridin-4-yl-1H-pyrazol-5-yl)ethenyl]phenol | C | B | | |
| 66 | 4-{(E)-2-[3-(3-chlorophenyl)-1H-pyrazol-5-yl]ethenyl}phenol | C | C | | |
| 67 | 4-((E)-2-{5-[2-(methyloxy)phenyl]-1H-pyrazol-3-yl}ethenyl)phenol | C | C | | |
| 68 | 4-{(E)-2-[3-(2-chlorophenyl)-1H-pyrazol-5-yl]ethenyl}phenol | C | B | | |
| 69 | 4-[(E)-2-(3-pyridin-3-yl-1H-pyrazol-5-yl)ethenyl]phenol | C | B | | |
| 70 | 4-((E)-2-{5-[3-(methyloxy)phenyl]-1H-pyrazol-3-yl}ethenyl)phenol | C | C | | |

TABLE 2-continued

| Entry | Name | c-Kit | flt-3 | EphB4 | EGFR |
|---|---|---|---|---|---|
| 71 | 1,1-dimethylethyl(4-{3-[(E)-2-phenylethenyl]-1H-pyrazol-5-yl}phenyl)carbamate | C | C | | |
| 72 | 4-{(E)-2-[3-(3,4-dichlorophenyl)-1H-pyrazol-5-yl]ethenyl}phenol | C | C | | |
| 73 | 2-{5-[(E)-2-phenylethenyl]-1H-pyrazol-3-yl}-1-benzofuran-6-ol | C | A | | |
| 74 | 4-{(E)-2-[5-(3-fluorophenyl)-1H-pyrazol-3-yl]ethenyl}phenol | C | B | | |
| 75 | 2-(5-phenyl-1H-pyrazol-3-yl)-1H-benzimidazole | C | C | | |
| 76 | N-phenyl-N'-[4-(3-phenyl-1H-pyrazol-5-yl)phenyl]urea | C | C | D | D |
| 77 | 4-[3-(1H-benzimidazol-2-yl)-1H-pyrazol-5-yl]aniline | C | C | | |
| 78 | 4-[(E)-2-(5-biphenyl-3-yl-1H-pyrazol-3-yl)ethenyl]phenol | C | C | | |

What is claimed is:

1. A compound or pharmaceutically acceptable salt thereof of either formula VIIc or VIId,

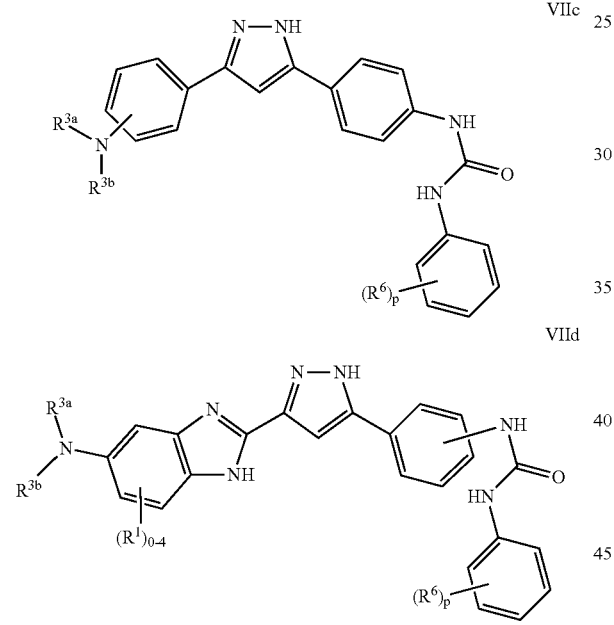

$R^{3a}$ and $R^{3b}$, together with the nitrogen to which they are attached, combine to form an optionally substituted piperazinyl;

$R^6$ is —H, halogen, haloalkyl, —CN, —NO$_2$, —OR$^3$, —N(R$^3$)R$^3$, —S(O)$_{0-2}$R$^3$, —N(R$^3$)C(=O)C(=O)N(R$^3$)R$^3$, —CO$_2$R$^3$, —C(=O)N(R$^3$)R$^3$, —N(R$^3$)SO$_2$R$^3$, —N(R$^3$)C(O)R$^3$, —NCO$_2$R$^3$, —C(=O)R$^3$, optionally substituted alkoxy, optionally substituted heterocyclyl, or optionally substituted lower alkyl; and $R^3$ is —H, optionally substituted lower alkyl, optionally substituted aryl, optionally substituted lower arylalkyl;

p is one to five;

wherein when any of said "alkyl, aryl, or heterocyclyl" are substituted, one or more hydrogen atoms of said alkyl, aryl, and heterocyclyl are replaced by alkyl, trifluoromethyl, hydroxypropyl, nitromethyl, aminoethyl, aryl, 4-hydroxyphenyl, 2,3-difluorophenyl, arylalkyl, 1-phenyl-ethyl, para-methoxyphenylethyl, heterocyclylalkyl, 1-pyridin-3-yl-ethyl, N-ethylmorphonlino, heterocyclyl, 5-chloro-pyridin-3-yl, 1-methyl-piperidin-4-yl, alkoxy, methoxyethoxy, hydroxypropyloxy, methylenedioxy, amino, methylamino, diethylamino, trifluoroacetylamino, amidino, aryloxy, para-chlorophenoxy, meta-aminophenoxy, para-phenoxyphenoxy, arylalkyloxy, 3-chlorobenzyloxy, meta-phenoxybenzyloxy, carboxy, carboalkoxy, carboxamido, benzyloxycarbonylamino, cyano, acyl, halogen, hydroxy, nitro, alkylsulfanyl, alkylsulfinyl, alkylsulfonyl, thiol, oxo, carbamyl, acylamino, hydrazino, hydroxylamino, or sulfonamide.

2. The compound according to claim 1 or pharmaceutically acceptable salt thereof wherein for VIIc, —N(R$^{3a}$)R$^{3b}$ is either meta- or para- to the pyrazole moiety; and the phenyl urea in VIId is either meta- or para- to the pyrazole moiety.

3. A compound selected from Table 3 or pharmaceutically acceptable salt thereof,

TABLE 3

| Entry | Name | Structure |
|---|---|---|
| 2 | N-[4-chloro-3-(trifluoromethyl)phenyl]-N'-(4-{3-[5-(4-ethylpiperazin-1-yl)-1H-benzimidazol-2-yl]-1H-pyrazol-5-yl}phenyl)urea | 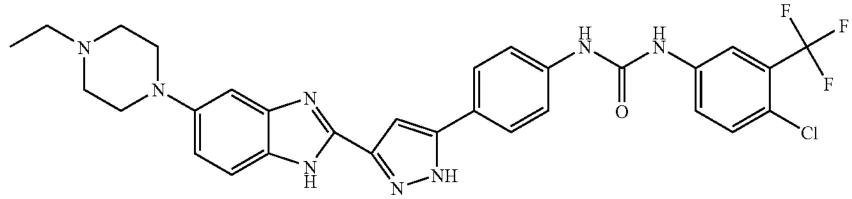 [SMILES: CCN1CCN(c2ccc3[nH]c(-c4cc(-c5ccc(NC(=O)Nc6ccc(Cl)c(C(F)(F)F)c6)cc5)[nH]n4)nc3c2)CC1] |

TABLE 3-continued

| Entry | Name | Structure |
|---|---|---|
| 3 | N-(3-ethylphenyl)-N'-(4-{3-[5-(4-ethylpiperazin-1-yl)-1H-benzimidazol-2-yl]-1H-pyrazol-5-yl}phenyl)urea | 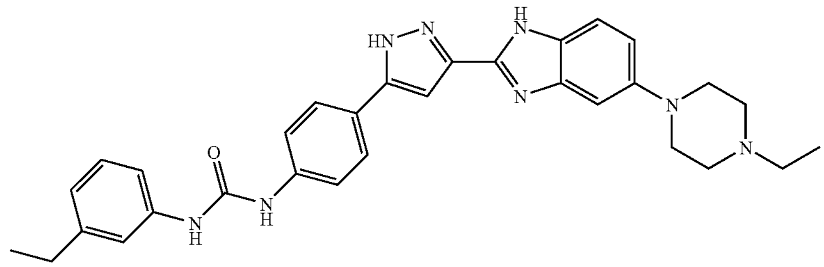 [SMILES: CCc1cccc(NC(=O)Nc2ccc(-c3cc(-c4nc5cc(N6CCN(CC)CC6)ccc5[nH]4)n[nH]3)cc2)c1] |
| 4 | N-(4-{3-[5-(4-ethylpiperazin-1-yl)-1H-benzimidazol-2-yl]-1H-pyrazol-5-yl}phenyl)-N'-[3-(trifluoromethyl)phenyl]urea | 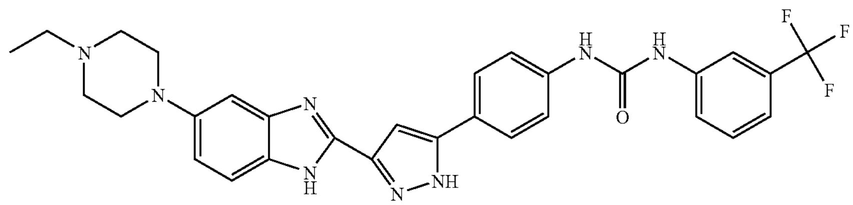 [SMILES: CCN1CCN(c2ccc3[nH]c(-c4cc(-c5ccc(NC(=O)Nc6cccc(C(F)(F)F)c6)cc5)[nH]n4)nc3c2)CC1] |
| 5 | N-(3-acetylphenyl)-N'-(4-{3-[5-(4-methylpiperazin-1-yl)-1H-benzimidazol-2-yl]-1H-pyrazol-5-yl}phenyl)urea | |
| 6 | N-(3,4-dichlorophenyl)-N'-(4-{3-[5-(4-methylpiperazin-1-yl)-1H-benzimidazol-2-yl]-1H-pyrazol-5-yl}phenyl)urea | 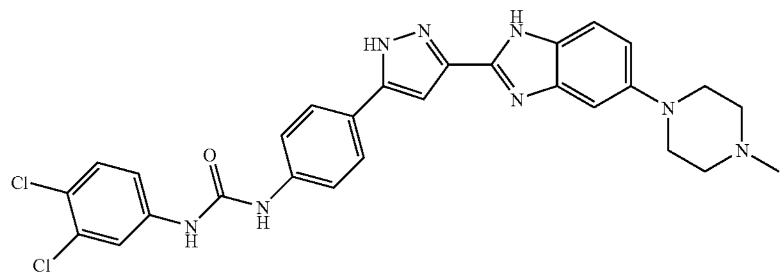 [SMILES: CN1CCN(c2ccc3[nH]c(-c4cc(-c5ccc(NC(=O)Nc6ccc(Cl)c(Cl)c6)cc5)[nH]n4)nc3c2)CC1] |
| 7 | N-(3-bromophenyl)-N'-(4-{3-[6-(4-methylpiperazin-1-yl)-1H-benzimidazol-2-yl]-1H-pyrazol-5-yl}phenyl)urea | 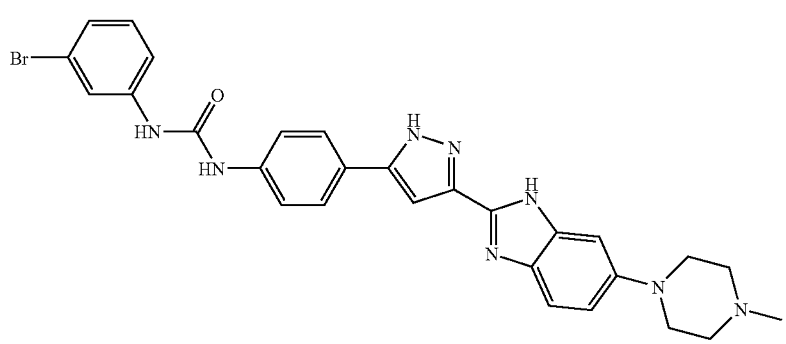 [SMILES: CN1CCN(c2ccc3nc(-c4cc(-c5ccc(NC(=O)Nc6cccc(Br)c6)cc5)[nH]n4)[nH]c3c2)CC1] |
| 8 | N-[4-fluoro-3-(trifluoromethyl)phenyl]-N'-(4-{3-[5-(4-methylpiperazin-1-yl)-1H-benzimidazol-2-yl]-1H-pyrazol-5-yl}phenyl)urea | 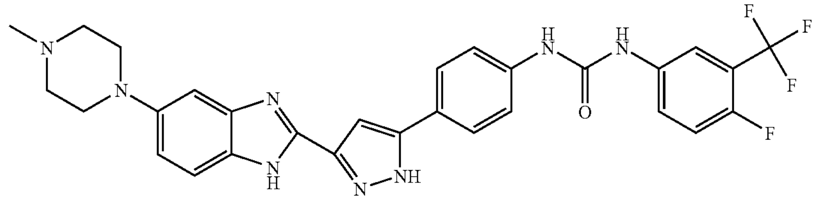 [SMILES: CN1CCN(c2ccc3[nH]c(-c4cc(-c5ccc(NC(=O)Nc6ccc(F)c(C(F)(F)F)c6)cc5)[nH]n4)nc3c2)CC1] |

TABLE 3-continued

| Entry | Name | Structure |
|---|---|---|
| 9 | N-(4-{3-[5-(4-methylpiperazin-1-yl)-1H-benzimidazol-2-yl]-1H-pyrazol-5-yl}phenyl)-N'-[4-(phenyloxy)phenyl]urea | 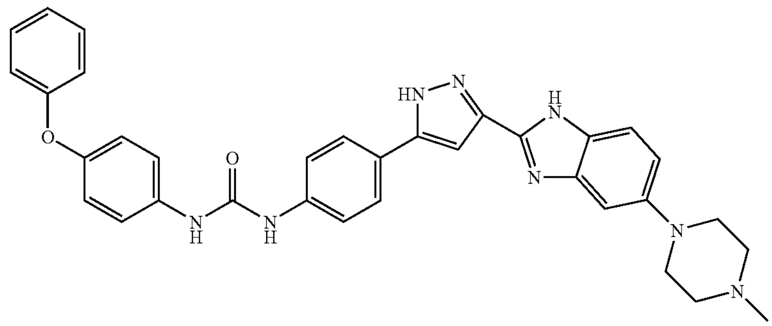 [SMILES: CN1CCN(c2ccc3[nH]c(-c4cc(-c5ccc(NC(=O)Nc6ccc(Oc7ccccc7)cc6)cc5)[nH]n4)nc3c2)CC1] |
| 10 | N-(3-chlorophenyl)-N'-(4-{3-[5-(4-methylpiperazin-1-yl)-1H-benzimidazol-2-yl]-1H-pyrazol-yl}phenyl)urea | 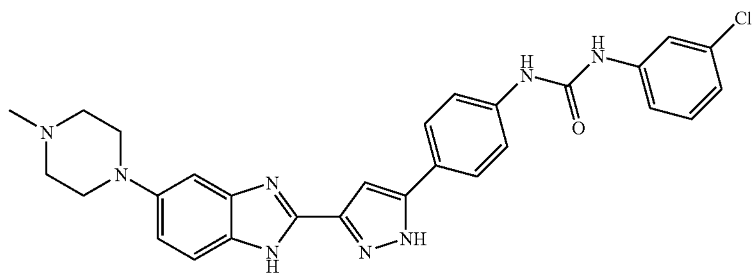 [SMILES: CN1CCN(c2ccc3[nH]c(-c4cc(-c5ccc(NC(=O)Nc6cccc(Cl)c6)cc5)[nH]n4)nc3c2)CC1] |
| 11 | N-[3,5-bis(methyloxy)phenyl]-N'-(4-{3-[6-(4-methylpiperazin-1-yl)-1H-benzimidazol-2-yl]-1H-pyrazol-5-yl}phenyl)urea | 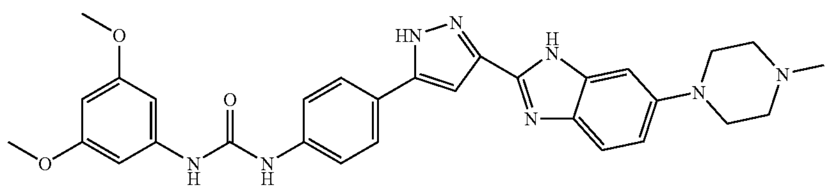 |
| 12 | N-(4-{3-[5-(4-methylpiperazin-1-yl)-1H-benzimidazol-2-yl]-1H-pyrazol-5-yl}phenyl)-N'-{4-[(trifluoromethyl)oxy]phenyl}urea | 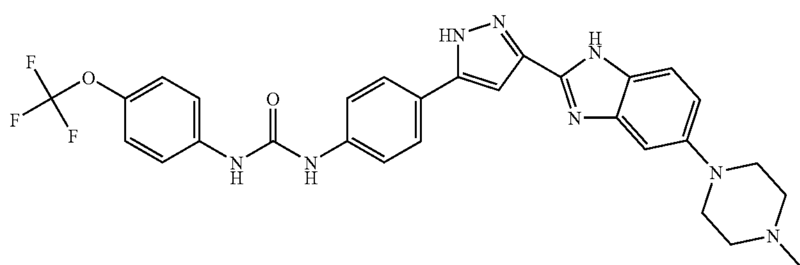 |
| 13 | N-(4-{3-[6-(4-methylpiperazin-1-yl)-1H-benzimidazol-2-yl]-1H-pyrazol-5-yl}phenyl)-N'-[4-(trifluoromethyl)phenyl]urea | 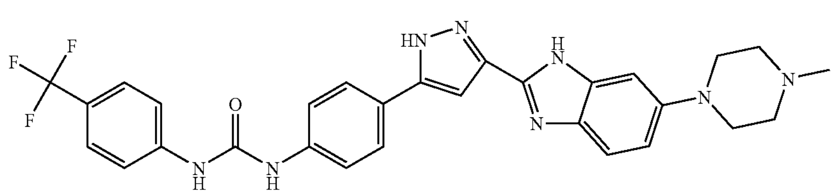 [SMILES: CN1CCN(c2ccc3nc(-c4cc(-c5ccc(NC(=O)Nc6ccc(C(F)(F)F)cc6)cc5)[nH]n4)[nH]c3c2)CC1] |
| 14 | N-[4-chloro-3-(trifluoromethyl)phenyl]-N'-(4-{3-[5-(4-methylpiperazin-1-yl)-1H-benzimidazol-2-yl]-1H-pyrazol-5-yl}phenyl)urea | 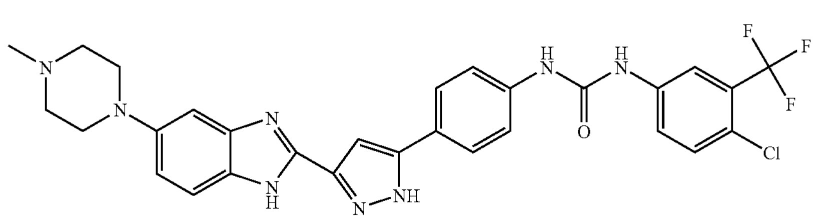 [SMILES: CN1CCN(c2ccc3[nH]c(-c4cc(-c5ccc(NC(=O)Nc6ccc(Cl)c(C(F)(F)F)c6)cc5)[nH]n4)nc3c2)CC1] |

TABLE 3-continued

| Entry | Name | Structure |
|---|---|---|
| 15 | N-(4-{3-[5-(4-methylpiperazin-1-yl)-1H-benzimidazol-2-yl]-1H-pyrazol-5-yl}phenyl)-N'-[3-(trifluoromethyl)phenyl]urea | 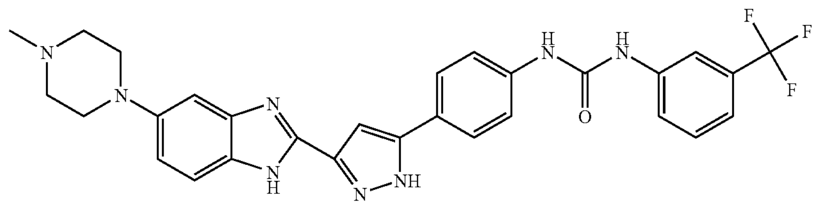 [SMILES: CN1CCN(c2ccc3[nH]c(-c4cc(-c5ccc(NC(=O)Nc6cccc(C(F)(F)F)c6)cc5)[nH]n4)nc3c2)CC1] |
| 16 | N-[4-chloro-3-(trifluoromethyl)phenyl]-N'-(4-{3-[4-(4-methylpiperazin-1-yl)phenyl]-1H-pyrazol-5-yl}phenyl)urea | 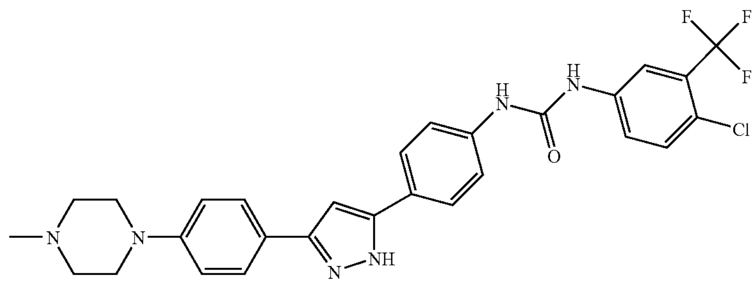 [SMILES: CN1CCN(c2ccc(-c3cc(-c4ccc(NC(=O)Nc5ccc(Cl)c(C(F)(F)F)c5)cc4)[nH]n3)cc2)CC1] |
| 17 | N-(3,4-dimethylphenyl)-N'-(4-{5-[4-(4-methylpiperazin-1-yl)phenyl]-1H-pyrazol-3-yl}phenyl)urea | 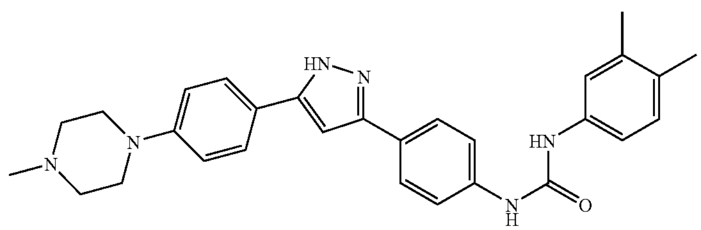 |
| 18 | N-(4-chlorophenyl)-N'-(4-{3-[5-(4-methylpiperazin-1-yl)-1H-benzimidazol-2-yl]-1H-pyrazol-5-yl}phenyl)urea | 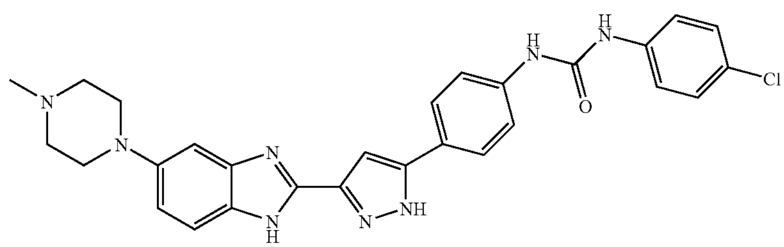 [SMILES: CN1CCN(c2ccc3[nH]c(-c4cc(-c5ccc(NC(=O)Nc6ccc(Cl)cc6)cc5)[nH]n4)nc3c2)CC1] |
| 19 | N-(3,5-difluorophenyl)-N'-(4-{3-[5-(4-methylpiperazin-1-yl)-1H-benzimidazol-2-yl]-1H-pyrazol-5-yl}phenyl)urea | 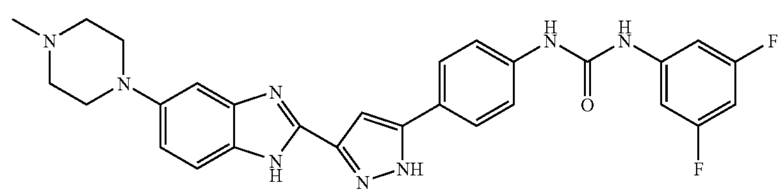 [SMILES: CN1CCN(c2ccc3[nH]c(-c4cc(-c5ccc(NC(=O)Nc6cc(F)cc(F)c6)cc5)[nH]n4)nc3c2)CC1] |
| 20 | N-[3-(methyloxy)phenyl]-N'-(4-{3-[5-(4-methylpiperazin-1-yl)-1H-benzimidazol-2-yl]-1H-pyrazol-5-yl}phenyl)urea | 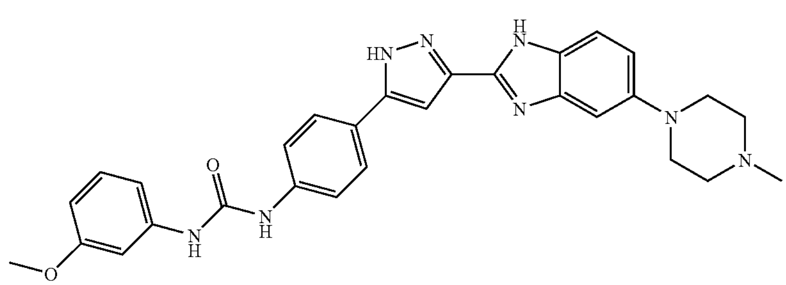 |

TABLE 3-continued

| Entry | Name | Structure |
|---|---|---|
| 21 | N-[4-chloro-3-(trifluoromethyl)phenyl]-N'-(4-{3-[4-(4-ethylpiperazin-1-yl)phenyl]-1H-pyrazol-5-yl}phenyl)urea | 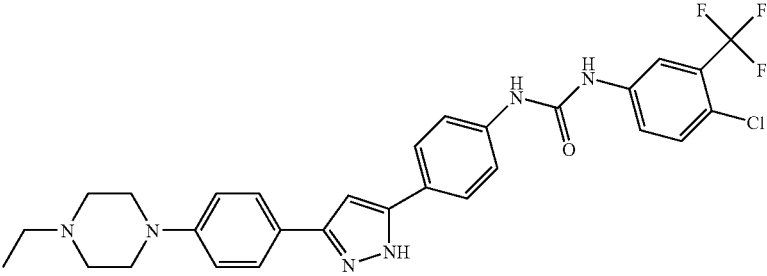 [SMILES: CCN1CCN(c2ccc(-c3cc(-c4ccc(NC(=O)Nc5ccc(Cl)c(C(F)(F)F)c5)cc4)[nH]n3)cc2)CC1] |
| 22 | N-(3-fluorophenyl)-N'-(4-{3-[5-(4-methylpiperazin-1-yl)-1H-benzimidazol-2-yl]-1H-pyrazol-5-yl}phenyl)urea | 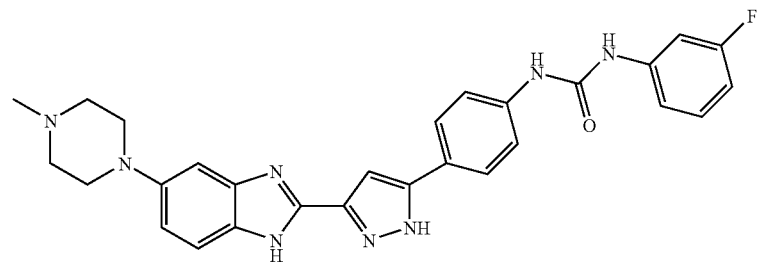 [SMILES: CN1CCN(c2ccc3[nH]c(-c4cc(-c5ccc(NC(=O)Nc6cccc(F)c6)cc5)[nH]n4)nc3c2)CC1] |
| 23 | N-(4-fluorophenyl)-N'-(4-{3-[5-(4-methylpiperazin-1-yl)-1H-benzimidazol-2-yl]-1H-pyrazol-5-yl}phenyl)urea | 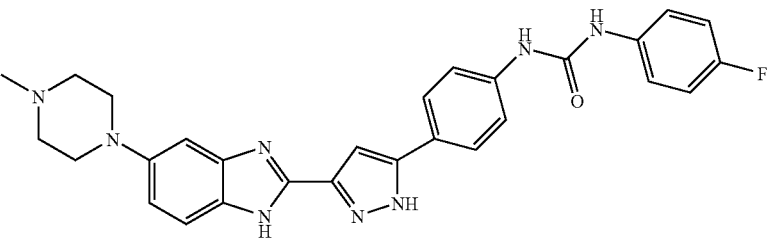 [SMILES: CN1CCN(c2ccc3[nH]c(-c4cc(-c5ccc(NC(=O)Nc6ccc(F)cc6)cc5)[nH]n4)nc3c2)CC1] |
| 24 | N-(3-cyanophenyl)-N'-(4-{3-[6-(4-methylpiperazin-1-yl)-1H-benzimidazol-2-yl]-1H-pyrazol-5-yl}phenyl)urea | 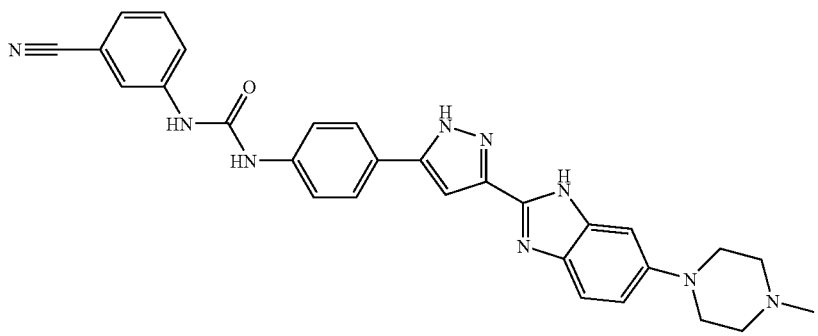 [SMILES: CN1CCN(c2ccc3nc(-c4cc(-c5ccc(NC(=O)Nc6cccc(C#N)c6)cc5)[nH]n4)[nH]c3c2)CC1] |
| 25 | N-(3,4-difluorophenyl)-N'-(4-{3-[5-(4-methylpiperazin-1-yl)-1H-benzimidazol-2-yl]-1H-pyrazol-5-yl}phenyl)urea | 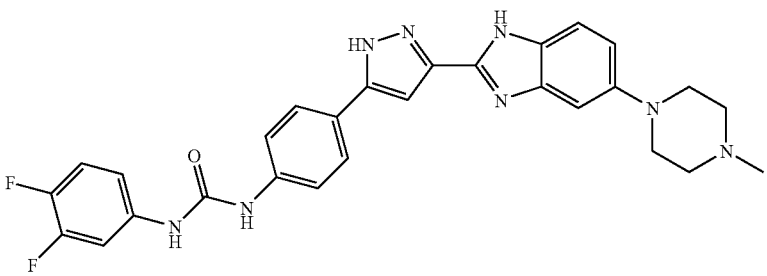 [SMILES: CN1CCN(c2ccc3[nH]c(-c4cc(-c5ccc(NC(=O)Nc6ccc(F)c(F)c6)cc5)[nH]n4)nc3c2)CC1] |

TABLE 3-continued

| Entry | Name | Structure |
|---|---|---|
| 26 | N-[3,4-bis(methyloxy)phenyl]-N'-(4-{3-[5-(4-methylpiperazin-1-yl)-1H-benzimidazol-2-yl]-1H-pyrazol-5-yl}phenyl)urea | 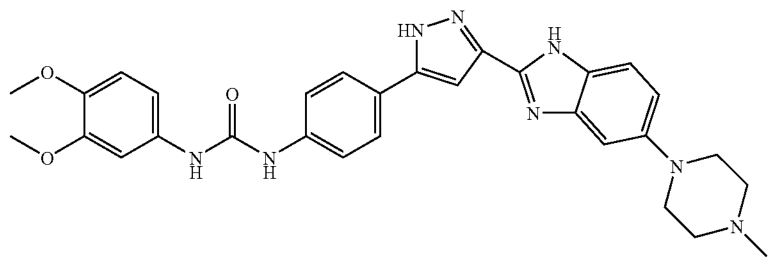 |
| 27 | N-[5-chloro-2-(methyloxy)phenyl]-N'-(4-{5-[4-(4-methylpiperazin-1-yl)phenyl]-1H-pyrazol-3-yl}phenyl)urea | 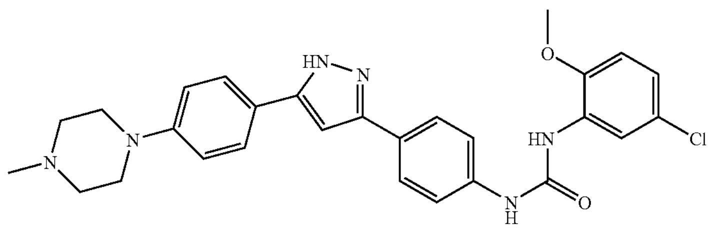 [SMILES: COc1ccc(Cl)cc1NC(=O)Nc1ccc(-c2cc(-c3ccc(N4CCN(C)CC4)cc3)[nH]n2)cc1] |
| 28 | N-(4-{5-[4-(4-methylpiperazin-1-yl)phenyl]-1H-pyrazol-3-yl}phenyl)-N'-[4-(phenyloxy)phenyl]urea | 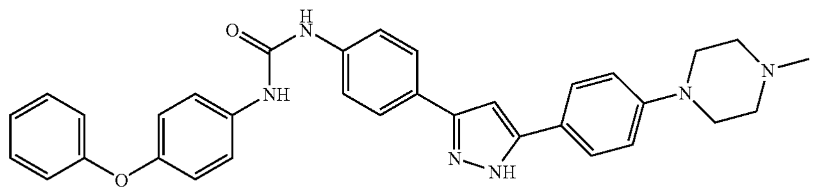 [SMILES: CN1CCN(c2ccc(-c3cc(-c4ccc(NC(=O)Nc5ccc(Oc6ccccc6)cc5)cc4)n[nH]3)cc2)CC1] |
| 29 | N-(2,4-difluorophenyl)-N'-(4-{3-[6-(4-ethylpiperazin-1-yl)-1H-benzimidazol-2-yl]-1H-pyrazol-5-yl}phenyl)urea | 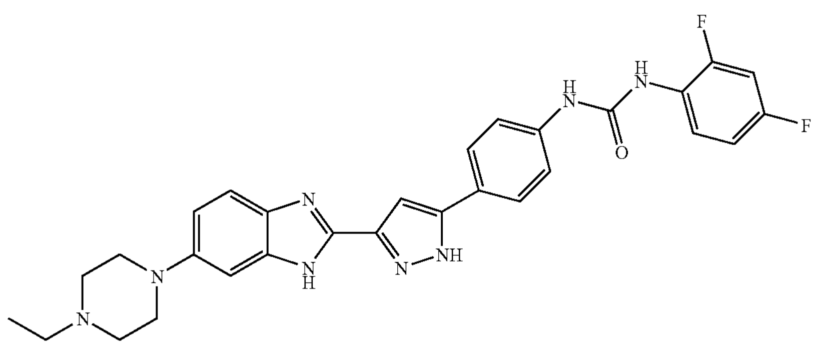 [SMILES: CCN1CCN(c2ccc3nc(-c4cc(-c5ccc(NC(=O)Nc6ccc(F)cc6F)cc5)[nH]n4)[nH]c3c2)CC1] |
| 30 | N-{4-[3-(1H-benzimidazol-2-yl)-1H-pyrazol-5-yl]phenyl}-N'-[4-chloro-3-(trifluoromethyl)phenyl]urea | 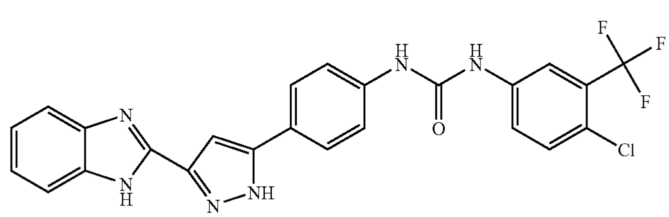 [SMILES: O=C(Nc1ccc(-c2cc(-c3nc4ccccc4[nH]3)n[nH]2)cc1)Nc1ccc(Cl)c(C(F)(F)F)c1] |
| 31 | N-{4-[3-(1H-benzimidazol-2-yl)-1H-pyrazol-5-yl]phenyl}-N'-[2-fluoro-5-(trifluoromethyl)phenyl]urea | 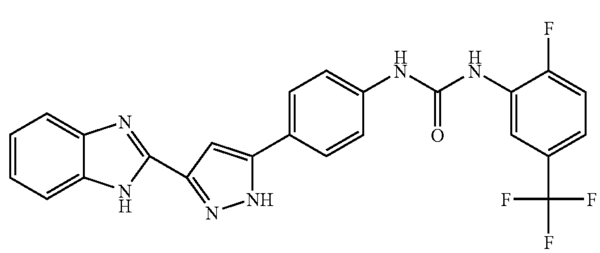 [SMILES: O=C(Nc1ccc(-c2cc(-c3nc4ccccc4[nH]3)n[nH]2)cc1)Nc1cc(C(F)(F)F)ccc1F] |

TABLE 3-continued

| Entry | Name | Structure |
|---|---|---|
| 32 | N-(2,4-difluorophenyl)-N'-(4-{3-[5-(4-methylpiperazin-1-yl)-1H-benzimidazol-2-yl]-1H-pyrazol-5-yl}phenyl)urea | 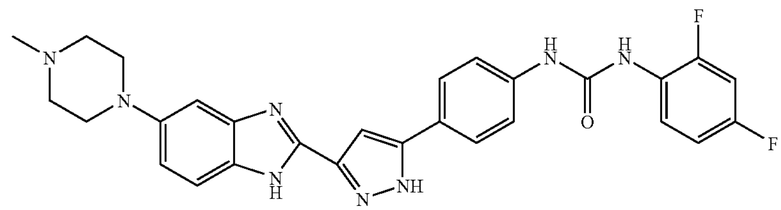 [SMILES: CN1CCN(c2ccc3[nH]c(-c4cc(-c5ccc(NC(=O)Nc6ccc(F)cc6F)cc5)[nH]n4)nc3c2)CC1] |
| 34 | N-[3,5-bis(trifluoromethyl)phenyl]-N'-(4-{3-[5-(4-methylpiperazin-1-yl)-1H-benzimidazol-2-yl]-1H-pyrazol-5-yl}phenyl)urea | 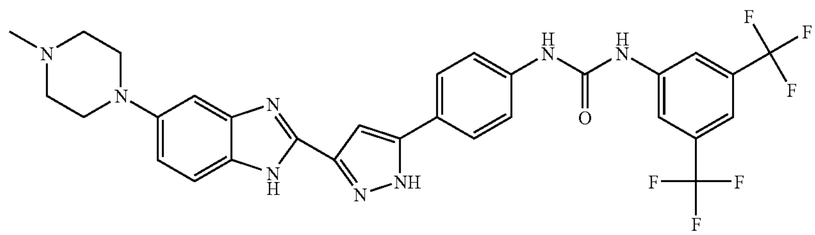 [SMILES: CN1CCN(c2ccc3[nH]c(-c4cc(-c5ccc(NC(=O)Nc6cc(C(F)(F)F)cc(C(F)(F)F)c6)cc5)[nH]n4)nc3c2)CC1] |
| 35 | N-(2-fluorophenyl)-N'-(4-{3-[5-(4-methylpiperazin-1-yl)-1H-benzimidazol-2-yl]-1H-pyrazol-5-yl}phenyl)urea | 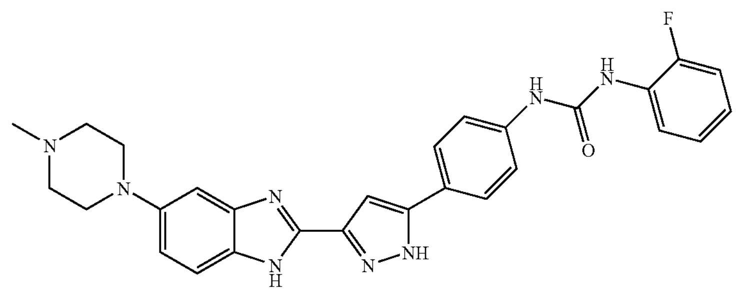 [SMILES: CN1CCN(c2ccc3[nH]c(-c4cc(-c5ccc(NC(=O)Nc6ccccc6F)cc5)[nH]n4)nc3c2)CC1] |
| 38 | N-(5-fluoro-2-methylphenyl)-N'-(4-{3-[6-(4-methylpiperazin-1-yl)-1H-benzimidazol-2-yl]-1H-pyrazol-5-yl}phenyl)urea | 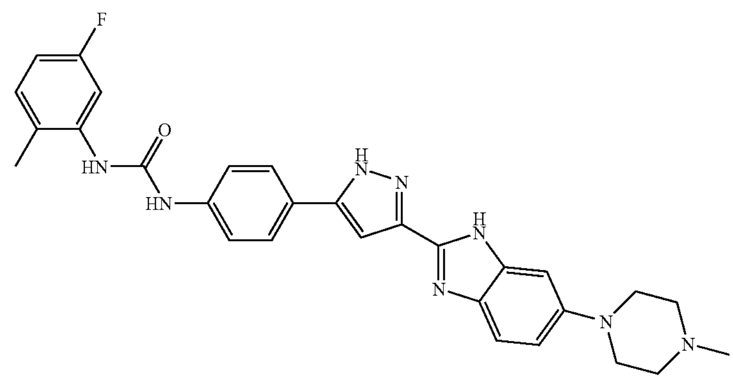 [SMILES: Cc1ccc(F)cc1NC(=O)Nc1ccc(-c2cc(-c3nc4ccc(N5CCN(C)CC5)cc4[nH]3)n[nH]2)cc1] |
| 39 | N-(4-{3-[5-(4-methylpiperazin-1-yl)-1H-benzimidazol-2-yl]-1H-pyrazol-5-yl}phenyl)-N'-phenylurea | 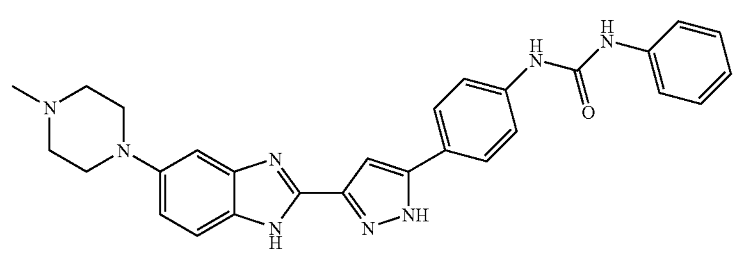 [SMILES: CN1CCN(c2ccc3[nH]c(-c4cc(-c5ccc(NC(=O)Nc6ccccc6)cc5)[nH]n4)nc3c2)CC1] |

TABLE 3-continued

| Entry | Name | Structure |
|---|---|---|
| 40 | N-[4-chloro-3-(trifluoromethyl)phenyl]-N'-(4-{3-[3-(4-methylpiperazin-1-yl)phenyl]-1H-pyrazol-5-yl}phenyl)urea | 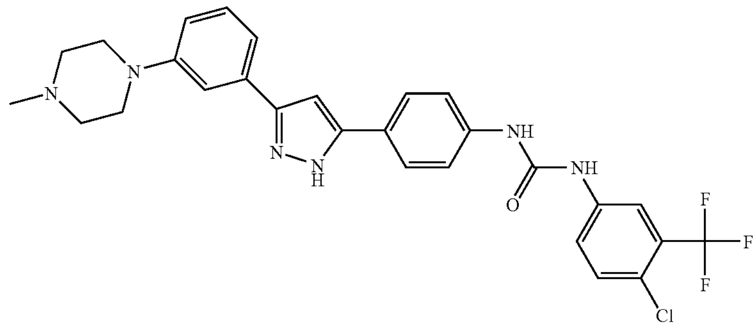 [SMILES: CN1CCN(c2cccc(-c3cc(-c4ccc(NC(=O)Nc5ccc(Cl)c(C(F)(F)F)c5)cc4)[nH]n3)c2)CC1] |
| 41 | N-(2,4-difluorophenyl)-N'-(4-{3-[4-(4-methylpiperazin-1-yl)phenyl]-1H-pyrazol-5-yl}phenyl)urea | 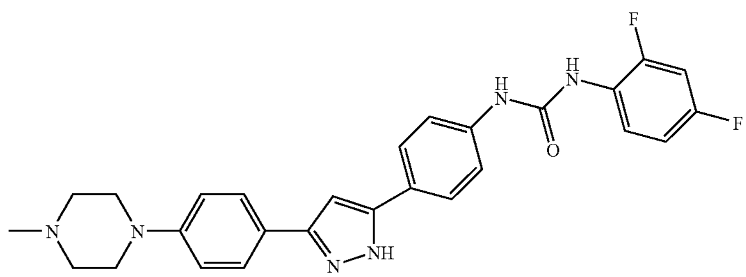 [SMILES: CN1CCN(c2ccc(-c3cc(-c4ccc(NC(=O)Nc5ccc(F)cc5F)cc4)[nH]n3)cc2)CC1] |
| 42 | N-(2,3-dihydro-1,4-benzodioxin-6-yl)-N'-(4-{5-[4-(4-methylpiperazin-1-yl)phenyl]-1H-pyrazol-3-yl}phenyl)urea | 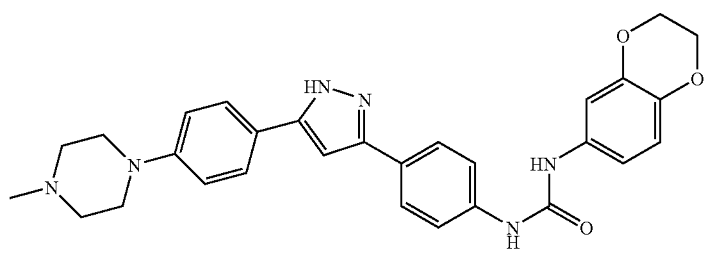 [SMILES: CN1CCN(c2ccc(-c3cc(-c4ccc(NC(=O)Nc5ccc6c(c5)OCCO6)cc4)n[nH]3)cc2)CC1] |
| 43 | N-[2,4-bis(methyloxy)phenyl]-N'-(4-{5-[4-(4-methylpiperazin-1-yl)phenyl]-1H-pyrazol-3-yl}phenyl)urea | 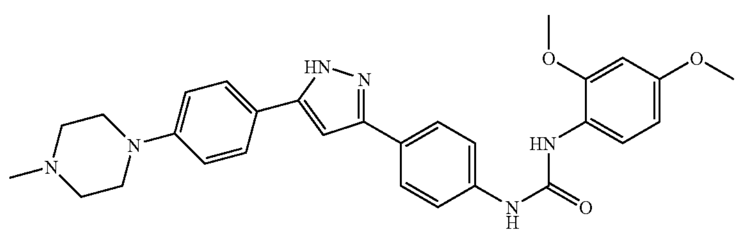 |
| 46 | N-(4-{3-[4-(4-methylpiperazin-1-yl)phenyl]-1H-pyrazol-5-yl}phenyl)-N'-(2-phenylethyl)ethanediamide | 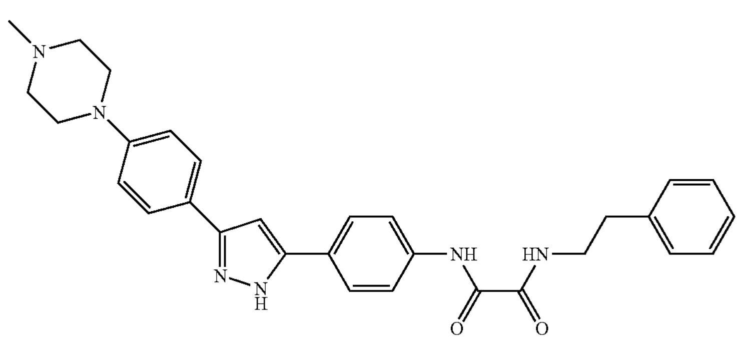 [SMILES: CN1CCN(c2ccc(-c3cc(-c4ccc(NC(=O)C(=O)NCCc5ccccc5)cc4)[nH]n3)cc2)CC1] |

TABLE 3-continued

| Entry | Name | Structure |
|---|---|---|
| 50 | N-[4-chloro-3-(trifluoromethyl)phenyl]-N'-[4-(3-phenyl-1H-pyrazol-5-yl)phenyl]urea | 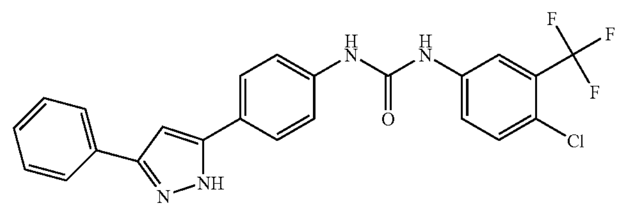 [SMILES: O=C(Nc1ccc(-c2cc(-c3ccccc3)n[nH]2)cc1)Nc1ccc(Cl)c(C(F)(F)F)c1] |
| 52 | 1,1-dimethylethyl{4-[3-(1H-benzimidazol-2-yl)-1H-pyrazol-5-yl]phenyl}carbamate | 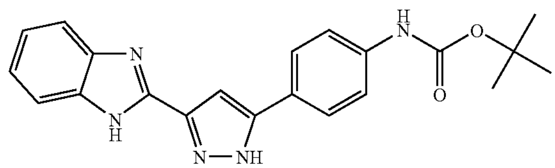 [SMILES: CC(C)(C)OC(=O)Nc1ccc(-c2cc(-c3nc4ccccc4[nH]3)n[nH]2)cc1] |
| 53 | N-(5-fluoro-2-methylphenyl)-N'-(4-{5-[4-(4-methylpiperazin-1-yl)phenyl]-1H-pyrazol-3-yl}phenyl)urea | 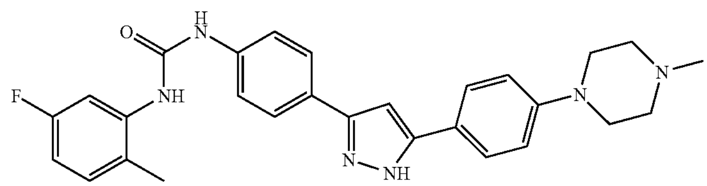 [SMILES: Cc1ccc(F)cc1NC(=O)Nc1ccc(-c2cc(-c3ccc(N4CCN(C)CC4)cc3)[nH]n2)cc1] |
| 64 | N-(1,1-dimethylethyl)-N'-(4-{3-[5-(4-ethylpiperazin-1-yl)-1H-benzimidazol-2-yl]-1H-pyrazol-5-yl}phenyl)urea | 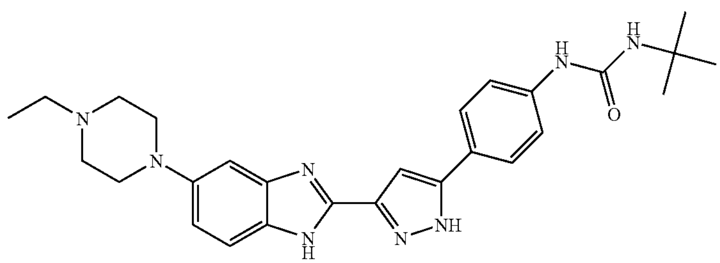 [SMILES: CCN1CCN(c2ccc3[nH]c(-c4cc(-c5ccc(NC(=O)NC(C)(C)C)cc5)[nH]n4)nc3c2)CC1] |
| 76 | N-phenyl-N'-[4-(3-phenyl-1H-pyrazol-5-yl)phenyl]urea | 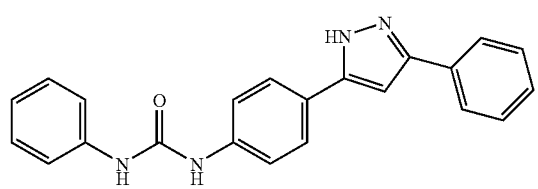 [SMILES: O=C(Nc1ccccc1)Nc1ccc(-c2cc(-c3ccccc3)n[nH]2)cc1] |
| 77 | 4-[3-(1H-benzimidazol-2-yl)-1H-pyrazol-5-yl]aniline | 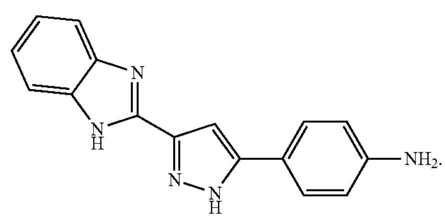 [SMILES: Nc1ccc(-c2cc(-c3nc4ccccc4[nH]3)n[nH]2)cc1] |

4. A pharmaceutical composition comprising the compound or pharmaceutically acceptable salt thereof according to any one of claims 1-3 and a pharmaceutically acceptable carrier.

5. A method of modulating the in vivo activity of a kinase, the method comprising administering to a subject an effective amount of a composition comprising at least one of the compounds or a pharmaceutically acceptable salt thereof according to any of claims 1-3, wherein the kinase is c-Kit or flt-3.

6. A method of treating a c-Kit- or flt-3-mediated diseases or disorders, the method comprising administering, to a mammal in need thereof, a therapeutically effective amount of a composition comprising at least one of the compounds or a pharmaceutically acceptable salt thereof according to any of claims 1-3.

7. A method of screening for a modulator of a kinase, the method comprising combining at least one of the compounds or a pharmaceutically acceptable salt thereof according to any of claims 1-3 and at least one candidate agent and determining the effect of the candidate agent on the activity of said kinase, wherein the kinase is c-Kit or flt-3.

8. A method of inhibiting proliferative activity in a cell or a plurality of cells, the method comprising administering an effective amount of at least one of the compounds or a pharmaceutically acceptable salt thereof according to any of claims 1-3 to said cell or said plurality of cells, wherein the proliferative activity is modulated by c-Kit or flt-3.

\* \* \* \* \*